US009492805B2

(12) United States Patent
Gleason et al.

(10) Patent No.: US 9,492,805 B2
(45) Date of Patent: Nov. 15, 2016

(54) INITIATED CHEMICAL VAPOR DEPOSITION OF VINYL POLYMERS FOR THE ENCAPSULATION OF PARTICLES

(75) Inventors: Karen K. Gleason, Lexington, MA (US); Kenneth K. S. Lau, Somerville, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 1436 days.

(21) Appl. No.: 11/589,683

(22) Filed: Oct. 30, 2006

(65) Prior Publication Data

US 2007/0104860 A1    May 10, 2007

Related U.S. Application Data

(60) Provisional application No. 60/732,371, filed on Nov. 1, 2005.

(51) Int. Cl.
| | |
|---|---|
| *B01J 13/14* | (2006.01) |
| *B01J 13/04* | (2006.01) |
| *A61K 9/20* | (2006.01) |

(Continued)

(52) U.S. Cl.
CPC .............. *B01J 13/04* (2013.01); *A61K 9/2077* (2013.01); *A61K 9/5026* (2013.01); *B01J 13/14* (2013.01); *C23C 16/4417* (2013.01); *C23C 16/452* (2013.01)

(58) Field of Classification Search
CPC ............................ C23C 16/4417; B01J 13/04
USPC ............................................ 427/213, 255.11
See application file for complete search history.

(56) References Cited

U.S. PATENT DOCUMENTS

| 4,810,524 A | * | 3/1989 | Nakayama et al. | .......... 427/490 |
| 4,973,064 A | * | 11/1990 | Hosoya | .......................... 277/410 |

(Continued)

FOREIGN PATENT DOCUMENTS

| JP | 2005149764 | 6/2005 |
| JP | 2005200643 | 7/2005 |

(Continued)

OTHER PUBLICATIONS

Jiang et al., Close pacing of polymer-coated monodisperse silica, Journal of Materials Science Letters, 9 (1990), 1272-1273.*

(Continued)

*Primary Examiner* — Tabatha Penny
(74) *Attorney, Agent, or Firm* — Foley Hoag LLP

(57) ABSTRACT

Described herein are all-dry encapsulation methods that enable well-defined polymers to be applied around particles. One aspect of the invention relates to a method of coating a particle, comprising the steps of: placing said particle in a vessel at a pressure; rotating said vessel at a rotating speed for a period of time; mixing together a first gaseous monomer at a first flow rate, and a gaseous initiator at a second flow rate, thereby forming a mixture; introducing said mixture into said vessel via a vapor feedline; heating said mixture, thereby forming a reactive mixture; contacting said particle with said reactive mixture; thereby forming a polymer coating on said particle. The methods may be modified forms of initiated chemical vapor deposition using a thermally-initiated radical polymerization to create conformal coatings around individual particles while avoiding agglomeration. Particle surfaces may be coated with a range of functional groups.

20 Claims, 26 Drawing Sheets

(51) Int. Cl.
*A61K 9/50* (2006.01)
*C23C 16/44* (2006.01)
*C23C 16/452* (2006.01)

(56) References Cited

U.S. PATENT DOCUMENTS

| | | | |
|---|---|---|---|
| 5,061,630 A * | 10/1991 | Knopf et al. | 422/500 |
| 5,795,922 A * | 8/1998 | Demian et al. | 523/117 |
| 6,613,383 B1 | 9/2003 | George et al. | |
| 6,913,827 B2 | 7/2005 | George et al. | |
| 2003/0026989 A1 | 2/2003 | George et al. | |
| 2004/0132859 A1* | 7/2004 | Puckett, Jr et al. | 523/118 |
| 2004/0157952 A1* | 8/2004 | Soffiati et al. | 523/115 |
| 2005/0009002 A1 | 1/2005 | Chen et al. | |
| 2007/0032620 A1 | 2/2007 | Gleason et al. | |

FOREIGN PATENT DOCUMENTS

| WO | WO-02/075309 | 9/2002 |
|---|---|---|
| WO | WO-02/096474 | 12/2002 |

OTHER PUBLICATIONS

Mao et al., Hot Filament Chemical Vapor Deposition of Poly(glycidyl methacrylate) Thin Films Using tert-Butyl Peroxide as an Initiator, Langmuir (2004), 20, 2484-2488.*

Zeng et al., Preparation of Epoxy-Functionalized Polystyrene/Silica Core-Shell Composite Nanoparticles, Journal of Polymer Science (Mar. 25, 2004), pp. 2253-2262.*

Cleland, J. L. et al., "Recombinant human growth hormone poly(lactic-co-glycolic acid) microsphere formulation development", *Advanced Drug Delivery Reviews*, 28:71-84 (Elsevier Science B.V., 1997).

Deumie, C. et al., "Overcoated microspheres for specific optical powders", *Applied Optics*, 41(16):3299-3305 (Optical Society of America, 2002).

Guignon B., et al., "Fluid Bed Encapsulation of Particles: Principles and Practice", *Drying Technology*, 20(2):419-447 (Marcel Dekker, Inc., 2002).

Kage, H. et al., "Effect of solid circulation rate on coating efficiency and agglomeration in circulating fluidized bed type coater", *Powder Technology*, 130:203-210 (Elsevier Science B.V., 2003).

Lau, K. K. S. et al., "Initiated Chemical Vapor Deposition (iCVD) of Poly(alkyl acrylates): A Kinetic Model", *Macromolecules*, 39:3695-3703 (American Chemical Society, 2006).

Lau, K. K. S. et al., "Initiated Chemical Vapor Deposition (iCVD) of Poly(alkyl acrylates): An Experimental Study", *Macromolecules*, 39:3688-3694 (American Chemical Society, 2006).

Lee, J. Y. et al., "Hydrogen Bonding in Polymer Blends. 3. Blends Involving Polymers Containing Methacrylic Acid and Ether Groups", *Macromolecules*, 21:346-354 (American Chemical Society, 1988).

Link, K. C. et al., "Fluidized bed spray granulation Investigation of the coating process on a single sphere", *Chemical Engineering and Processing*, 36(6):443-456 (Elsevier Science S. A., 1997).

Mengel, C. et al., Preparation and Modification of Poly(methacrylic acid) and Poly(acrylic acid) Multilayers, *Langmuir*, 18:6365-6372 (American Chemical Society, 2002).

Okada, H., "One- and three-month release injectable microspheres of the LH-RH superagonist leuprorelin acetate", *Advanced Drug Delivery Reviews*, 28:43-70 (Elsevier Science B.V., 1997).

Lau, K. K. S. et al., "Particle Surface Design using an All-Dry Encapsulation Method", *Adv. Mater.*, 18:1972-1977 (Wiley-VCH Verlag Gmbh, Weinheim, 2006).

Mao, Y. et al., "Hot Filament Chemical Vapor Deposition of Poly(glycidylmethacrylate) Thin Films Using tert-Butyl Peroxide as an Initiator," *Langmuir*, 20:2484-2488 (American Chemical Society, 2004).

Shi, D. et al., "Plasma deposition of Ultrathin polymer films on carbon nanotubes", *Applied Physics Letters*, 81(27):5216-5218 (American Institute of Physics, 2002).

Susut, C. et al., "Plasma enhanced chemical vapor depositions to encapsulate crystals in thin polymeric films: a new approach to controlling drug release rates", *Int. Journ. of Pharmac.*, 288:253-261 (Elsevier B.V., 2004).

Vollath, D. et al., "Coated nanoparticles: A new way to improved nanocomposites", *Journal of Nanoparticle Research*, 1:235-242 (Kluwer Academic Publishers, Netherlands, 1999).

Partial International Search Report dated Apr. 4, 2008.

* cited by examiner

INITIATED CHEMICAL VAPOR DEPOSITION OF VINYL POLYMERS FOR THE ENCAPSULATION OF PARTICLES

RELATED APPLICATIONS

This application claims the benefit of priority to U.S. Provisional Patent Application Ser. No. 60/732,371, filed Nov. 1, 2005, which is hereby incorporated by reference in its entirety.

BACKGROUND OF THE INVENTION

As the dimensions of particles decrease, their surface composition and surface area become leading factors in determining end-use viability. Effective ways to encapsulate and functionalize the surfaces of fine particles are becoming more important as uses of such particles become more apparent. For example, after surface modification carbon nanotubes show improved dispersion and bonding with a polymer matrix, making them potential strengthening fillers in light-weight polymer composites. [Eitan, A., Jiang, K. Y., Dukes, D., Andrews, R. & Schadler, L. S. Surface modification of multiwalled carbon nanotubes: Toward the tailoring of the interface in polymer composites. *Chem. Mater.* 15, 3198-3201 (2003); Gong, X., Liu, J., Baskaran, S., Voise, R. D. & Young, J. S. Surfactant-assisted processing of carbon nanotube/polymer composites. *Chem. Mater.* 12, 1049-1052 (2000); Mitchell, C. A., Bahr, J. L., Arepalli, S., Tour, J. M. & Krishnamoorti, R. Dispersion of functionalized carbon nanotubes in polystyrene. *Macromolecules* 35, 8825-8830 (2002); and Shaffer, M. S. P. & Windle, A. H. Fabrication and characterization of carbon nanotube/poly(vinyl alcohol) composites. *Adv. Mater.* 11, 937 (1999).] Or, for example, drug particles and drug-loaded microspheres encapsulated with pH-sensitive polymers, which provide targeted release based on the pH of the intended environment. [Uhrich, K. E., Cannizzaro, S. M., Langer, R. S. & Shakesheff, K. M. Polymeric systems for controlled drug release. *Chem. Rev.* 99, 3181-3198 (1999); Schmid, S., Wahl, M. A. & Schmidt, P. C. Enteric coating of ibuprofen crystals using modified methacrylate copolymers. *Drugs Made in Germany* 44, 12-19 (2001); Haining, W. N. et al. pH-triggered microparticles for peptide vaccination. *J. Immunol.* 173, 2578-2585 (2004); and Perumal, D. Microencapsulation of ibuprofen and Eudragit® RS 100 by the emulsion solvent diffusion technique. *Int. J. Pharm.* 218, 1-11 (2001). Biodegradable poly(alkyl cyanoacrylate) nanoparticles loaded with therapeutic agents and coated with polysorbate enable drug delivery to the brain. Kreuter, J. Nanoparticulate systems for brain delivery of drugs. *Adv. Drug Deliv. Rev.* 47, 65-81 (2001); Kreuter, J. Influence of the surface properties on nanoparticle-mediated transport of drugs to the brain. *J. Nanosci. Nanotech.* 4, 484-488 (2004); and Moghimi, S. M., Hunter, A. C. & Murray, J. C. Long-circulating and target-specific nanoparticles: Theory to practice. *Pharmacol. Rev.* 53, 283-318 (2001).] It has also been shown that magnetic nanoparticles coated with dextran give enhanced sensitivity in magnetic resonance imaging. [Chouly, C., Pouliquen, D., Lucet, I., Jeune, J. J. & Jallet, P. Development of superparamagnetic nanoparticles for MRI: Effect of particle size, charge and surface nature on biodistribution. *J. Microencapsulation* 13, 245-255 (1996). Semiconductor nanocrystals coated with amphiphilic polymer shells and other biological interfaces offer the potential for single quantum dot tracking and sensing in cell biology. Michalet, X. et al. Quantum dots for live cells, in vivo imaging, and diagnostics. *Science* 307, 538-544 (2005); and Medintz, I. L., Uyeda, H. T., Goldman, E. R. & Mattoussi, H. Quantum dot bioconjugates for imaging, labeling and sensing. *Nature Mater.* 4, 435-446 (2005).] In sum, microparticles and nanoparticles are useful in a wide range of applications in biotechnology, pharmaceutics, optics, electronics, aviation, and aerospace. The surface properties of the particles play a crucial role in determining the overall function and performance of a particle-based device; in many cases, functional polymers are used to define the final nature of the particle surface. This fact underscores the importance of strategies for optimal encapsulation, functionalization and modification with polymeric materials of the surfaces of microparticles and nanoparticles.

Current strategies for encapsulating particles with polymers are mainly liquid-based protocols that rely on applying a polymer coating solution onto a particle surface with the subsequent removal of solvent. For example, spray coating of a polymer solution onto a fluidized bed of particles allows a polymer coating to form around each particle as the solvent evaporates. [Guignon, B., Duquenoy, A. & Dumoulin, E. D. Fluid bed encapsulation of particles: principles and practice. *Drying Technol.* 20, 419-447 (2002).] In another approach, an emulsification-solvent evaporation technique, utilizing a single or double emulsion of wet polymer capsules around core microdroplets, enables a polymer to precipitate around each core particle upon solvent drying. [Rosca, I. D., Watari, F. & Uo, M. Microparticle formation and its mechanism in single and double emulsion solvent evaporation. *J. Control. Release* 99, 271-280 (2004).] Alternatively, a layer-by-layer adsorption of polyelectrolyte multilayers with alternating charge can be performed on particles in a colloidal suspension. [Caruso, F., Caruso, R. A. & Möhwald, H. Nanoengineering of inorganic and hybrid hollow spheres by colloidal templating. *Science* 282, 1111-1114 (1998); and Sukhorukov, G. B. et al. Stepwise polyelectrolyte assembly on particle surfaces: a novel approach to colloid design. *Polym. Adv. Technol.* 9, 759-767 (1998).] Among dry encapsulation methods, plasma enhanced chemical vapor deposition (PECVD) is demonstrated to provide conformal solid coatings with polymer-like compositions under a low pressure gaseous environment. Using vibration or fluidization to agitate the particles during deposition, coatings have been made on drug microcrystals, ceramic nanoparticles and carbon nanotubes. [Susut, C. & Timmons, R. B. Plasma enhanced chemical vapor depositions to encapsulate crystals in thin polymeric films: a new approach to controlling drug release rates. *Int. J. Pharm.* 288, 253-261 (2005); Vollath, D. & Szabó, D. V. Coated nanoparticles: a new way to improved nanocomposites. *J. Nanoparticle Res.* 1, 235-242 (1999); Lamparth, I., Szabó, D. V. & Vollath, D. Ceramic nanoparticles coated with polymers based on acrylic derivatives. *Macromol. Symp.* 181, 107-112 (2002); Shi, D. et al. Uniform deposition of ultrathin polymer films on the surfaces of $Al_2O_3$ nanoparticles by a plasma treatment. *Appl. Phys. Lett.* 78, 1243-1245 (2001); and Shi, D. et al. Plasma deposition of ultrathin polymer films on carbon nanotubes. *Appl. Phys. Lett.* 81, 5216-5218 (2002).]

George et al. have disclosed particles having an ultrathin, conformational coating, made using atomic layer deposition methods. These coated particles are useful as fillers for electronic packaging applications, for making ceramic or cermet parts, as supported catalysts, as well as other applications. However, these methods are limited to depositing inorganic films. [George et al. U.S. Pat. No. 6,613,383, herein incorporated by reference; George et al. U.S. Pat. No. 6,913,827, herein incorporated by reference; and George et al. United States patent application Publication No. U.S. 2003/0026989, herein incorporated by reference].

SUMMARY OF THE INVENTION

One aspect of the present invention relates to an all-dry encapsulation method that enables well-defined polymers to be applied around particles of sizes down to the nanoscale. In certain embodiments, the methods are modified forms of initiated chemical vapor deposition (iCVD) using a thermally-initiated radical polymerization to create conformal coatings around individual particles while avoiding agglomeration. The present invention also enables the coating of particle surfaces with a range of functional groups via direct incorporation of the functionality into the monomers used or indirectly through a subsequent modification of the surface of a coated particle. In certain embodiments, the method produces high quality functional polymer coatings. In one embodiment, demonstrating surface design by direct incorporation of a functional group, poly(glycidyl methacrylate) has been coated on multiwalled carbon nanotubes and glass microspheres to introduce the oxirane functionality. In another embodiment, demonstrating surface design by immobilization after encapsulation, the oxirane ring of the glycidyl group was reacted with amine-containing molecules and fluorescent markers. In another embodiment, iCVD may be used to encapsulate fine drug microcrystals (e.g., below 100 μm in size) with methacrylic acid copolymers (such as poly(methacrylic acid-co-ethyl acrylate) and poly(methacrylic acid-co-ethylene dimethyacrylate)) for the purpose of conferring enteric release properties. Remarkably, the present invention overcomes many of the challenges facing existing particle encapsulation techniques like particle agglomeration, the use of toxic solvents, and poor quality control over the polymer coating, without any liquid phase or excipient required to produce the conformal coating.

DETAILED DESCRIPTION OF THE INVENTION

Figure 1:
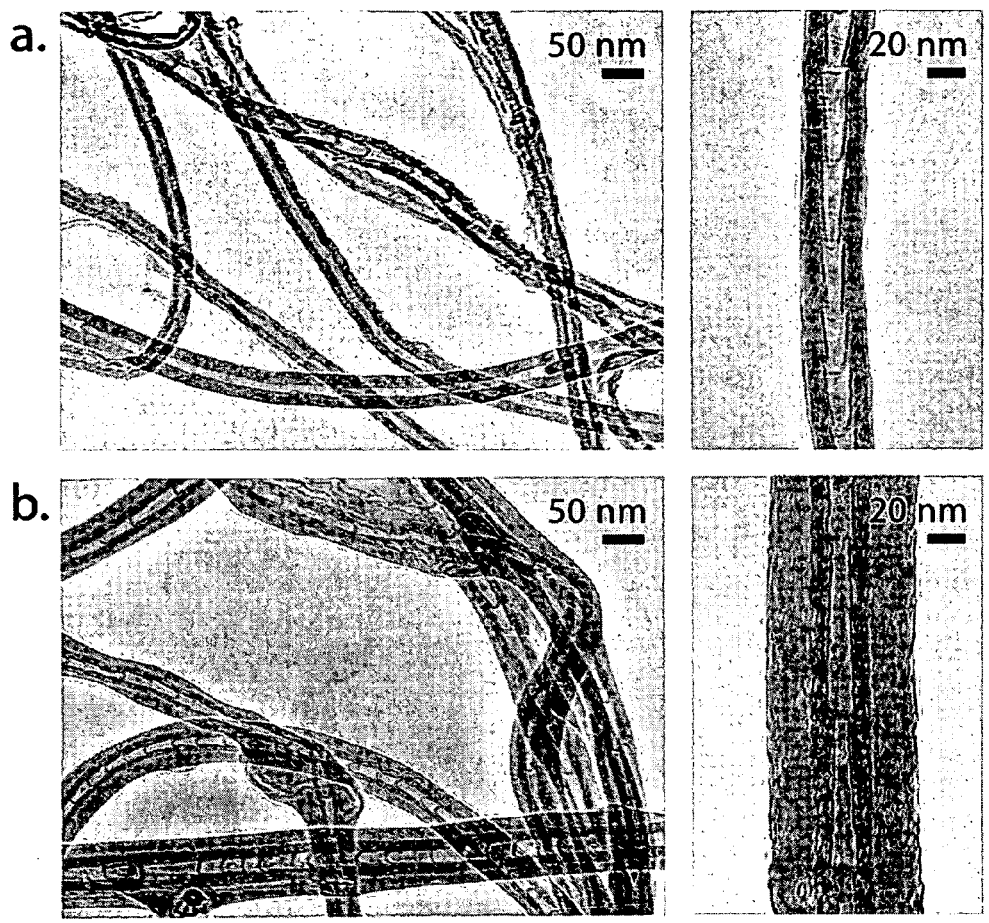
FIG. 1 depicts the encapsulation of multiwalled carbon nanotubes: (a) transmission electron microscopy (TEM) of uncoated carbon nanotubes, 20-50 nm in diameter, 5-20 μm in length; and (b) TEM of poly(glycidyl methacrylate)-coated (PGMA-coated) carbon nanotubes, showing conformal coating around each individual particle. Thickness of coating is about 25 nm.

OVERVIEW. In one embodiment of the invention, a novel dry polymer encapsulation method for microparticles and nanoparticles is provided. The method, based on initiated chemical vapor deposition (iCVD), combines a dry chemical vapor deposition environment with a radical polymerization solution chemistry without the liquid phase; by thermally activating a polymerization initiator in the vapor phase, and combining with monomer vapor, a polymerization reaction is induced on the surfaces of the particles when the reactive species are adsorbed.

In certain embodiments described herein, it is disclosed that microparticles and nanoparticles can be completely encapsulated with a polymer coating by the iCVD without particle agglomeration. In certain embodiments, using an acrylate as the encapsulating polymer, it was shown that surface design can be realized either by the introduction of the desired functionality directly into the polymer, or by a subsequent binding of surface active groups to the polymer. In one example, this result was accomplished by immobilizing fluorescent molecules through a ring-opening reaction of pendant glycidyl moieties.

SELECTED ADVANTAGES OF iCVD. Initiated chemical vapor deposition (iCVD) provides a uniform or substantially uniform coating on rough, fibrous, and porous morphologies with high surface areas. The iCVD coating process is compatible with a variety of organic and inorganic materials since it does not depend on evenly wetting the substrate surface. Importantly, the iCVD technique eliminates wet-processing steps which can damage some electronic devices and organic membranes through the wetting or the spin-coating process often used to apply solution-based films.

As mentioned above, iCVD intentionally bypasses the use of a liquid solvent phase. This is a significant advantage because liquid-based methods which rely on drying out of a wet polymer solution often suffer from particle agglomeration as a result of strong liquid surface tension forces and increasing polymer viscosity during drying which creates liquid bridges that bind the particles together especially when particles fall below 100 µm in size. [Link, K. C. & Schlunder, E. U. Fluidized bed spray granulation—investigation of the coating process on a single sphere. *Chem. Eng. Process.* 36, 443-457 (1997); and Kage, H. et al. Effect of solid circulation rate on coating efficiency and agglomeration in circulating fluidized bed type coater. *Powder Technol.* 130, 203-210 (2003).]

It has also been observed that films produced by iCVD have a better-defined chemical structure than films made by traditional "wet" processing because there are fewer reaction pathways in the iCVD methods. Therefore, iCVD provides films with a substantially lower density of dangling bonds, i.e., unpaired electrons. When such bonds are present, the film undergoes reactions with components of the ambient atmosphere (such as water, resulting in a large number of hydroxyl groups). Therefore, non-iCVD films are more susceptible to atmospheric ageing, and degradation of their optical, electrical and chemical properties.

In addition, by using controlled radical polymerization chemistries, iCVD produces exceptionally clean polymers with stoichiometric compositions, high molecular weights and having no residual solvents, excipients, glidants or plasticizers. With plasma-based dry methods, fully functional linear polymers are not produced because the high-energy plasma environment results in non-selective chemistries which lead to crosslinked networks. [d'Agostino, R., Cramarossa, F. & Fracassi, F. in *Plasma Deposition, Treatment, and Etching of Polymers* (ed d'Agostino, R.) 147 (Academic Press, San Diego, Calif., 1990).] While pulsing the plasma can allow for greater retention of chemical specificity, complete selectivity has not been achieved. [Susut, C. & Timmons, R. B. Plasma enhanced chemical vapor depositions to encapsulate crystals in thin polymeric films: a new approach to controlling drug release rates. *Int. J. Pharm.* 288, 253-261 (2005).] Further, plasma enhanced chemical deposition suffers from the drawback that the highly reactive plasma, and its associated UV discharge, may degrade the core particle during coating. [Yasuda, H. in *Plasma Polymerization* 88-101 (Academic Press, Orlando, Fla., 1985).] While deposition downstream of the plasma avoids degradation it often yields extremely low molecular weight polymers at slow rates as a consequence of the reduced concentration of reactive species away from the plasma zone. [Vollath, D. & Szabó, D. V. Coated nanoparticles: a new way to improved nanocomposites. *J. Nanoparticle Res.* 1, 235-242 (1999).]

Moreover, because the substrates to be coated may remain at room temperature, iCVD is a suitable method for encapsulating pharmaceutical products, especially those that are susceptible to thermal degradation.

Figure 7:
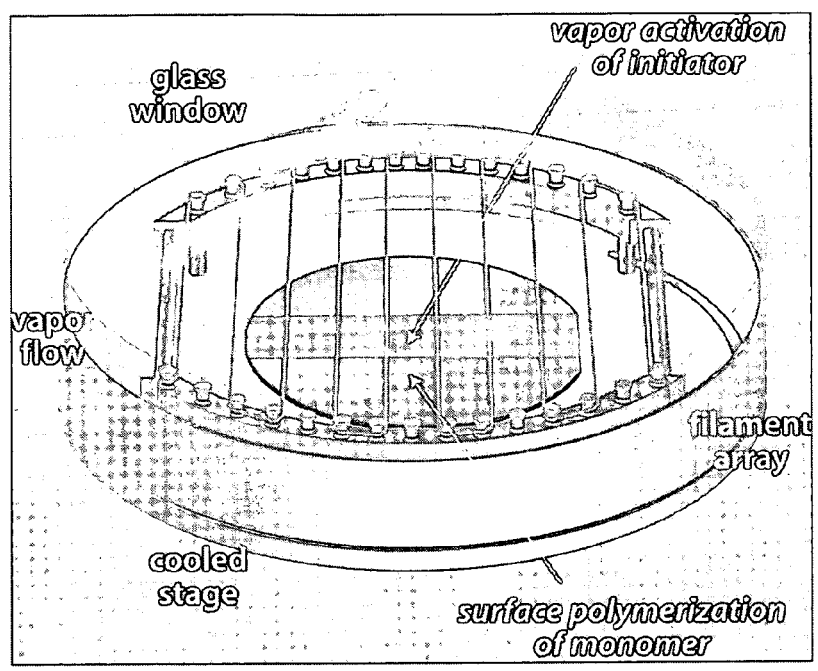
FIG. 7 depicts a conventional iCVD reactor used for coating flats.
Figure 7:
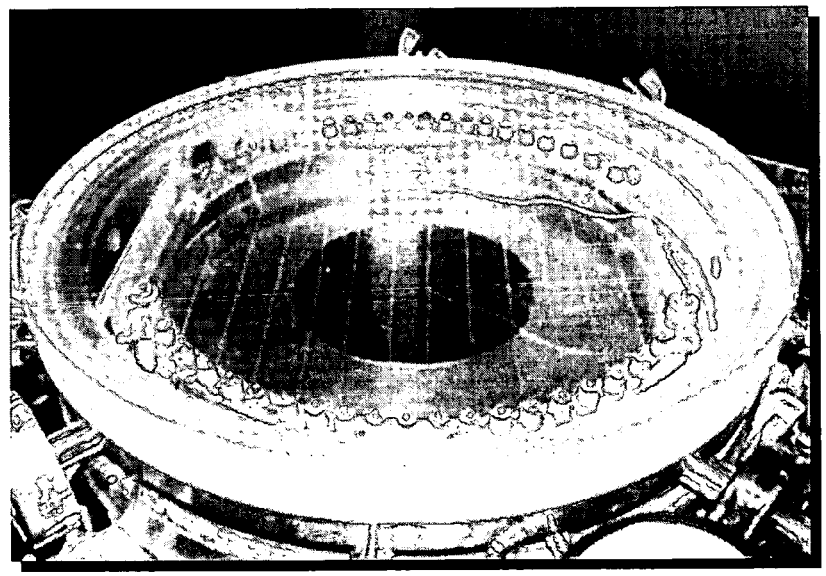

SELECTED iCVD APPARATUS. iCVD generally takes place in a reactor. Traditionally, the surface to be coated was placed on a stage in the reactor and gaseous precursor molecules are fed into the reactor; the stage may be the bottom of the reactor and not a separate entity (see, e.g., FIG. 7).

Figure 8:
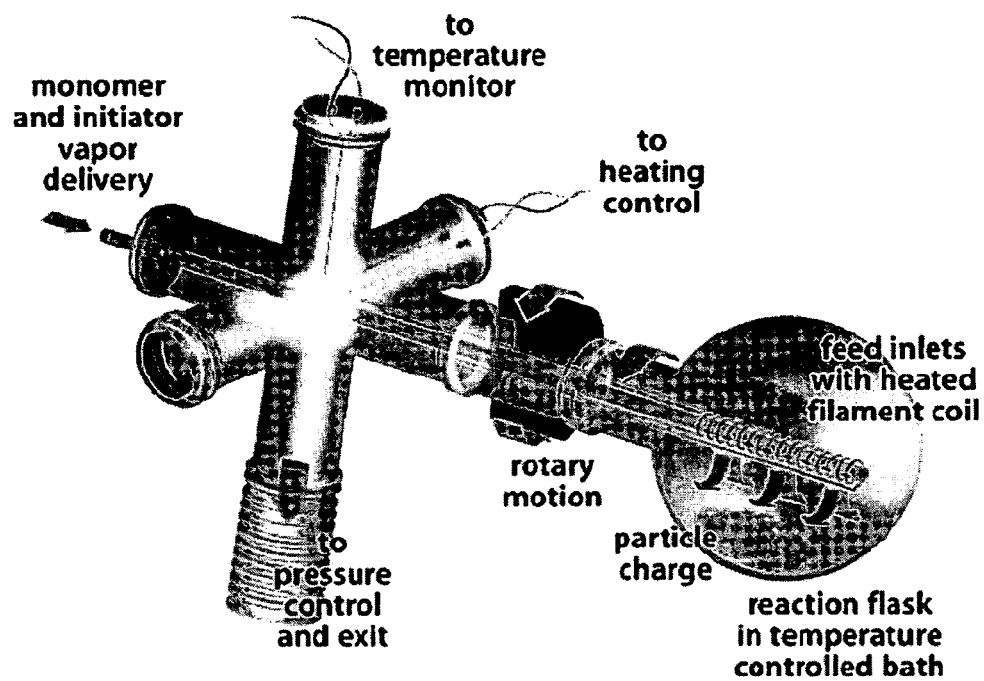
FIG. 8 depicts an example of a particle coating reactor capable of iCVD polymer encapsulation. Modified from a rotary evaporator, it contains a feedthrough (top left) and a rotovap (bottom right) attachment.
Figure 8:
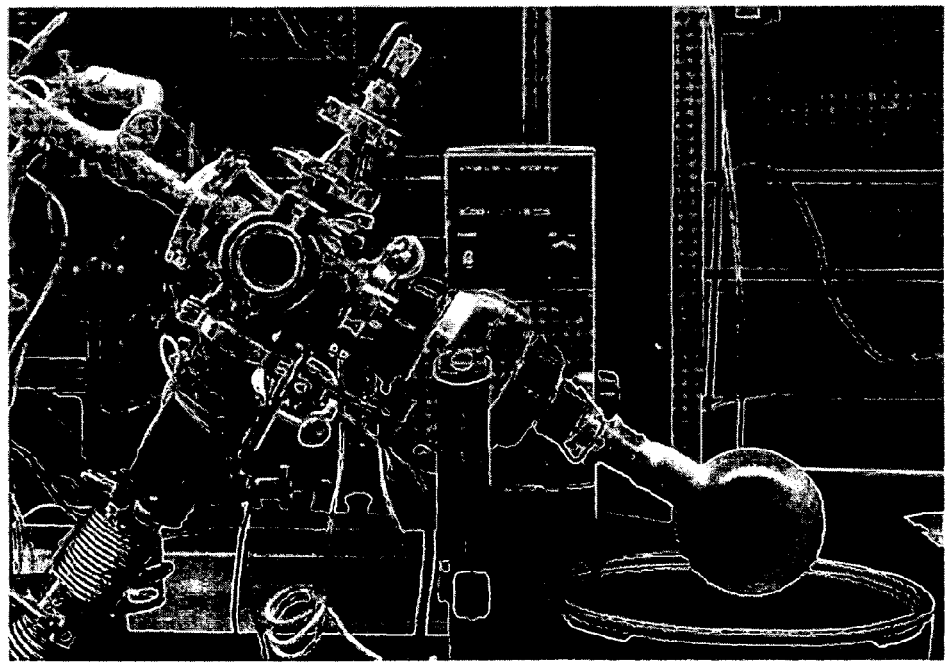
Figure 9:
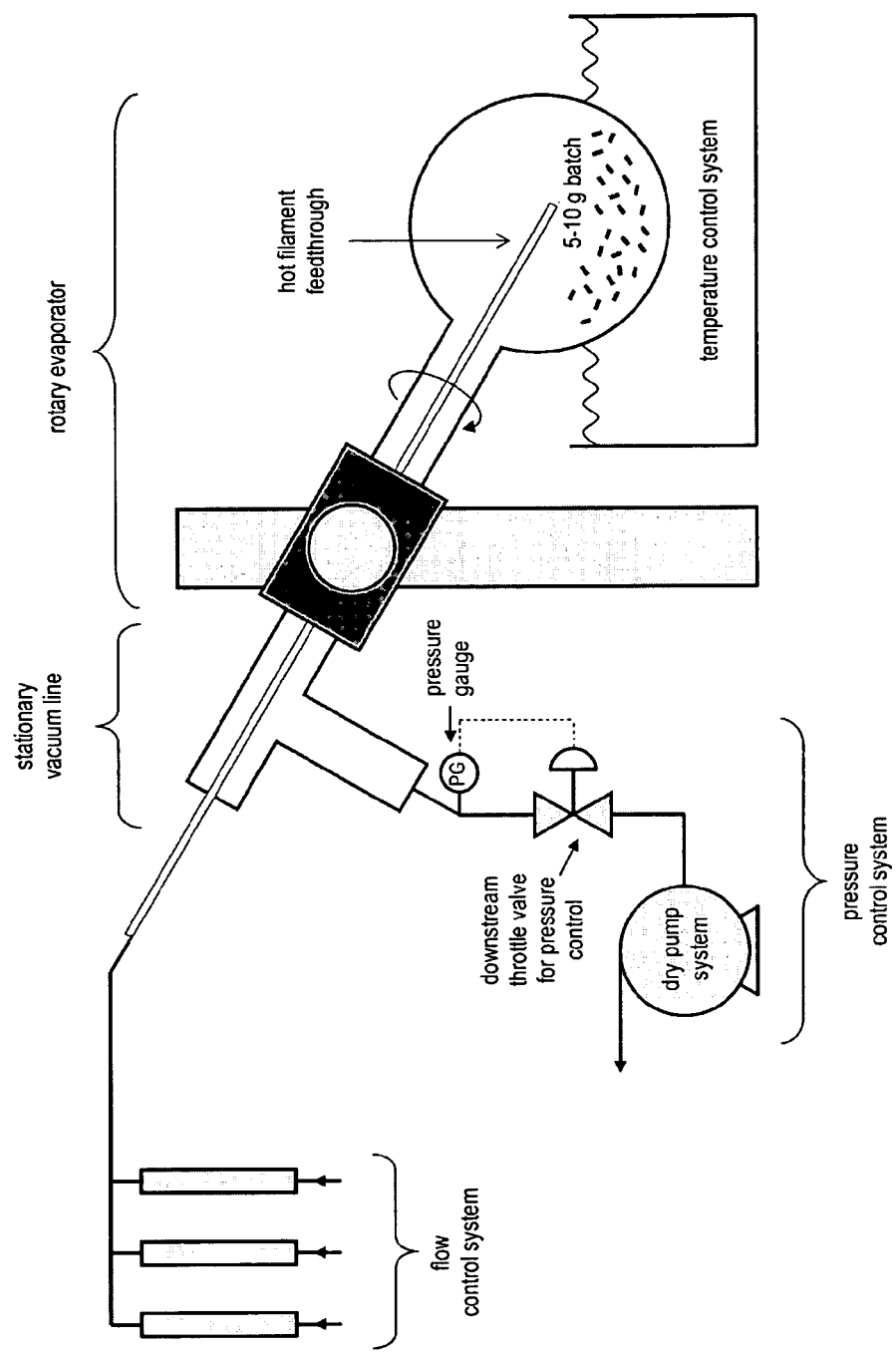
FIG. 9 depicts one embodiment of the iCVD apparatus.
Figure 10:
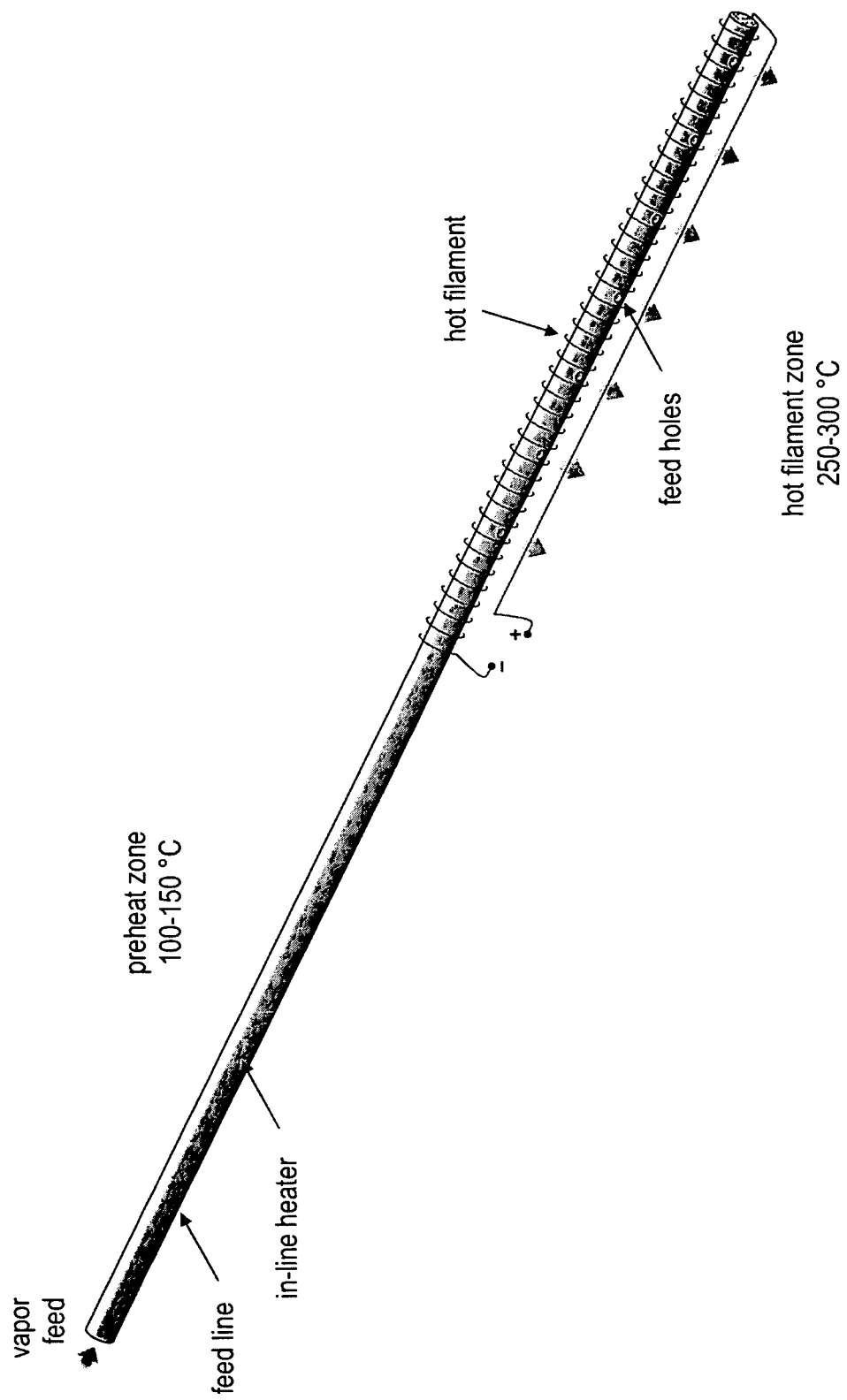
FIG. 10 depicts one embodiment of the inventive feedline, showing the preheat zone and the hot filament zone.

Remarkably, iCVD can alternatively be set up to allow particle agitation using a rotary mechanism to create a rotating particle bed. [For an example of a tumbler reactor being used for PECVD see Yasuda, H. Luminous Chemical Vapor Deposition and Interface Engineering. Marcel Dekker Incorp. 2004, 467-472.] FIGS. 8-10 show one embodiment of such a iCVD reactor; the reactor comprises of a modified rotary evaporator with two primary components. One component is a feedthrough attachment for directing vapors in and out, for controlling system pressure, and for electrical power to provide resistive heating to initiate polymerization. The other is a rotovap attachment that can rotate a flask containing, in one embodiment, up to about 10 g of particles to speeds of up to about 280 rpm. This rotary motion provides mechanical agitation for more uniform coating. The flask sits in a temperature-controlled water bath to keep the particles sufficiently cool to enhance vapor adsorption and promote surface polymerization. The reactor has a specially designed vapor feed line that consists of a stainless steel tube with an in-line sheathed heater to preheat and maintain the monomer and initiator as vapors. At the end of the feed line are evenly spaced exit holes for vapor entry into the flask; on exiting the holes the vapors will encounter a coiled filament wire that is resistively heated to activate the initiator; the activated initiator and monomer then adsorbs onto the particle surfaces where polymerization occurs (FIG. 10). The iCVD reactor has automated electronics to control reactor pressure using a downstream butterfly valve and to control reactant flow rates using calibrated mass flow controllers. Any unreacted vapors may be exhausted from the system through a roots blower-dry pump system (FIG. 9).

SELECTED iCVD CONDITIONS. The iCVD coating process can take place at a range of pressures from atmospheric pressure to low vacuum. In certain embodiment, a low operating pressure, typically in the range of about 10 Pa to about 100 Pa, can provide an ideal environment for the coating extremely fine objects. In certain embodiments, the pressure is less than about 1 torr; in yet other embodiments the pressure is less than about 0.7 torr or less than about 0.4 torr. In other embodiments the pressure is about 1 torr; or about 0.7 torr; or about 0.4 torr.

The flow rate of the monomer can be adjusted in the iCVD method. In certain embodiments the monomer flow rate is about 10 sccm. In other embodiments the flow rate is less than about 10 sccm. In certain embodiments the monomer flow rate is about 5 sccm. In other embodiments the flow rate is less than about 5 sccm. In certain embodiments the monomer flow rate is about 3 sccm. In other embodiments the flow rate is less than about 3 sccm. In certain embodiments the monomer flow rate is about 1.5 sccm. In other embodiments the flow rate is less than about 1.5 sccm. In certain embodiments the monomer flow rate is about 0.75 sccm. In other embodiments the flow rate is less than about 0.75 sccm. When more than one monomer is used (i.e. to deposit co-polymers), the flow rate of the additional monomers, in certain embodiments, may be the same as those presented above.

The flow rate of the initiator can be adjusted in the iCVD method. In certain embodiments the initiator flow rate is about 10 sccm. In other embodiments the flow rate is less than about 10 sccm. In certain embodiments the initiator flow rate is about 5 sccm. In other embodiments the flow rate is less than about 5 sccm. In certain embodiments the initiator flow rate is about 3 sccm. In other embodiments the flow rate is less than about 3 sccm. In certain embodiments the initiator flow rate is about 1.5 sccm. In other embodiments the flow rate is less than about 1.5 sccm. In certain embodiments the initiator flow rate is about 0.75 sccm. In other embodiments the flow rate is less than about 0.75 sccm.

The temperature of the filament can be adjusted in the iCVD method. In certain embodiments the temperature of the filament is about 350° C. In certain embodiments the temperature of the filament is about 300° C. In certain embodiments the temperature of the filament is about 250° C. In certain embodiments the temperature of the filament is about 245° C. In certain embodiments the temperature of the filament is about 235° C. In certain embodiments the temperature of the filament is about 225° C. In certain embodiments the temperature of the filament is about 200° C. In certain embodiments the temperature of the filament is about 150° C. In certain embodiments the temperature of the filament is about 100° C.

The iCVD coating process can take place at a range of temperatures. In certain embodiments the temperature is ambient temperature. In certain embodiments the temperature is about 25° C.; in yet other embodiments the temperature is between about 25° C. and 100° C., or between about 0° C. and 25° C. In certain embodiments said temperature is controlled by a water bath.

The iCVD coating process can take place at a range of flask rotating speeds. In certain embodiments said rotating speed is about 50 rpm. In certain embodiments said rotating speed is about 100 rpm. In certain embodiments said rotating speed is about 150 rpm. In certain embodiments said rotating speed is about 200 rpm. In certain embodiments said rotating speed is about 250 rpm. In certain embodiments said rotating speed is about 300 rpm. In certain embodiments said rotating speed is about 350 rpm.

In certain embodiments, typical reactor conditions are about 0.4 torr pressure, about 1.5 sccm monomer flow, about 0.2 sccm initiator flow, about 235° C. filament temperature, about 25° C. water temperature and about 150 rpm rotating speed.

In certain embodiments, the rate of polymer deposition is about 1 micron/minute. In certain embodiments, the rate of polymer deposition is between about 1 micron/minute and about 50 nm/minute. In certain embodiments, the rate of polymer deposition is between about 10 micron/minute and about 50 nm/minute. In certain embodiments, the rate of polymer deposition is between about 100 micron/minute and about 50 nm/minute. In certain embodiments, the rate of polymer deposition is between about 1 nm/minute and about 50 nm/minute. In certain embodiments, the rate of polymer deposition is between about 10 nm/minute and about 50 nm/minute. In certain embodiments, the rate of polymer deposition is between about 10 nm/minute and about 25 nm/minute.

SELECTED INITIATORS OF THE INVENTION. In certain embodiments, the gaseous initiator of the instant invention is selected from the group consisting of compounds of formula I:

$$A\text{-}X\text{—}B \qquad \qquad I$$

wherein, independently for each occurrence, A is hydrogen, alkyl, cycloalkyl, aryl, heteroaryl, aralkyl or heteroaralkyl; X is —O—O— or —N=N—; and B is hydrogen, alkyl, cycloalkyl, aryl, heteroaryl, aralkyl or heteroaralkyl.

In certain embodiments, the gaseous initiator of the instant invention is a compound of formula I, wherein A is alkyl. In certain embodiments, the gaseous initiator of the instant invention is a compound of formula I, wherein $R^4$ is hydrogen or alkyl. In certain embodiments, the gaseous initiator of the instant invention is a compound of formula I, wherein A is hydrogen. In certain embodiments, the gaseous initiator of the instant invention is a compound of formula I, wherein B is alkyl. In certain embodiments, the gaseous initiator of the instant invention is a compound of formula I, wherein X is —O—O—. In certain embodiments, the gaseous initiator of the instant invention is a compound of formula I, wherein X is —N=N—. In certain embodiments, the gaseous initiator of the instant invention is a compound of formula I, wherein A is —$C(CH_3)_3$; and B is —$C(CH_3)_3$. In certain embodiments, the gaseous initiator of the instant invention is a compound of formula I, wherein A is —$C(CH_3)_3$; X is —O—O—; and B is —$C(CH_3)_3$.

In certain embodiments, the gaseous initiator is selected from the group consisting of hydrogen peroxide, alkyl or aryl peroxides (e.g., tert-butyl peroxide), hydroperoxides, halogens and nonoxidizing initiators, such as azo compounds (e.g., bis(1,1-dimethyl)diazene).

Note that "gaseous" initiator encompasses initiators which may be liquids or solids at STP, but upon heading may be vaporized and fed into the chemical vapor deposition reactor.

SELECTED PARTICLES OF THE INVENTION. One aspect of this invention relates to coated particles and methods of coating them. In certain embodiments, coatings are provided onto the surfaces of various particulate materials. The size of the particles will depend somewhat on the particular material and the particular application. In certain embodiments, suitable particle sizes the nanometer range (e.g., about 0.001 µm to about 500 µm). In certain embodiments particle sizes range from about 0.005 µm to about 501 µm, or from about 0.1 µm to 10 µm, or from about 0.4 µm to about 10 µm. Particle size can also be expressed in terms of the surface area of the particles. In certain embodiments, particulate materials have surface areas in the range of about 0.1 $m^2$/g to 200 $m^2$/g.

A wide variety of particulate materials can be coated, with the composition of the uncoated particle and that of the coating typically being selected together so that the surface characteristics of the particle are modified in a way that is desirable for a particular application.

As used herein "particulate materials" include, for example, biologically active substances (see below), ceramics and glasses, such as fused silica, fumed silica, or soda glass; oxides such as silica, alumina, zirconia, ceria, yttria, and titania, as well as oxides of tin, indium and zinc and their doped forms (e.g., boron); carbides, such as tantalum carbide (TaC), boron carbide ($B_4C$), silicon carbide (SiC), tantalum carbide (TaC), boron carbide ($B_4C$), silicon carbide (SiC), titanium carbide (TiC); nitrides, such as titanium nitride (TiN) and boron nitride ($B_4N$); metals, such as gold (Au), silicon (Si), silver (Ag), platinum (Pi) and nickel (Ni); minerals, such as calcium fluoride ($CaF_2$) and quartz; semiconductors, such as silicon (Si), germanium (Ge), silicon carbide (SiC), cadmium telluride (CdTd) and gallium arsenide (GaAs); polymers, such as polystyrene, polymethylmethacrylalte and latex; carbon, such as graphite, fullerenes, nanotubes and diamond; magnetic particles; superconducting particles-quantum dots; fluorescent particles; colored or dyed particles, such as paints and toners; colloidal particles; microparticles; microspheres; microbeads; nanoparticles; nanospheres; nanorods; nanowires; shell particles; core particles; organic nanoparticles, such as dendrimers; or inorganic-organic hybrid nanoparticles, such as polyhedral silsesquioxanes.

Nanocrystalline Materials. Included here are ceramics, metals, and metal oxide nanoparticles. In the last two decades a class of materials with a nanometer-sized microstructure has been synthesized and studied. These materials are assembled from nanometer-sized building blocks, mostly crystallites. The building blocks may differ in their atomic structure, crystallographic orientation, or chemical composition. In cases where the building blocks are crystallites, incoherent or coherent interfaces may be formed between them, depending on the atomic structure, the crystallographic orientation, and the chemical composition of adjacent crystallites. In other words, materials assembled of nanometer-sized building blocks are microstructurally heterogeneous, consisting of the building blocks (e.g., crystallites) and the regions between adjacent building blocks (e.g., grain boundaries).

Carbon Nanotubes. Carbon nanotubes (CNTs) are hollow cylinders of carbon atoms. Their appearance is that of rolled tubes of graphite such that their walls are hexagonal carbon rings and are often formed in large bundles. The ends of CNTs are domed structures of six-membered rings capped by a five-membered ring. Generally speaking, there are two types of CNTs: single-walled carbon nanotubes (SWNTs) and multi-walled carbon nanotubes (MWNTs). As their names imply, SWNTs consist of a single, cylindrical graphene layer, where as MWNTs consist of multiple graphene layers telescoped about one another.

Dendrimers (Organic Nanoparticles). In recent years, a new structural class of macromolecules, the dendritic polymers, has attracted the attention of the scientific community. These nanometer sized, polymeric systems are hyperbranched materials having compact hydrodynamic volumes in solution and high, surface, functional group content. They may be water-soluble but, because of their compact dimensions, they do not have the usual rheological thickening properties that many polymers have in solution. Dendrimers, the most regular members of the class, are synthesized by step-wise convergent or divergent methods to give distinct stages or generations. Dendrimers are defined by their three components: a central core, an interior dendritic structure (the branches), and an exterior surface (the end groups). Over 50 compositionally different families of these nanoscale macromolecules, with over 200 end-group modifications, have been reported. [Dvornic, P. R. et al. *Polym. Prepr.* 1999, 40, 408.] They are characterized by nearly spherical structures, nanometer sizes, large numbers of reactive endgroup functionalities, shielded interior voids, and low systemic toxicity.

Polyhedral Silsesquioxanes (Inorganic-Organic Hybrid Nanoparticles). Hybrid inorganic-organic composites are an emerging class of new materials that hold significant promise. Materials are being designed with the good physical properties of ceramics and the excellent choice of functional group chemical reactivity associated with organic chemistry. New silicon-containing organic polymers, in general, and polysilsesquioxanes, in particular, have generated a great deal of interest because of their potential replacement for and compatibility with currently employed, silicon-based inorganics in the electronics, photonics, and other materials technologies. Hydrolytic condensation of trifunctional silanes yields network polymers or polyhedral clusters having the generic formula $(RSiO_{1.5})_n$. They are known as silsesquioxanes. Each silicon atom is bound to an average of one and a half (sesqui) oxygen atoms and to one hydrocarbon group (ane). Typical functional groups that may be hydrolyzed/condensed include alkoxy- or chlorosilanes, silanols, and silanolates.

The particulate is preferably non-agglomerated after the polymer is deposited. "Non-agglomerated" means that the particles do not form significant amounts of agglomerates during the process of coating the substrate particles with the inorganic material. Particles are considered to be non-agglomerated if (a) the average particle size does not increase more than about 5%, not more than about 2%, or not more than about 1% (apart from particle size increases attributable to the coating itself) as a result of depositing the coating, or (b) if no more than 2 weight %, or no more than 1 weight % of the particles become agglomerated during the process of depositing the polymeric material.

The ability to deposit the polymers without forming agglomerates is important. Gas transport mechanisms allow the reactants to diffuse to the surfaces of individual particles that are in contact so that individual particle surfaces can be coated, even if those particle surfaces are in contact with surfaces of other particles. This process is aided by particle agitation using a rotary mechanism, as described herein.

POLYMER and COPOLYMER COATINGS OF THE INVENTION. In certain embodiments the particles of the invention have an ultrathin coating. By "ultrathin" it is meant that the average thickness of the coating is, between about 0.001 nm and about 100 nm. In certain embodiments the average thickness of the coating is between about 0.001 nm and 50 nm. In certain embodiments, the average thickness of the coating is between about 0.001 nm and about 1 nm. In certain embodiments, the average thickness of the coating is from about 0.1 nm to about 50 nm; or from about 0.5 nm to about 35 nm; or from about 1 nm and about 10 nm. In certain embodiments, the ultrathin coating is conformal. By "conformal" it is meant that the thickness of the coating is relatively uniform across the surface of the particle, so that the surface shape of the coated particle closely resembles that of the uncoated particle. In other embodiments the ultrathin coating smoothes out deformities in the underlying particle.

As is true of the underlying particle, the composition of the coating can vary considerably depending on the composition of the underlying particle and the intended end-use of the coated particle. The coating may perform a variety of functions, depending on the nature of the base particle and the intended application. Thus, one function of the coating may be to modify the surface properties of the base particle. Another possible function of the coating involves the case where a base particle has a surface that behaves in some undesirable way in a particular environment. Alternately, the coating may itself be a reagent or catalyst in some chemical reaction. In these cases, this invention provides a convenient method of providing a high surface area reactive or catalytic material, and/or provides a way for finely dispersing the coating material.

In certain embodiments, the polymer or co-polymer comprises one or more recurring monomeric units selected from the group consisting of

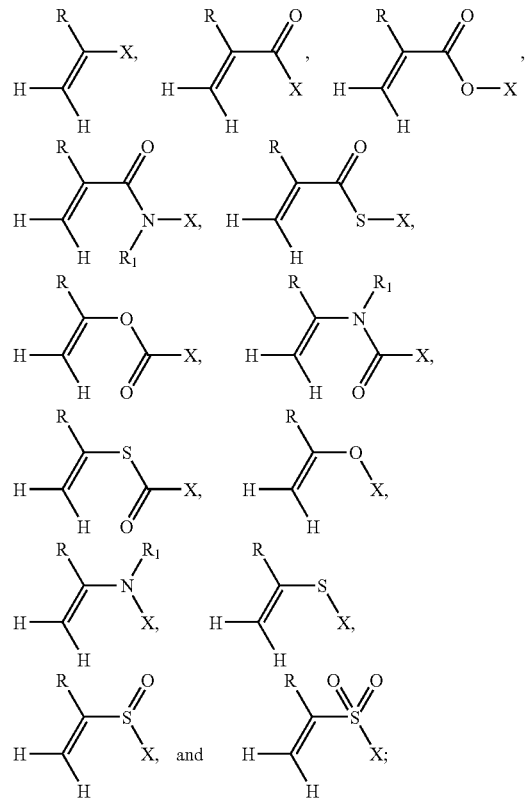

wherein, independently for each occurrence: R is selected from the group consisting of hydrogen and alkyl; $R^1$ is selected from the group consisting of hydrogen, alkyl, aralkyl, heteroaralkyl, and carboxyl; X is selected from the group consisting of hydrogen, alkyl, cycloalkyl, heteocycloalkyl, aryl, heteroaryl, aralkyl, heteoaralkyl, and —$(CH_2)_n$Y; Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido; and n is 1-10 inclusive. The term "copolymer" as used herein means a polymer of two or more different monomers.

In certain embodiments, the polymer or co-polymer comprises one or more recurring monomeric units selected from the group consisting of poly(glycidyl methacrylate), p-bromophenyl methacrylate, pentabromophenyl methacrylate, n-vinyl carbazole, p-divinyl benzene, styrene, alpha methyl styrene, 2-chlorostyrene, 3-chlorostyrene, 4-chlorostyrene, 2,3-dichlorostyrene, 2,4-dichlorostyrene, 2,5-dichlorostyrene, 2,6-dichlorostyrene, 3,4-dichlorostyrene, 3,5-dichlorostyrene, 2-bromostyrene, 3-bromostyrene, 4-bromostyrene, 2,3-dibromostyrene, 2,4-dibromostyrene, 2,5-dibromostyrene, 2,6-dibromostyrene, 3,4-dibromostyrene, 3,5-dibromostyrene, methyl acrylate, n-butyl acrylate, n-pentyl acrylate, n-hexyl acrylate, n-heptyl acrylate, n-octyl acrylate, 2-ethylhexyl acrylate, perfluorocyclohexylmethyl acrylate, benzyl acrylate, 2-hydroxyethyl acrylate, dimethylaminoethyl acrylate, Et$_3$DMAA (N,N-dimethylacetoacetamide), sec-butyl acrylate, tert-butyl acrylate, isobornyl acrylate, ethylene glycol diacrylate, methyl methacrylate, ethyl methacrylate, n-propyl methacrylate, n-butyl methacrylate, isobutyl methacrylate, n-pentyl methacrylate, n-hexyl methacrylate, n-heptyl methacrylate, sec-butyl methacrylate, tert-amyl methacrylate, t-butyl methacrylate, dimethylaminoethyl methacrylate, hydroxyethyl methacrylate, cyclohexyl methacrylate, benzyl methacrylate, isobornyl methacrylate, glycidyl methacrylate, ethylene glycol dimethacrylate, methacrylic acid, styrene, alpha-methyl styrene, ortho-methyl styrene, meta-methyl styrene, para-methyl styrene, para-ethyl styrene, 2,4-dimethyl styrene, 2,5-dimethyl styrene, m-divinylbenzene, p-divinylbenzene, vinylimidazole, N-vinyl-2-pyrrolidone, V3D3 (3901-77-7), 1,4-divinyloxybutane (3891-33-6), diethylene glygol divinyl ether (764-99-8), 1,5-hexadiene-3,4-diol DVG (1069-23-4), methyl trans-cinnamate, N-morpholinoethyl acrylate, 2-morpholinoethyl methacrylate, 2-isocyanatoethyl methacrylate, 2-sulfoethyl methacrylate, 2-methoxyethyl methacrylate, 2-(tert-butylamino)ethyl methacrylate, 2-ethoxyethyl methacrylate, 2-chloroethyl methacrylate, 2-hydroxypropyl methacrylate, 2-diethylaminoethyl methacrylate, cyclopentyl methacrylate, 2-(diisopropylamino) ethyl methacrylate, 2-bromoethyl methacrylate and 2-phenylethyl methacrylate.

SELECTED CROSSLINKERS OF THE INVENTION. In certain embodiments the inventive polymer or co-polymer coatings are crosslinked. A suitable crosslinker, if present, is, for example, a low molecular weight di- or polyvinylic crosslinking agent such as ethyleneglycol diacrylate or dimethacrylate, di-, tri- or tetraethylen-glycol diacrylate or dimethacrylate, allyl (meth)acrylate, a C$_2$-C$_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol diacrylate or dimethacrylate, methylene bisacrylamide or methylene bismethacrylamide, ethylene bisacrylamide or ethylene bismethacrylamide, and triallyl phthalate or diallyl phthalate. In certain embodiments, the crosslinker according to the invention is ethyleneglycol-dimethacrylate or ethyleneglycol-diacrylate.

Figure 15:
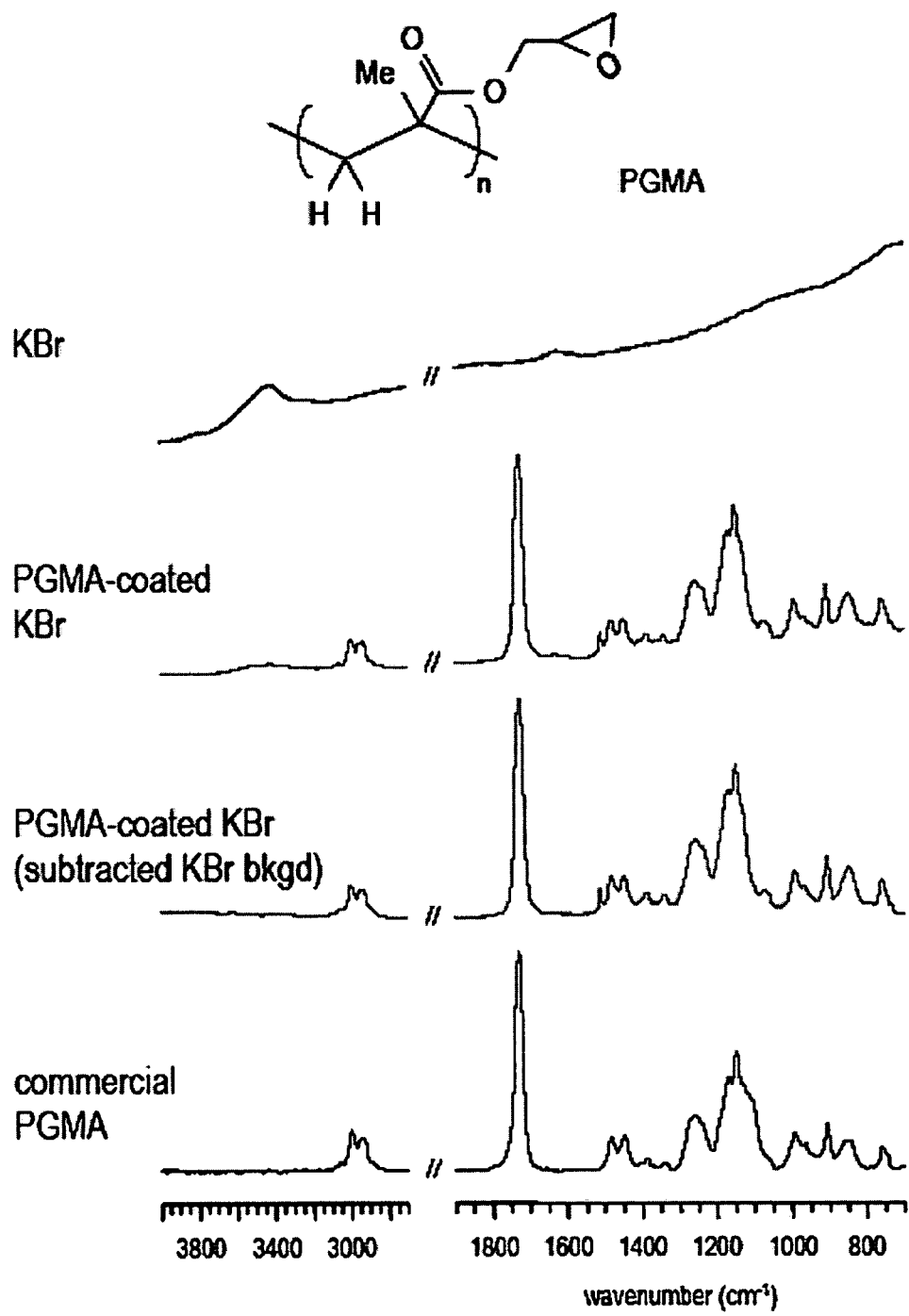
FIG. 15 depicts FTIR spectra of uncoated KBr, PGMA-coated KBr, the PGMA coating and conventional PGMA, demonstrating iCVD is able to produce polymers that are well-defined.
Figure 16:
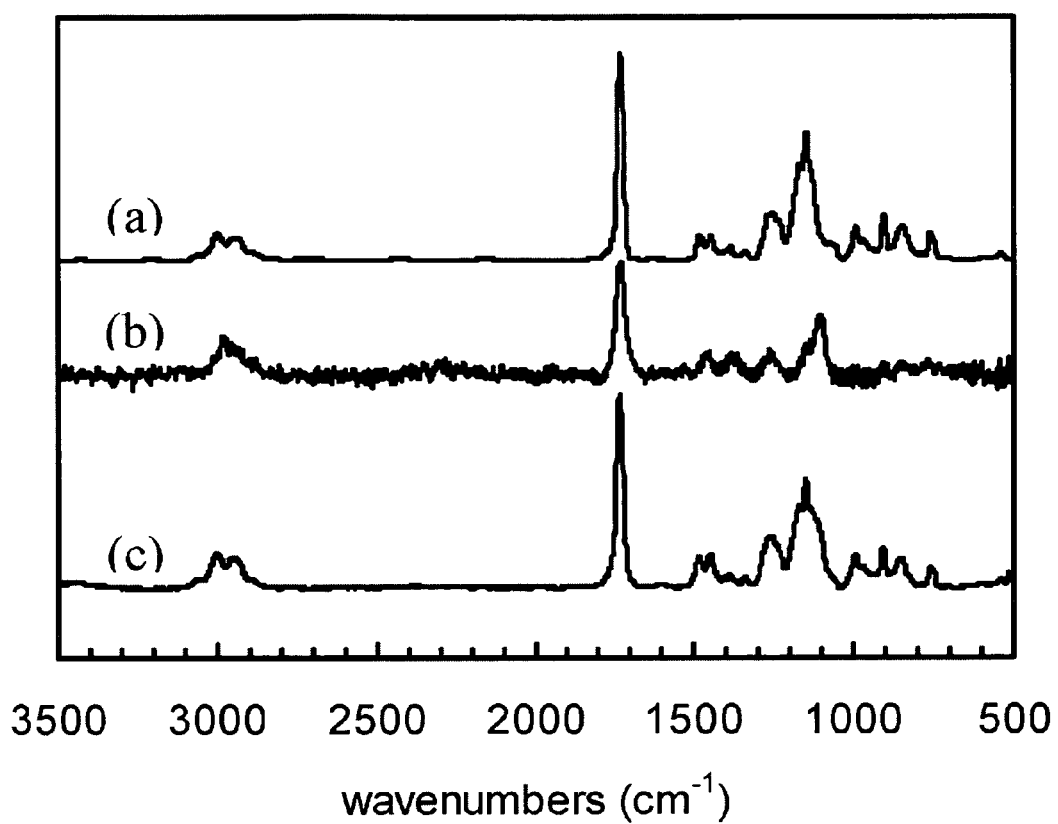
FIG. 16 depicts FTIR spectra of (a) PGMA film synthesized from hot filament CVD, (b) film deposited from low-power plasma enhanced CVD of GMA, and (c) conventionally polymerized PGMA. The adsorption peaks at 907, 848, and 760 cm$^{-1}$ are assigned to the characteristic adsorption bands of the epoxide group.
Figure 17:
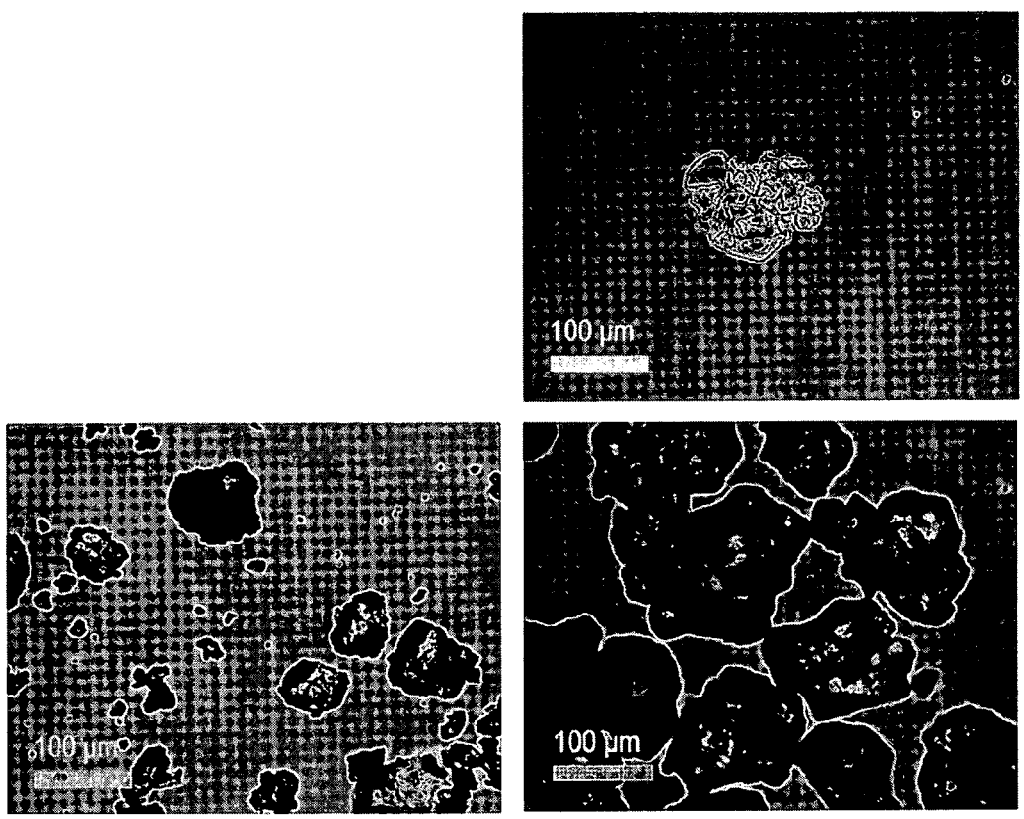
FIG. 17 depicts OM images of KBr particles before coating (bottom left) and after coating (bottom right), and of a PGMA shell after the KBr core was dissolved away with water (top right).

ENCAPSULATION OF NANOPARTICLES. To demonstrate that the iCVD reactor can encapsulate particles with polymers, an iCVD coating run was performed on KBr (potassium bromide) particles. KBr is infrared-transparent and therefore is amenable to coating analysis using Fourier transform infrared (FTIR) spectroscopy. Further, dissolution of the coated KBr particles in water after deposition will allow the coating to be visually observed through optical microscopy (OM). In one embodiment, glycidyl methacrylate was used as the monomer and tert-amyl peroxide was the initiator to form polyglycidyl methacrylate (PGMA). FIG. 15 shows the FTIR spectra comparing the PGMA coating on the KBr to conventional PGMA, demonstrating that iCVD produces polymers that are spectroscopically identical to those prepared through solution phase synthesis routes. Comparison with FIG. 16b, which depicts the PECVD GMA, demonstrates the superiority of the iCVD technique, as evidenced by the extent of decomposition present in the PECVD film. [Mao, Y.; Gleason, K. K. Hot Filament Chemical Vapor Depositon of Poly(glycidylmethacrylte) Thin Films Using tert-Butyl Peroxide as an Initiator. *Langmuir* 2004, 20, 2484-2488.] FIG. 17 shows OM images of the KBr particles before and after coating, demonstrating no agglomeration. FIG. 17 also shows clearly an image of the PGMA shell after dissolution of the KBr core.

Figure 18:
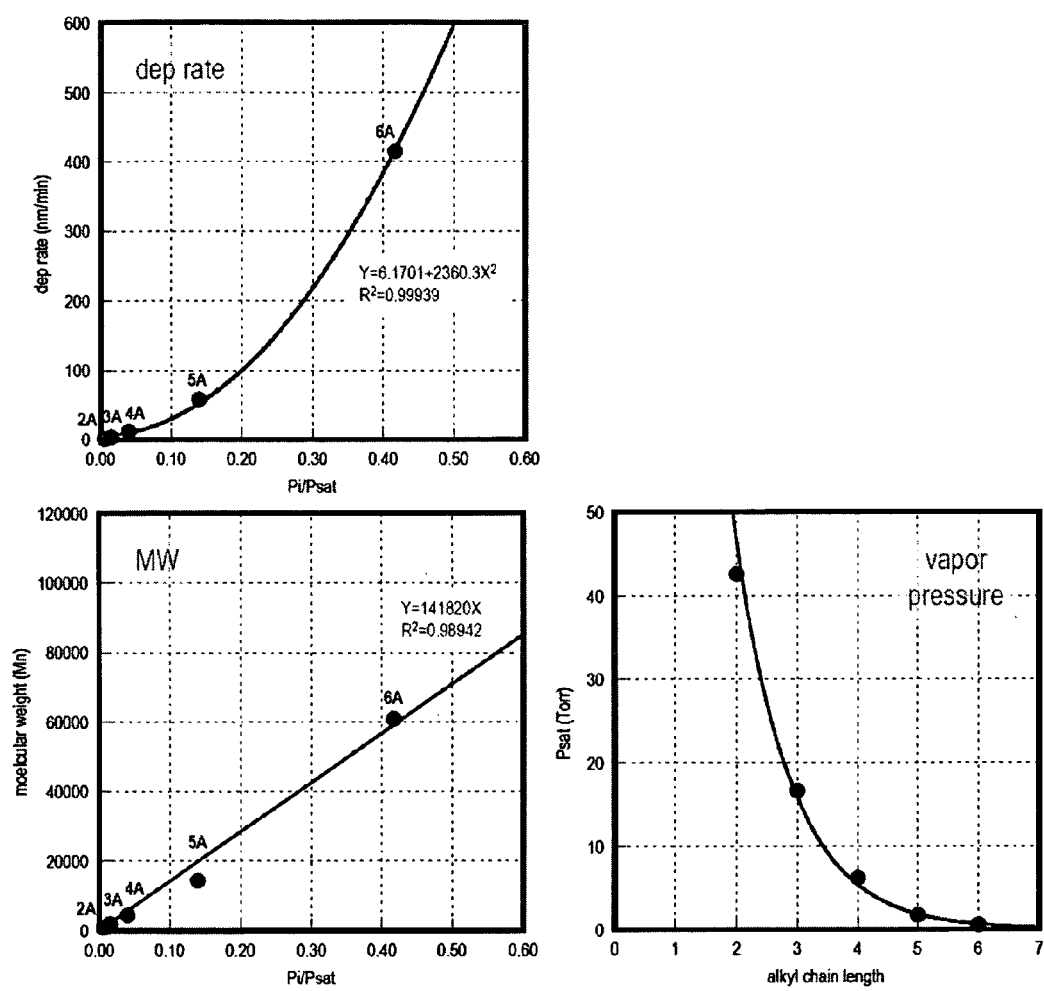
FIG. 18 depicts the effect of monomer volatility on deposition rate and molecular weight.
Figure 19:
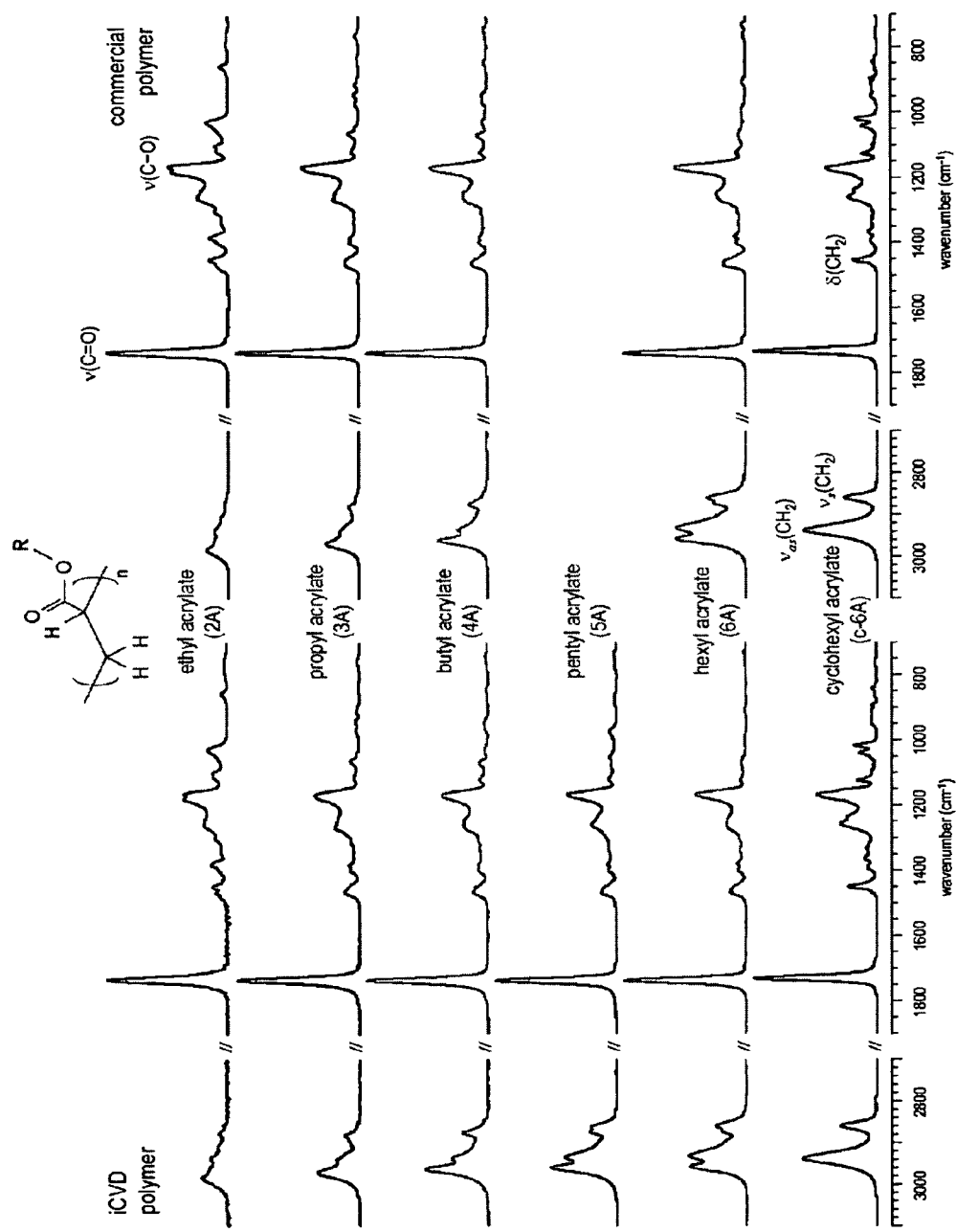
FIG. 19 depicts FTIR spectra of polyalkyl acrylates comparing iCVD and conventional polymers.

To investigate more fundamentally the iCVD polymerization process, three process parameters—monomer volatility, monomer concentration and particle size—were systematically studied to look at their effect on process kinetics. To vary monomer volatility, a series of alkyl acrylates with increasing alkyl chain length was used. It was found that the deposition rate has a second-order dependence on the ratio of monomer partial pressure to monomer vapor pressure ($P_f/P_{sat}$), this ratio effectively gives the surface concentration of the monomer if a linear adsorption behavior is assumed (see FIG. 18 for plot). This suggests that iCVD kinetics are strongly surface-driven, that as the monomer pressure approaches its saturated vapor pressure, polymerization is significantly increased. There is a corresponding linear increase in the molecular weight, as determined by gel permeation chromatography (GPC), with increase in $P_f/P_{sat}$. FTIR spectra (see FIG. 19 for plot) of these polyalkyl acrylates reveal that they are extremely clean and are spectroscopically identical to commercial polymers made by solution techniques.

Figure 20:
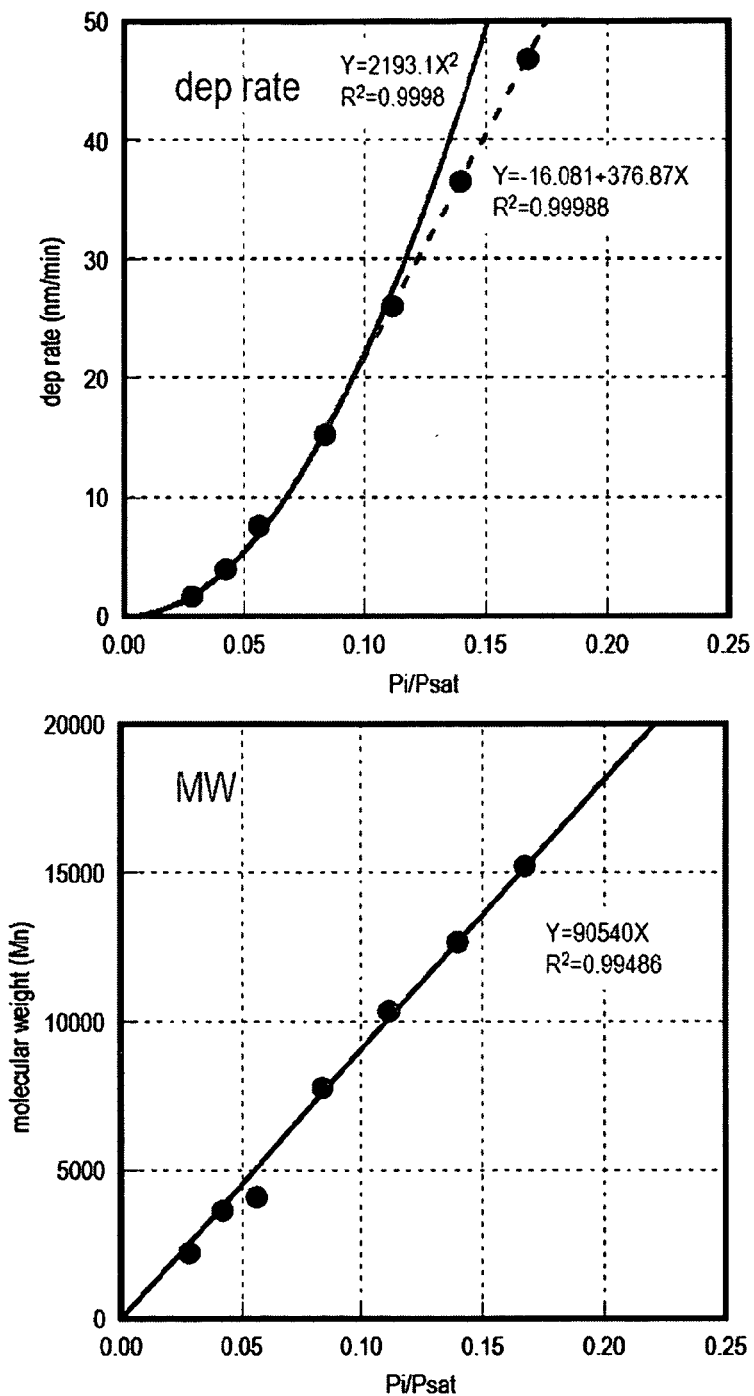
FIG. 20 depicts the effect of monomer (butyl acrylate) concentration on deposition rate and molecular weight.

To vary monomer concentration, butyl acrylate (n=4) was used together with argon as the diluent to alter the partial pressure of the monomer while keeping the total pressure and flowrates constant. At low $P_f/P_{sat}$ ratios, there is a second order dependence of deposition rate on surface monomer concentration, while at higher $P_f/P_{sat}$ ratios, the dependence becomes linear (see FIG. 20 for plot). On the other hand, molecular weight only showed a linear increase with surface monomer concentration. These kinetic phenomena can be explained with conventional radical polymerization kinetics and are similar to that observed in bulk or solution polymerization (see *Principles of Polymerization*, G. Odian).

Figure 2:
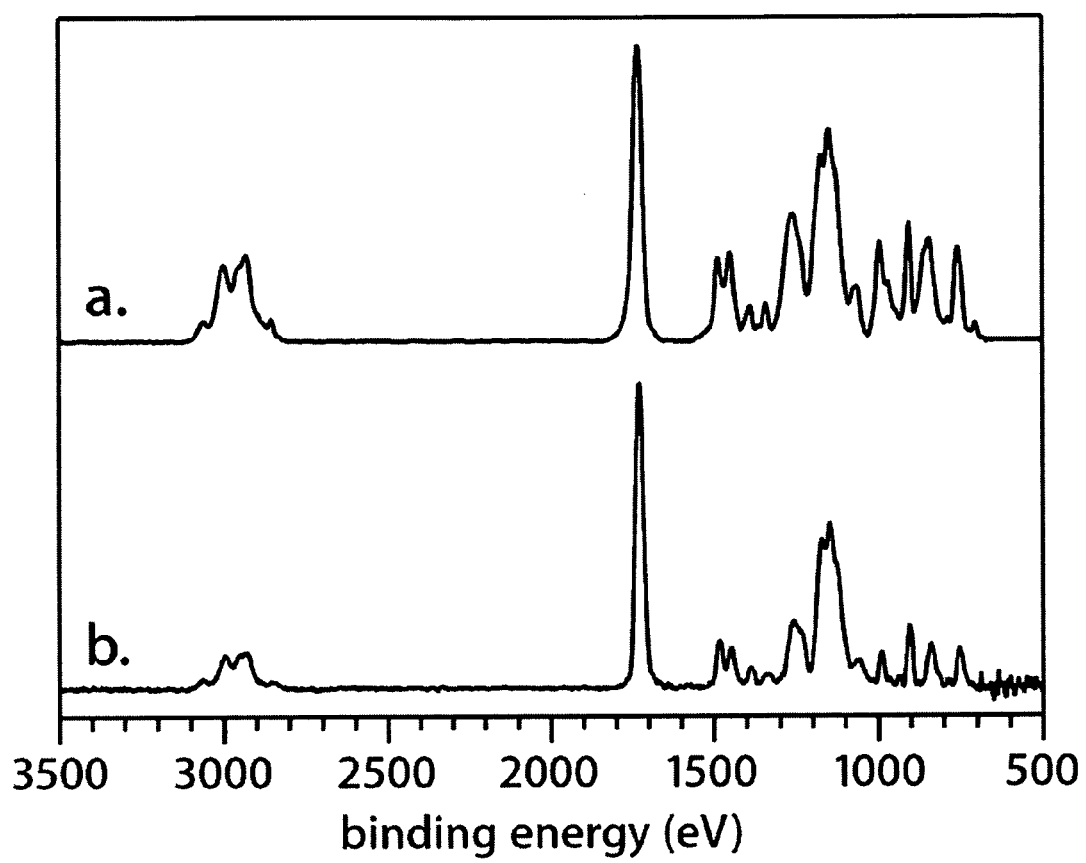
FIG. 2 depicts the characterization of coating on carbon nanotubes: (a) Fourier transform infrared spectroscopy (FTIR) of a PGMA polymer standard ($M_n$=11,000, $M_w$=12,700); and (b) FTIR of PGMA-coated carbon nanotubes, showing excellent match with the polymer standard. Peak at 1727 cm$^{-1}$ is characteristic of the carbonyl on methacrylates, and peaks at 905 and 841 cm$^{-1}$ are characteristic of the glycidyl group.

FIG. 1 shows that particles down to the nanoscale, such as carbon nanotubes, can be individually encapsulated with a polymer. Using glycidyl methacrylate as the monomer and tert-amyl peroxide as the initiator, both conventional reactants in polymerization chemistries, poly(glycidyl methacrylate) (PGMA) can be formed on the surface of the particles by thermally activating the initiator in the gas phase through an array of electrically heated wires at a temperature of about 250° C. to about 300° C. and promoting surface adsorption of activated species and the monomer vapor on the particles through contact with a cooled stage at a temperature between about 20° C. to about 30° C. Shown in FIG. 1a are multiwalled carbon nanotubes (about 20 nm to about 50 nm in diameter, about 5μm to about 20μm in length) prior to iCVD coating. As evident in FIG. 1b, after iCVD treatment, the PGMA coating is seen under transmission electron microscopy (TEM) to encapsulate each nanotube, with a coating thickness on the order of 25 nm. Significantly, iCVD is able to handle asymmetric particles with high aspect ratios, which for these nanotubes are between about 1,000 to about 10,000 in length-to-diameter. This size disparity keeps the nanotubes relatively unaggregated to begin with so that even without any physical agitation of the particles during the coating process, conformal coatings around individual nanotubes can be made. At points where the nanotubes contacted each other or were in close proximity with each other, the coating encapsulates multiple tubes but iCVD did not appear to cause additional aggregation. Using Fourier transform infrared spectroscopy (FTIR), the structure of the PGMA polymer can be easily probed as the nanotubes themselves are relatively non-absorbing in the infrared region. Comparing the FTIR spectrum of a PGMA standard with that of the PGMA-coated nanotubes in FIGS. 2a and 2b, there is a good match in the spectral signatures, with the presence of the strong carbonyl peak characteristic of a methacrylate at 1727 cm$^{-1}$, and the peaks specific to the oxirane ring of the glycidyl group at 905 and 841 cm$^{-1}$, representing the asymmetric and symmetric in-plane ring deformation modes, respectively. [Paul, S. & Ranby, B. Determination of epoxy side groups in polymers: Infrared analysis of methyl methacrylate-glycidyl methacrylate copolymers. *Anal. Chem.* 47, 1428-1429 (1975); and Bussi, P. & Ishida, H. Partially miscible blends of epoxy-resin and epoxidized rubber: Structural characterization of the epoxidized rubber and mechanical properties of the blends. *J. Appl. Polym. Sci.* 53, 441-454(1994).] iCVD provides a useful way to surface functionalize nanotubes in a non-covalent fashion without destroying the sp$^2$ nature of the nanotubes, which will help preserve their properties, such as electrical conductivity and tensile stiffness.

Figure 3:
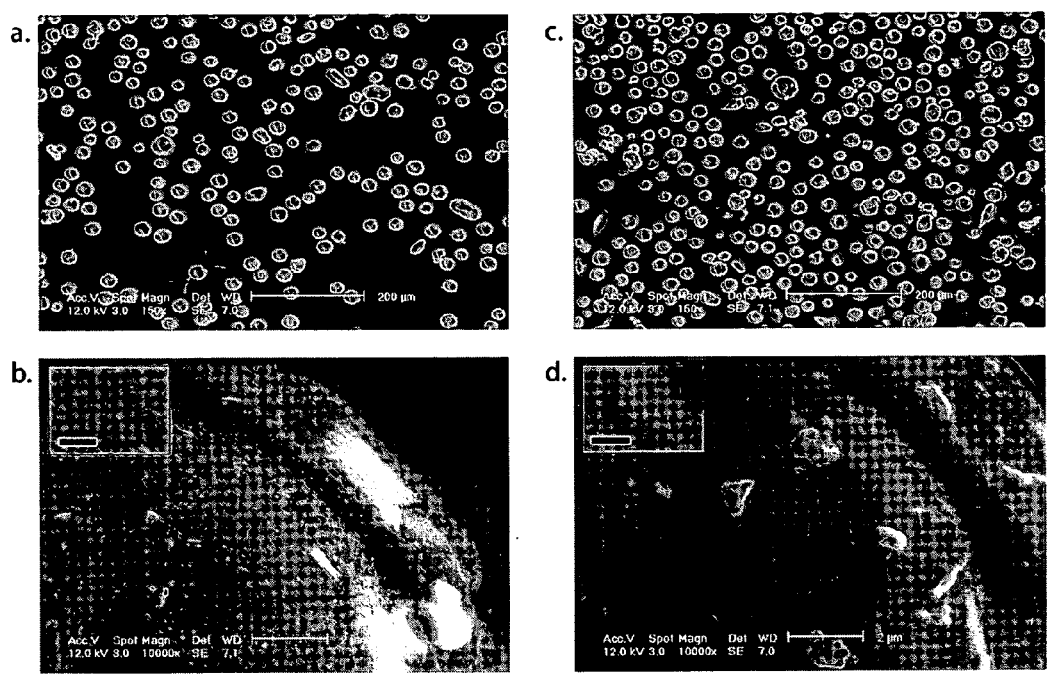
FIG. 3 depicts the encapsulation of glass microspheres: (a) SEM of uncoated microspheres, 25-32 μm in diameter, with an average diameter of 28.5 μm and density of 2.46 g/cm$^3$; (b) SEM at a higher magnification, revealing a grainy surface morphology before coating (inset scalebar=500 nm); (c) SEM of PGMA-coated microspheres, showing no agglomeration after iCVD; and (d) SEM at a higher magnification, showing the coating has made the surface smoother (inset scalebar=500 nm).

ENCAPSULATION OF MICROPARTICLES. Aside from carbon nanotubes, symmetric particles like microspheres have also been successfully encapsulated using the iCVD approach. Microspheres are an important area of particle technology and engineering. Microspheres that incorporate peptides and proteins are now being used as extended-release agents in drug delivery. [Okada, H. One- and three-month release injectable microspheres of the LH-RH superagonist leuprorelin acetate. *Adv. Drug Deliv. Rev.* 28, 43-70 (1997); and Cleland, J. L., Johnson, O. L., Putney, S. & Jones, A. J. S. Recombinant human growth hormone poly(lactic-co-glycolic acid) microsphere formulation development. *Adv. Drug Deliv. Rev.* 28, 71-84 (1997).] Microspheres are also being explored as optical powders and in photonics. [Deumié, C., Voarino, P. & Amra, C. Overcoated microspheres for specific optical powders. *Appl. Opt.* 41, 3299-3305 (2002); Arnold, S. Microspheres, photonic atoms and the physics of nothing. *Am. Sci.* 89, 414-421 (2001).] FIG. 3 shows glass microspheres viewed under scanning electron microscopy (SEM) which have undergone iCVD encapsulation with PGMA, this time using a rotating bed to physically agitate the particles. The glass microspheres remain unagglomerated after the coating process when comparing FIG. 3a with FIG. 3c. These microspheres which have an average diameter of 28.5 μm are much smaller than the 100 μm limit below which liquid spray coating will usually cause significant particle agglomeration. Although the thinness of the coating makes it visually hard to discern through SEM, a similar comparison at a higher magnification between FIGS. 3b and 3d shows that the PGMA coating appears to have reduced the grainy surface morphology inherent in the uncoated microspheres. Unlike methods that adsorb polymers onto particle surfaces, iCVD allows the polymer to form directly at the particle surface making it more likely to obtain a more conformal and smoother encapsulating shell than would be possible with layering a pre-formed polymer that often requires glidants, plasticizers and heat to enable the polymer to flow and amalgamate into a continuous coating.

Figure 4:
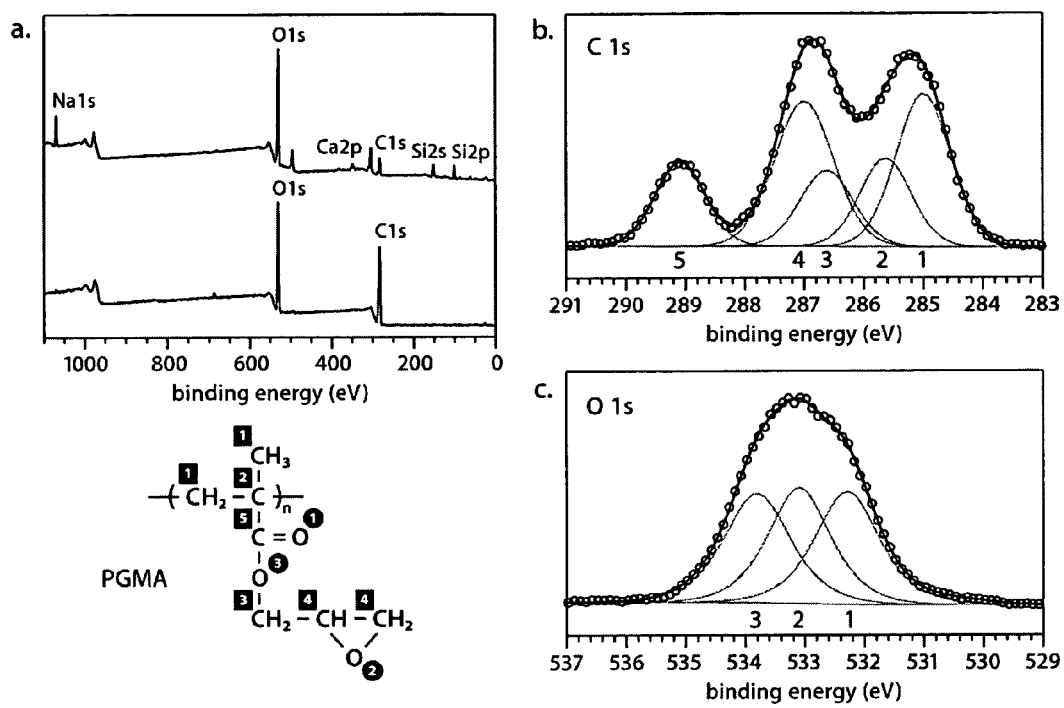
FIG. 4 depicts the characterization of coating on microspheres: (a) XPS surveys of uncoated (top) and PGMA-coated (bottom) microspheres where the sodalime composition of the glass is completely replaced by the PGMA composition of the polymer after iCVD; (b) $C_{1s}$ XPS of coated spheres and the five fitted component peaks as assigned; and (c) O15×PS of coated spheres and the three fitted component peaks as assigned. Peak fitting results yield a close match with that of stoichiometric PGMA.

The composition of the PGMA coating on the glass microspheres was analyzed using X-ray photoelectron spectroscopy (XPS) as depicted in FIG. 4. Survey spectra before and after iCVD (FIG. 4a) reveal the loss of peaks associated with the soda-lime composition of the pristine microspheres and the appearance of the peaks related to the PGMA polymer, indicating that the microspheres are completely covered by the polymer. By fitting component peaks to the high-resolution C$_{1s}$ and O$_{1s}$ spectra (FIGS. 4b and 4c), the resulting coating agrees well with the expected stoichiometry for PGMA. There are five distinct carbon environments for PGMA which are resolvable by XPS. Stoichiometry dictates that the five carbon sites are in the ratio C1:C2:C3:C4:C5=2:1:1:2:1 (see FIG. 4 for assignments). Actual XPS data yield a ratio C1:C2:C3:C4:C5=1.976:1.077:0.961:2.021:1.001, which is in good agreement with a clean PGMA composition. Likewise, there are three resolvable oxygen sites for PGMA. Stoichiometry requires a ratio O1:O2:O3=1:1:1 and actual data gives a ratio O1:O2:O3=0.977:0.977:0.977, which is also in good agreement with a stoichiometric PGMA polymer. iCVD is thus able to produce extremely well-defined polymer compositions necessary for precise surface engineering. By choosing the appropriate iCVD polymerization chemistry, specific functional groups can be incorporated onto the particle surface simply through the functionality of the polymer encapsulating layer.

Figure 5:
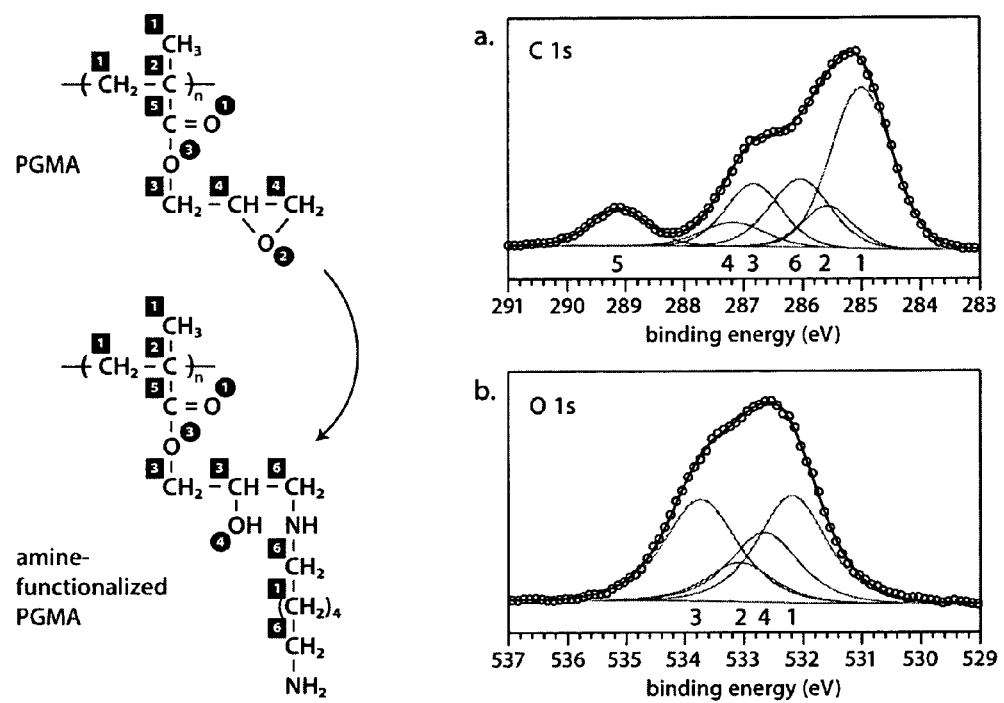
FIG. 5 depicts the immobilization of hexamethylenediamine: (a) $C_{1s}$ XPS of amine-functionalized PGMA-coated microspheres. The additional peak is assigned to the carbons adjacent to the amines; and (b) O15×PS of amine-functionalized PGMA-coated microspheres. The additional peak is assigned to the β-hydroxyl group formed as a result of the oxirane ring opening reaction. Peak fitting results indicate a 65% conversion of the oxirane rings to the amine.

SURFACE IMMOBILIZATION ON MICROPARTICLES. Additionally, after surface encapsulation of particles, surface design can be tailored by subsequently binding desired functional groups onto the polymer coating. In one embodiment, using PGMA as the polymer shell, the presence of the oxirane ring affords the binding of target molecules through a ring-opening reaction. The oxirane ring is susceptible to nucleophilic attack by a primary amine, sulfhydryl or hydroxyl group to form a secondary amine, thioether or ether bond, respectively, together with a β-hydroxyl group from the opened ring. [Hermanson, G. T. in *Bioconjugate Techniques* 142 (Academic Press, San Diego, Calif., 1996).] This nucleophilic attack is typically enhanced under basic aqueous pH conditions or through the use of a protic solvent like ethanol. FIG. 5 shows the XPS results after soaking PGMA-coated glass microspheres in a 0.5 M hexamethylenediamine solution in ethanol at 60° C. for 5 h. Both the C$_{1s}$ and O$_{1s}$ spectra reveal new bonding environments, attributed to carbons adjacent to the amines and to oxygen of the β-hydroxyl groups (see FIG. 5 for assignments), demonstrating that binding has occurred although there is still a presence of the oxirane ring. Peak fitting calculations indicate that 65% of the glycidyl groups have been converted to the amine. This post-encapsulation immobilization step provides another way to design particle surfaces with the desired functionality or active site.

Figure 6:
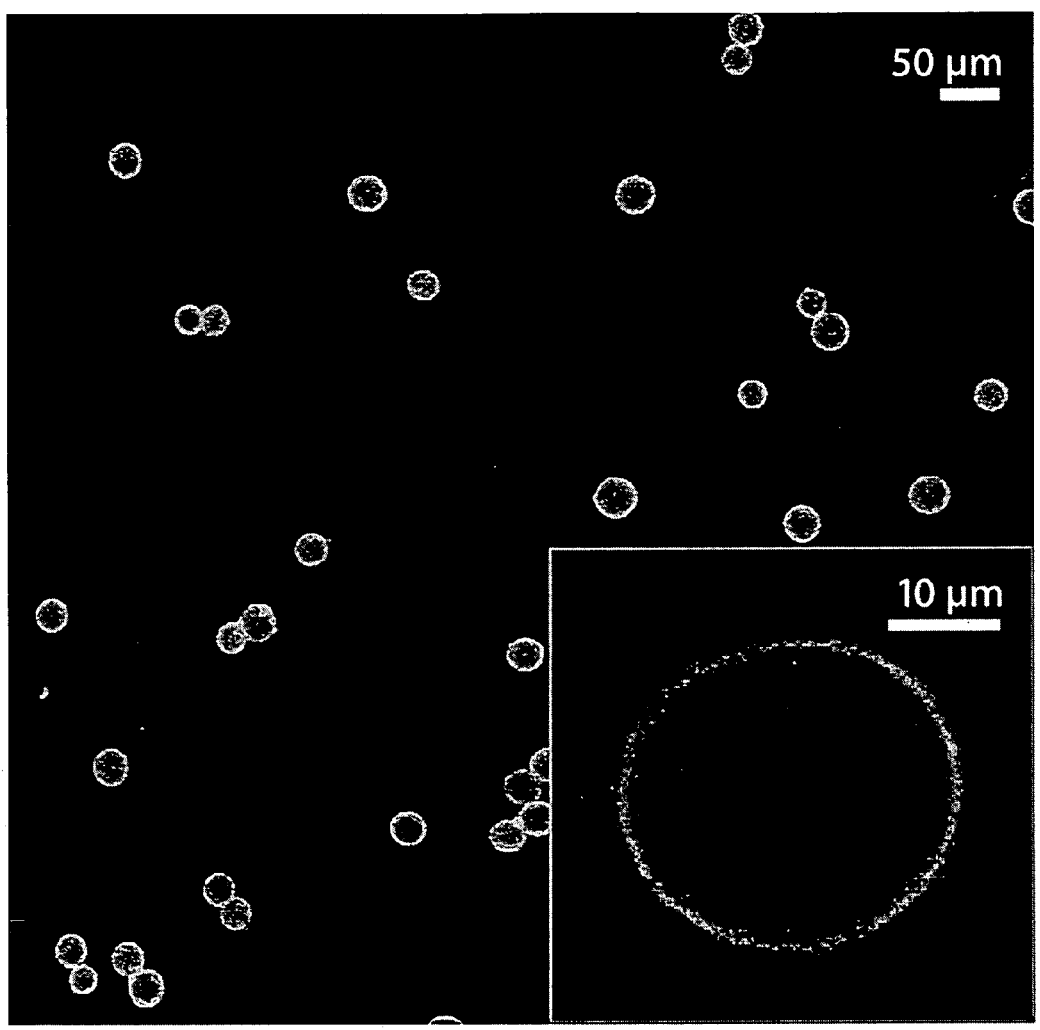
FIG. 6 depicts the immobilization of fluorescein-5-thiosemicarbazide: CLSM of PGMA-coated microspheres after reaction with the amine-containing fluorescent label. The fluorescent ring around each particle suggests circumferentially uniform binding around a stable coating. Thickness of the ring suggests binding across the depth of the coating. CLSM of uncoated microspheres subjected to the same immobilization protocol gave no fluorescence.

In another embodiment, fluorescent markers can be immobilized onto PGMA-coated microspheres simply by coupling an amine-containing fluorescent molecule, such as fluorescein-5-thiosemicarbazide (FTSC), to the oxirane ring of the glycidyl group. The labeled microspheres would be observable as fluorescent rings under confocal laser scanning microscope (CLSM). FIG. 6 shows CLSM images of PGMA-encapsulated microspheres which have been treated with a FTSC solution in pH 8.0 phosphate buffer at 60° C. for 5 h. The fluorescently green ring around each particle confirms that binding of the fluorescent marker to the PGMA is achieved. As expected, a negative control of uncoated microspheres that underwent the same treatment gave no fluorescence under CLSM (not shown). The 0.5 μm resolution of the microscope prevents an accurate measurement of coating thickness on thin coatings. Further, it is unclear how far the binding reaction can penetrate through the coating, although similar binding experiments on flat substrates suggest that immobilization takes place across the entire thickness for such thin coatings. [Edmondson, S. & Huck, W. T. S. Controlled growth and subsequent chemical modification of poly(glycidyl methacrylate) brushes on silicon wafers. *J. Mater. Chem.* 14, 730-734 (2004).] An estimate of the coating thickness from the CLSM images is on the order of about 500 nm, which is the resolution limit of the instrument. A calibrated analysis using gel permeation chromatography (GPC) of the PGMA polymer dissolved from these microspheres suggests a thickness of 135 nm (see Exemplification). Although the immobilization examples described here have been performed in the solution phase, no agglomeration is observed upon drying presumably because the chemistries involved small molecules in a non-solvent system of the PGMA so any liquid bridges that form are insufficient to cause any significant binding. It is conceivable that immobilization after polymer encapsulation could also be done in a dry state through the use of amine vapors instead. In this way, the entire surface design concept becomes completely dry.

COATING BIOLOGICALLY ACTIVE SUBSTANCES. In certain embodiments, the particles to be coated can be biologically active substances. The biologically active substance of the invention can vary widely with the purpose for the composition. The active substance(s) may be described as a single entity or a combination of entities. The delivery system is designed to be used with biologically active substances having high water-solubility as well as with those having low water-solubility to produce a delivery system that has controlled release rates. The term "biologically active substance" includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of broad categories of useful biologically active substances include the following therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, and prodrugs. More specifically, non-limiting examples of useful biologically active substances can be found in Mao, Hai-Quan et al. U.S. Pat. No. 6,600,010, hereby incorporated by reference.

Enteric coatings. Encapsulation of drugs with synthetic polymers is one effective means to introduce temporal or target control over drug delivery. The polymer shell may act as a diffusion membrane for a timed release of the drug from the core or as a protective barrier that disintegrates in a specific region within the body for a targeted release. The polymer coating may also act to mask any undesirable taste of orally dispensed drugs. Further, the polymer coating may act as a protective layer from moisture to prolong the shelf life of the drug.

With enteric coatings, the primary goal is to target drug release in the intestines without premature drug dissolution in the stomach. This requires a coating with pH-dependent properties, the coating should protect the drug from acidic gastric fluid with a pH of 1-4 while the coating should readily dissolve upon reaching the duodenum for drug release when the fluid is neutralized by the addition of pancreatic fluid resulting in a pH of 5-6, with pH rising to 7 towards the colon. FDA-approved enteric formulations are currently available and they fall into two main categories based on their general chemical structure, one is based on cellulose derivatives, such as ethyl cellulose, hydroxypropyl cellulose and cellulose acetate phthalate, the other is a class of polyacrylates containing functional groups, such as methacrylic acid copolymers.

Existing solvent-based coating methods can only achieve proper coatings on particles greater than 100 µm in diameter. Being able to treat finer particles allow smaller drug particles to be delivered in more convenient dosing forms, such as tablets, since smaller particles provide greater surface area, improving dissolution rate. Smaller particles can also allow more delivery pathways, such as pulmonary or intravenous delivery, to be used, these pathways may be more effective entry points for drug delivery. In certain embodiments, ibuprofen is selected as a model drug compound. Ibuprofen is well-known as a non-steroidal, anti-inflammatory drug (NSAID) used to treat painful and inflammatory conditions, such as rheumatoid arthritis, osteoarthritis, ankylosing spondylitis, mild to moderate pain, dysmenorrhoea, vascular headache and fever. In one embodiment, the present invention is directed to methacrylic acid copolymers as enteric coatings around ibuprofen particles, of about 5 µm to about 35 µm in diameter, using a initiated chemical vapor deposition (iCVD) process. Current coating methods, including spray coating and fluidized bed coating from polymer solutions, are limited to coating particles of sizes larger than 100 µm. The ability to go to smaller particles improves drug absorption, allowing more convenient dosage forms, such as tablets, to be provided to patients.

Figure 21:
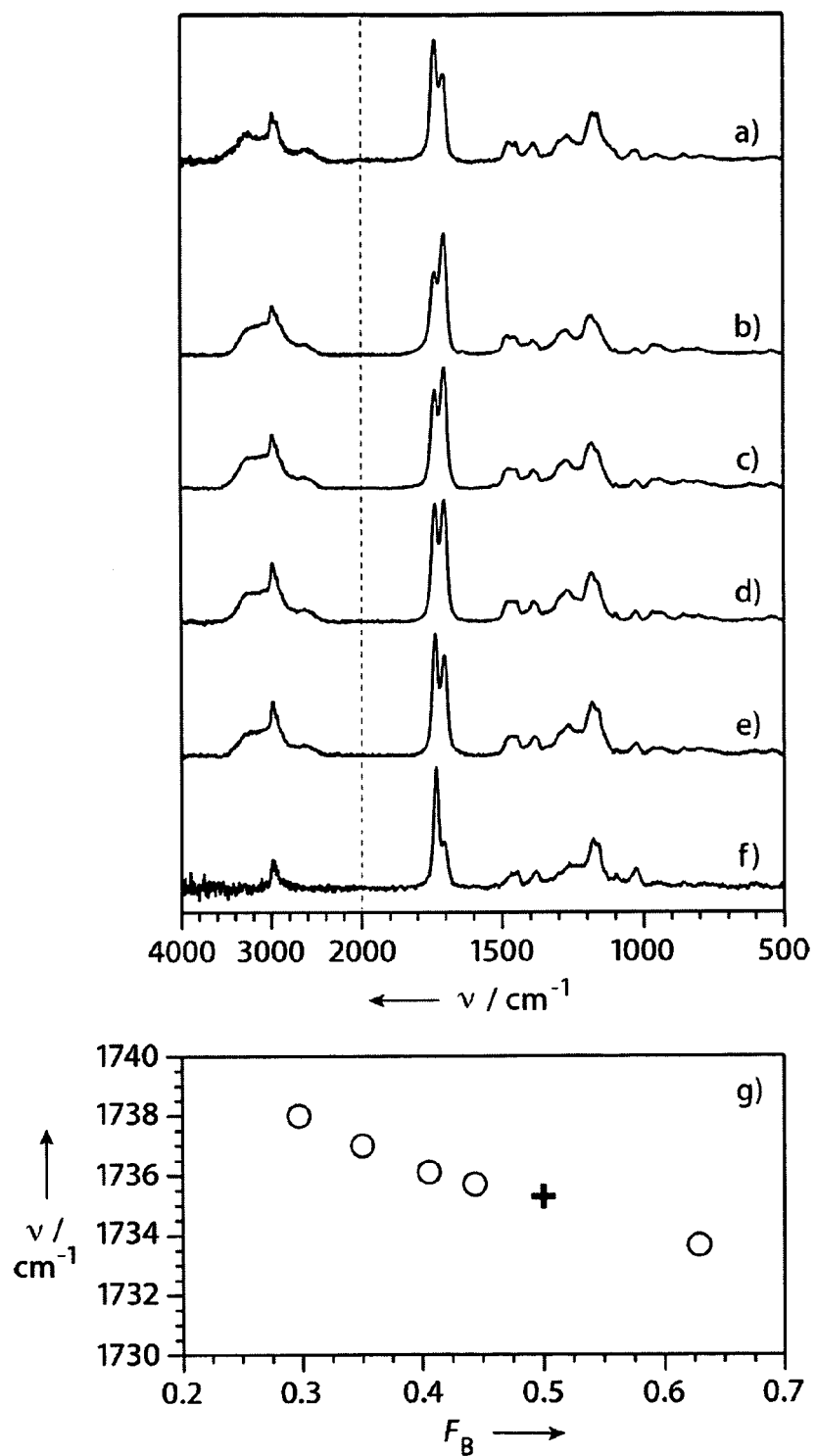
FIG. 21 depicts FTIR analysis of iCVD poly(methacrylic acid-co-ethyl acrylate). a) Eudragit L100-55, a 1:1 P(MAA-EA) copolymer from liquid-phase radical polymerization, compared to iCVD copolymers with different MAA:EA ratios of b) 70:30, c) 65:35, d) 59:41, e) 55:45, and f) 37:63. With more MAA, the broad OH absorption between 2500 and 3500 cm$^{-1}$ increases. Likewise, the MAA C=O stretch at ~1700 cm$^{-1}$ increases relative to the EA C=O stretch at ~1735 cm$^{-1}$. Note the scale change at 2000 cm$^{-1}$. g) There is a systematic shift in the EA C=O peak position as a function of the EA fraction in the copolymer, with the Eudragit standard (+) being positioned along the same trend as the iCVD copolymers.

For example, using methacrylic acid and ethyl acrylate as comonomers and tent-butyl peroxide as the free radical initiator, a series of poly(methacrylic acid-co-ethyl acrylate) with different comonomer ratios in the copolymer were synthesized through iCVD simply by varying the comonomer ratio in the feed. The series of P(MAA-EA) iCVD copolymers were used to determine and demonstrate iCVD's ability to produce copolymers. FIG. 21 shows the FTIR spectra for a series of iCVD P(MAA-EA) copolymers along with one of Eudragit L100-55, a 1:1 P(MAA-EA) copolymer obtained from Röhm that was made via liquid-phase radical polymerization. Quantitatively, the fractions of MAA and EA in the copolymers ($F_A$ and $F_B$) were determined by first resolving the carbonyl ester absorption into two separate peaks using a fitting program, GRAMS A/I (Thermo Galactic), corresponding to the MAA C=O stretch at ~1700 cm$^{-1}$ and the EA C=O stretch at ~1735 cm$^{-1}$. [J. Y. Lee, P. C. Painter, M. M. Coleman, *Macromolecules* 1988, 21, 346-354; and C. Mengel, A. R. Esker, W. H. Meyer, G. Wegner, *Langmuir* 2002, 18, 6365-6372.] The relative areas of the two peaks in the Eudragit copolymer was taken to represent a 1:1 MAA:EA ratio against which the ratios in the iCVD copolymers were then derived. Interestingly, when the peak position of the EA C=O stretch was plotted against $F_B$ (FIG. 21g), a systematic shift of the peak position can be observed. This strongly indicates that iCVD produces copolymers rather than a mixture of homopolymers as it is unlikely that the latter would lead to any significant FTIR shifts with changes in the relative amounts of the two comonomers since there is substantially no change in close range interactions that would affect bond vibrations. Further, with the peak position of the Eudragit copolymer lying within the same trend as the iCVD samples, it seems reasonable to imply that bond interactions in the iCVD samples must be similar to that in the liquid-phase copolymerized Eudragit.

Figure 22:
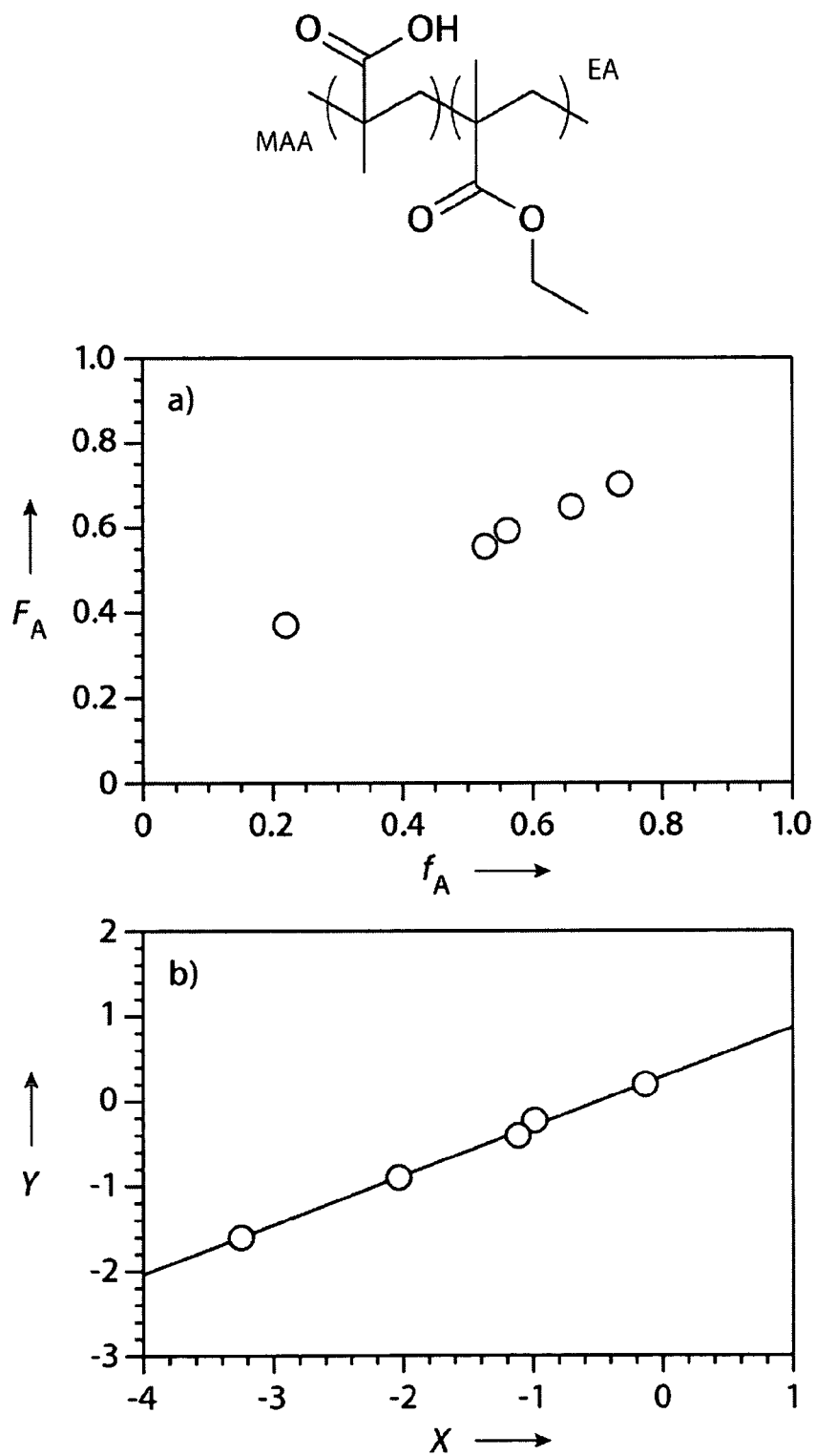
FIG. 22 depicts copolymer analysis of iCVD poly(methacrylic acid-co-ethyl acrylate). a) Plot of the fraction of MAA in the copolymer as a function of the fraction of MAA in the monomer feed at the deposition surface. An increase in MAA monomer at the deposition surface results in a systematic increase in MAA in the final copolymer. b) Plotting in the form of the Fineman-Ross copolymerization equation, the slope gives an MAA reactivity ratio, $r_A$=0.58, while the intercept gives an EA reactivity ratio, $r_B$=0.29 ($R^2$=0.9968).

Quantitatively, the fractions of MAA and EA in the monomer feed ($f_A$ and $f_B$) were also determined. These necessarily represent monomer fractions at the reaction surface rather than in the vapor phase since copolymerization is expected to occur only at the surface. [K. K. S. Lau, K. K. Gleason, *Macromolecules* 2006, 39, 3688-3694.; and K. K. S. Lau, K. K. Gleason, *Macromolecules* 2006, 39, 3695-3703.] Thus, the partial pressures of MAA and EA in the feed were corrected for by their saturated vapor pressures (0.93 and 36.4 Torr, respectively, at $T_{surface}$=25° C.). Briefly, this represents a conversion using Henry's law limit to derive a surface concentration. FIG. 22a plots the change in $F_A$ as a function of $f_A$, revealing a general increase in MAA in the copolymer as more MAA was present in the feed. Additionally, FIG. 22b gives a plot of the Fineman-Ross copolymerization equation in the form $Y=r_A \cdot X + r_B$, where $X=[f_A^2(F_A-1)]/[F_A f_B^2]$ and $Y=[f_A(1-2F_A)]/[F_A f_B]$. [M. Fineman, S. D. Ross, *J. Polym. Sci.* 1950, 5, 259-262.] The linear plot yields the reactivity ratios of MAA and EA, $r_A$=0.58 and $r_B$=0.29, respectively, under iCVD copolymerization conditions. These values can be compared to those for liquid phase radical copolymerization, $r_A$=3.12 and $r_B$=0.32, derived using the Q-e scheme. [R. Z. Greenley, *J. Macromol. Sci.-Chem.* 1975, A9, 505-516.] Remarkably, the values for EA are similar, which implies the reaction environments for EA under iCVD and liquid phase copolymerizations are comparable, both preferring to add MAA when the propagating radical has an EA radical end. On the other hand, MAA has a much greater tendency to add to its own type of propagating species when copolymerization occurs in the bulk liquid phase than when at the surface. This may be due to the greater ease with which MAA can orient favorably with each other through hydrogen bonding in a fluid phase that would facilitate self-propagation over cross-propagation. The product, $r_A \cdot r_B$=0.17, suggests that iCVD copolymerization follows a moderate alternating behavior, with each type of propagating radical preferring to add the other monomer. [G. Odian, *Principles of Polymerization*, John Wiley & Sons, Hoboken, N.J., 2004, p. 473.]

Figure 23:
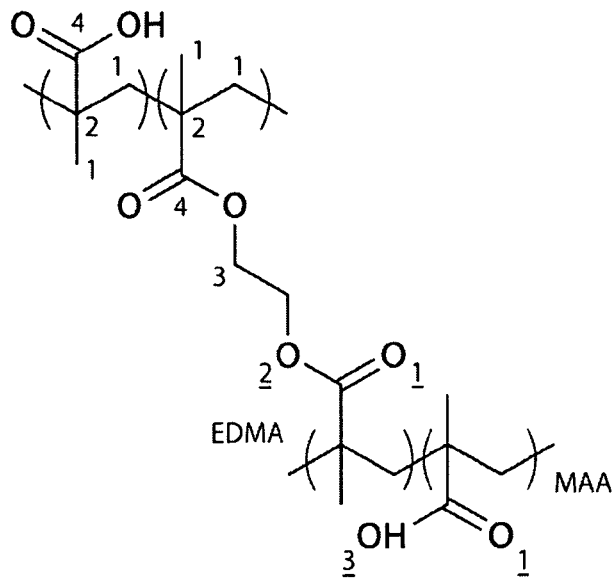
FIG. 23 depicts XPS analysis of iCVD poly(methacrylic acid-co-ethylene dimethacrylate). a) C1s is resolved into four distinct peaks, with peak 3 solely from EDMA. b) O1s is resolved into three distinct peaks, with peak 2 from EDMA and peak 3 from MAA. Spectra yields an MAA:EDMA copolymer ratio of 52:48.
Figure 23:
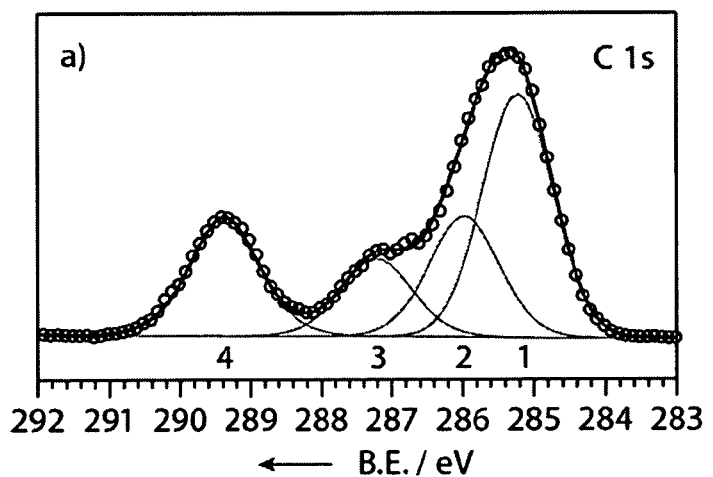
Figure 23:
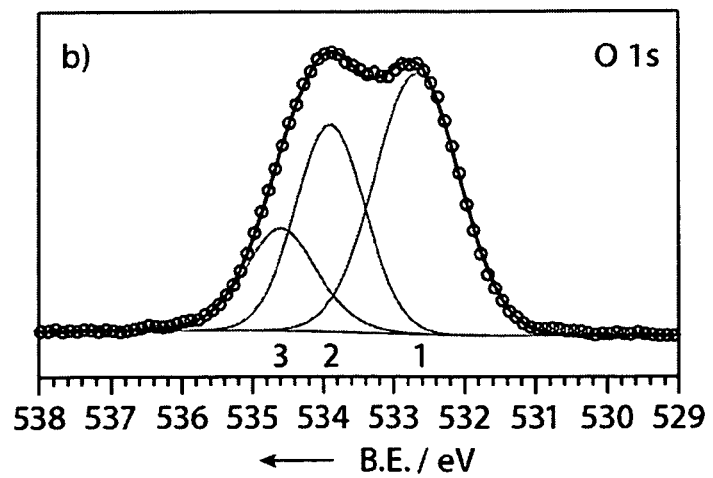

Using methacrylic acid and ethylene dimethacrylate as comonomers, the latter acting also as a crosslinking agent, and tert-amyl peroxide as the free radical initiator, poly (methacrylic acid-co-ethylene dimethacrylate) coatings were synthesized to demonstrate enteric release properties. FIG. 23 shows high resolution C1 s and O1 s XPS spectra of a P(MAA-EDMA) copolymer. By means of the CasaXPS program (Casa Software), the spectra have been resolved into four carbon and three oxygen environments, as assigned in FIG. 23. [G. Beamson, D. Briggs, *High Resolution XPS of Organic Polymers*, John Wiley & Sons, Chichester, England, 1992.] Since peak 3 in FIG. 23a belongs only to an EDMA carbon while peaks 2 and 3 in FIG. 23b belong separately to an EDMA and an MAA oxygen, respectively, it was possible to do a constrained fitting of both spectra simultaneously and thereby calculate an MAA:EDMA copolymer ratio of 52:48.

Figure 24:
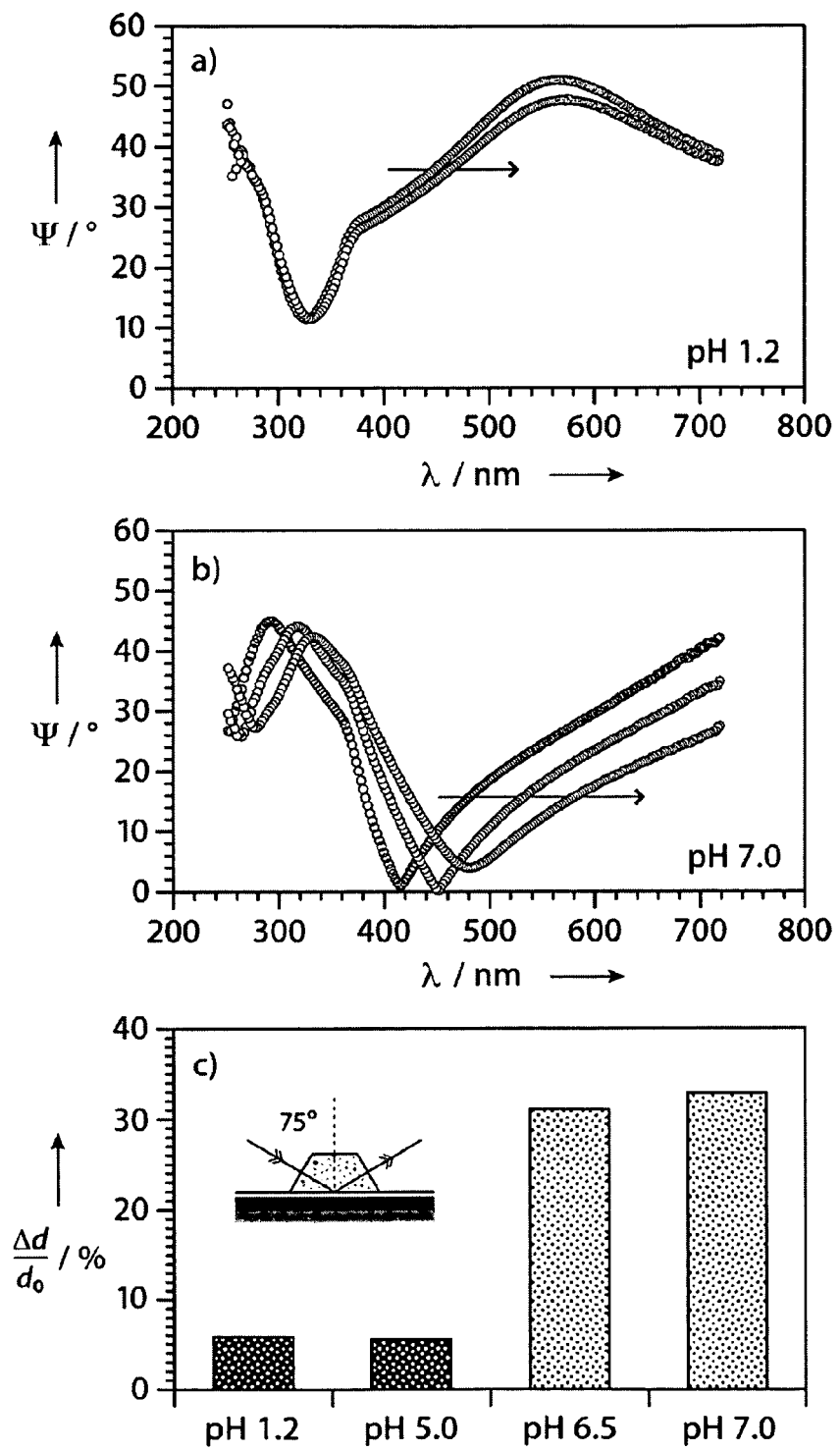
FIG. 24 depicts spectroscopic ellipsometry analysis of iCVD poly(methacrylic acid-co-ethylene dimethacrylate). a) At pH 1.2, there is only a slight shift in the Ψ curve between t=1 min and 18 h soak. b) At pH 7.0, there is a significant shift in the Ψ curve between t=1, 5 and 25 min soak. c) The spectra can be used to derive the change in copolymer film thickness between the initial dry film and the final swollen film under various pH buffer soaks. At acidic pH, the copolymer remains fairly dense with swelling of about 5%, while at near neutral pH and higher, the copolymer shows significant swelling of greater than about 30%.

By taking this P(MAA-EDMA) copolymer and immersing it in various pH buffers, its swelling behavior was determined by tracking the change in thickness of the copolymer coating (on silicon) using spectroscopic ellipsometry. As shown in FIGS. 24a and 24b, the raw Ψ angle curve shifted minimally when the copolymer was in a pH 1.2 soak even after several hours, while at pH 7.0, the curve shifted substantially within minutes. Any curve shift indicated a change in film thickness, which was subsequently derived based on standard model fitting using WVASE32 (J. A. Woollam). FIG. 24c shows the change in film thickness between the initial dry thickness and the final equilibrium swollen thickness under various pH buffer environments. The P(MAA-EDMA) copolymer did not swell appreciably (~5%) in acidic conditions, while swelling considerably (>30%) at near neutral and higher pH. There appears to be an abrupt transition at a pH between 5.0 and 6.5. This clearly demonstrates the enteric property of the iCVD P(MAA-EDMA) copolymer.

Figure 25:
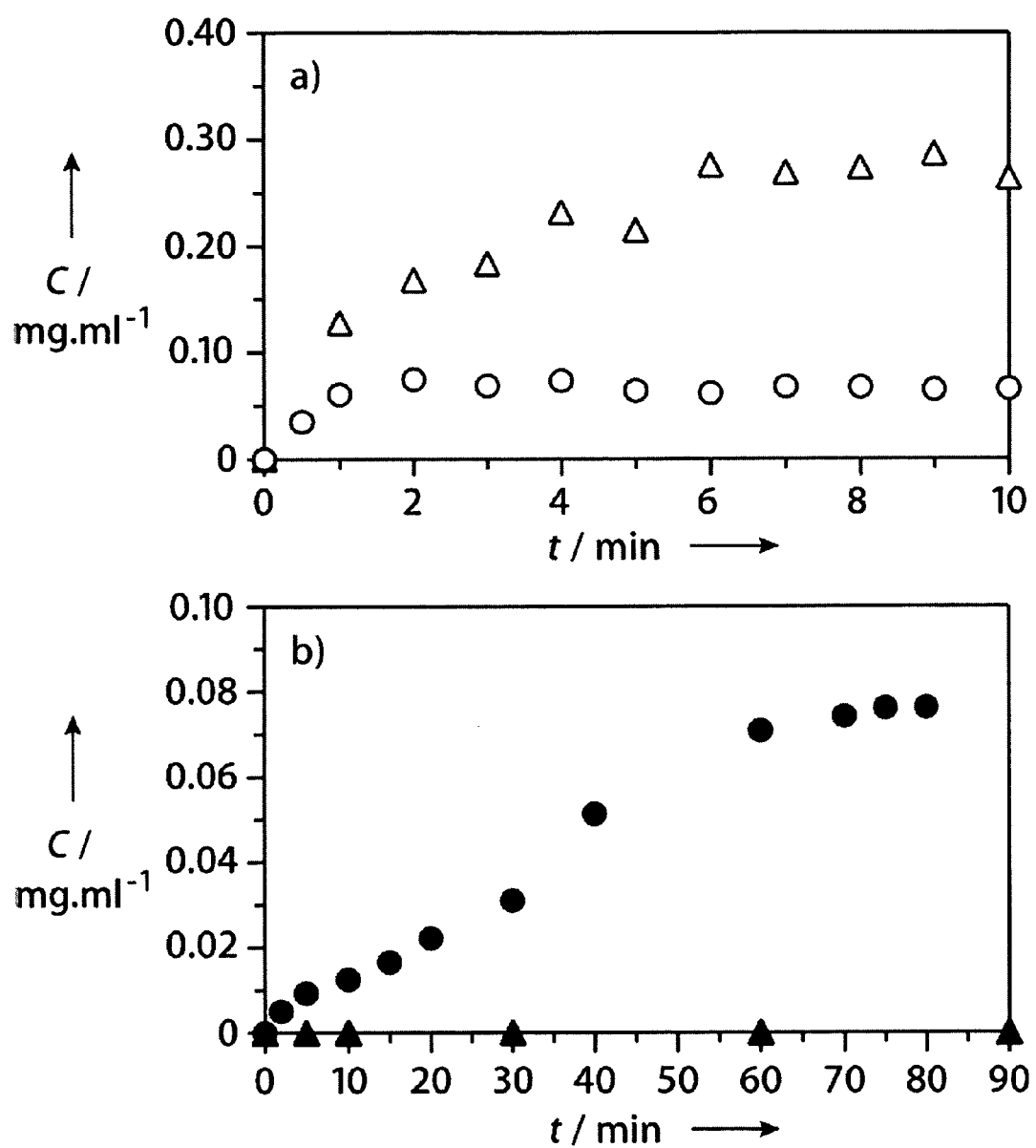
FIG. 25 depicts time release profiles of fluorescein. a) Uncoated, fluorescein dissolves relatively rapidly at both pH 1.2 (open triangle) and 6.8 (open circle). b) With iCVD P(MAA-EDMA) coating, fluorescein is protected at pH 1.2 (filled triangle), while, at pH 6.8 (filled circle), fluorescein is released over time with the swelling of the copolymer.

The pH-dependent swelling behavior of the P(MAA-EDMA) copolymer was made use of to demonstrate the enteric release of active agents. As described in the Exemplification, fluorescein was layered on top of silicon as a thin film, which was then encapsulated with the iCVD P(MAA-EDMA) copolymer coating. Release of fluorescein was then traced over time in different pH buffer environments, as shown in FIG. 25. Without any coating, fluorescein was completely released within 10 min, with a more rapid dissolution at pH 6.8 compared to pH 1.2 (FIG. 25a). In contrast, the presence of the iCVD P(MAA-EDMA) encapsulating layer prevented the release of fluorescein at pH 1.2 even after 90 min while, with substantial swelling of the copolymer expected at near neutral conditions, fluorescein was released at pH 6.8, albeit at a slower rate due to the diffusion resistance from the copolymer coating (FIG. 25b).

Figure 26:
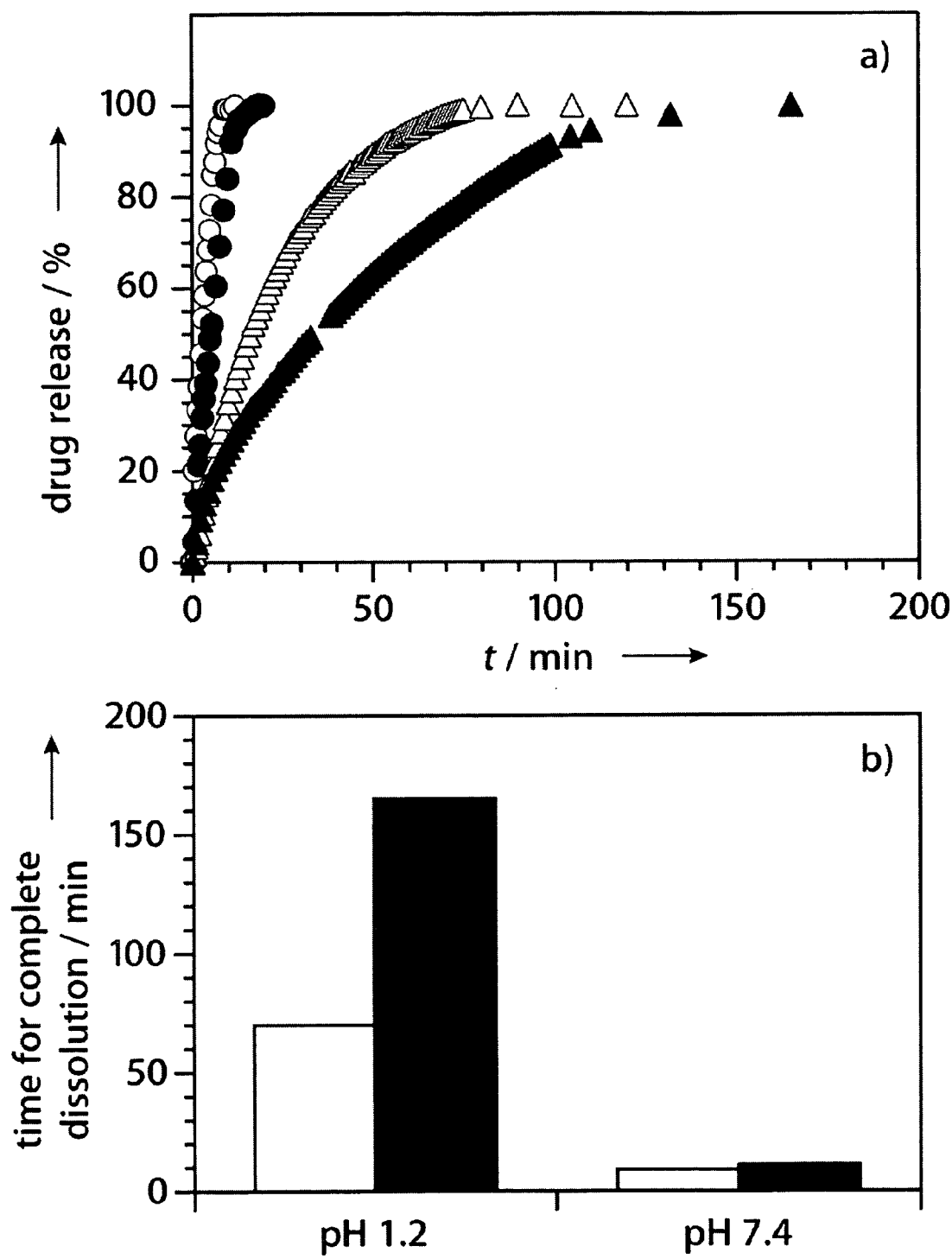
FIG. 26 depicts the controlled release of ibuprofen. a) Time release profiles, without coating (open symbols) and with the iCVD P(MAA-EDMA) coating (filled symbols), at pH 1.2 (triangle) and pH 7.4 (circle). b) The copolymer, acting as a diffusion barrier, significantly hinders ibuprofen release at acidic pH while, at near neutral pH, swelling of the copolymer allows the ibuprofen to be released with ease.

In another example, 25 μm ibuprofen microcrystals were encapsulated with the iCVD P(MAA-EDMA) copolymer and likewise ibuprofen release was tracked over time at different pH conditions. FIG. 26a gives the time release profiles, comparing uncoated and coated ibuprofen at pH 1.2 and 7.4. Release under a near neutral environment was relatively fast regardless of whether a coating was present or not while release under an acidic environment showed a significant delay with the added coating, increasing the time for complete dissolution by over 100% (FIG. 26b). This enhanced protection in acids would be important for drugs such as ibuprofen and other non-steroidal anti-inflammatory drugs that are known to cause stomach ulceration and hemorrhaging, leading to mucosal damage and severe blood loss with acute dosage and prolonged administration. [S. E. Gabriel, L. Jaakkimainen, C. Bombardier, *Ann. Intern. Med.* 1991, 115, 787-796; and [ M. M. Wolfe, D. R. Lichtenstein, G. Singh, *N. Engl. J. Med.* 1999, 340, 1888-1899.] The increase in drug dissolution and activity by using finer drug particles would likely exacerbate this problem. Thus, applying an enteric release coating to fine drug particles using the iCVD approach would be highly beneficial in minimizing undesirable patient response to chronic oral drug treatment while at the same time enhancing drug activity and efficacy by allowing finer drug particles to be used for treatment.

As these examples show, iCVD is an effective method for producing copolymer thin films and coatings via a free radical polymerization mechanism, with the ability to tune copolymer ratios systematically by simply adjusting comonomer feed ratios. By maintaining the substrates for coating at room temperature, iCVD is ideal for encapsulating thermally sensitive drugs. Without the use of any liquid phase, iCVD is able to encapsulate fine drug particles below 100 μm in size with methacrylic acid copolymer coatings and impart enteric release capabilities. These iCVD coatings offer a barrier against acid conditions while minimally affecting release under near neutral environments due to their pH-dependent swelling behavior. The iCVD coating treatment would ultimately benefit patients which undergo prolonged therapy with drugs that are prone to cause stomach ulcerations and bleeding.

ADDITIONAL SELECTED APPLICATIONS. In certain embodiments, the compositions and methods of the invention find application in, for example, thermal barriers, optical (visible and UV) barriers, image enhancement, ink-jet materials, coated abrasive slurries, information-recording layers, targets drug delivery, gene therapy, photonics, surface emobilization, as well as multifunctional nanocoatings.

In some applications high surface area is advantageous; high surface areas can be attained either by fabricating small particles or clusters where the surface-to-volume ratio of each particle is high, or by creating materials where the void surface area (pores) is high compared to the amount of bulk support material. Materials such as highly dispersed supported metal catalysts and gas phase clusters fall into the former category, and microporous (nanometer-pored) materials such as zeolites, high surface area inorganic oxides, porous carbons, and amorphous silicas fall into the latter category. There are many areas of where the use of coated nanostructures may have significant impact: (1) microporous materials for energy storage and separations technologies, including nanostructured materials for highly selective adsorption/separation processes such as $H_2O$, $H_2S$, or $CO_2$ removal; high capacity, low volume gas storage of $H_2$ and $CH_4$ for fuel cell applications and high selectivity; high permeance gas separations such as $O_2$ enrichment; and $H_2$ separation and recovery; (2) thermal barrier materials for use in high temperature engines; (3) understanding certain atmospheric reactions; (4) incorporation into construction industry materials for improved strength or for fault diagnostics; (5) battery or capacitor elements for new or improved operation; (6) biochemical and pharmaceutical separations; or (7) product-specific catalysts for almost every petrochemical process.

One aspect of the present invention relates to the use of initiated CVD (iCVD) to produce thin films of hydrogels. A hydrogel is a colloidal gel in which water is the dispersion medium. Hydrogels are superabsorbent (they can contain over 90% of water) natural or synthetic polymers. In other words, in certain embodiments, the inventive films function as hydrogels when soaked in water [See Gleason, K. et al. U.S. patent application Ser. No. 11/198,932, hereby incorporated by reference.]

As mentioned above, dispersive and coating applications of nanoparticles include optical, thermal, and diffusion barriers. Nanoscale dispersions and coatings of the type disclosed herein may find uses in areas of ceramics, cosmetics, biosensors, colorants, and abrasion-resistant polymers. Other applications include imaging ink jet materials, electrophotography, pharmaceuticals, flavor enhancers, pesticides, lubricants, and other proprietary applications specific to industry. Still another application is in a new, post-silicon generation of electronic devices that includes nanotubes and fullerenes as constituent units of carbon nanoelectronic devices; note that here, dispersion takes on a more quantum consideration in which the number of atoms in a cluster is compared to the number of surface atoms to determine its dispersion function. In addition, in the semiconductor industry, a monolayer or thin film coating of atoms or molecules is deposited on foils, metal sheets, or glass to enhance storage capacity and accelerate responses from the electronic component. All these applications deal with dispersions or coatings of particles that enhance specific features. In addition, the ability to manufacture smaller functional systems enhances performance, cost, and efficiency. Below are some general examples of the vast array of applications of nanoparticulate dispersions and coatings.

Cosmetics. An area of nanoparticle technology that has incredible commercial potential is the cosmetic industry. Here there is a great demonstrated demand, and the technology can be made simple, since properties of color and light fastness are achieved by component mixing in the cosmetic preparation. A survey in 1990 indicated a worldwide gross volume of $14-18 billion for toiletries, i.e., traditional hygiene products such as powders, sprays, perfumes, and deodorants. The large markets for sunscreens and skin rejuvenation preparations promise additional revenues. The diet industry is said to gross $33 billion annually. One way that nanoparticle technology is addressing this market is through introducing nanoparticulate taste enhancers into low-calorie substrates.

Printing. In the areas of image capture/image output addressed by ink jet technology, nanoscience, such as particles and methods of the instant invention, may help control the properties of the inks themselves. The production and use of nanoengineered ink products benefits from such complimentary technology as laser-assist delivery of the ink jet droplet to maintain an accurate deposit of the ink on its target. Another application in this field is using nanoscale properties to tailor the inks to achieve ideal absorption and drying times for desired color properties and permanency.

Semiconductors. One form of "bottom up" technology that is receiving considerable attention is thin films for the semiconductor industry. Here single atoms or molecules are deposited by physical vapor deposition, which could be achieved through sputtering, molecular beam epitaxy, or chemical vapor deposition. Sputtering is used on a large scale to coat metal sheets, glass, polymer substrates and other receptive materials in order to produce enhanced electronic properties for information storage and processing speed.

Sensors. Chemical or physical sensors often use nanoparticles because they provide high surface area for detecting the state of chemical reactions, because the quality of detection signals is improved, and because earlier and more accurate determination of leakage reduces waste. Some commercial sensors and actuators composed of thin films are already used for environmental vapor monitoring in reactors, for example.

Medicine/Pharmacology. In the area of medical applications, finely dispersed pharmaceuticals offer rapid drug delivery and reduced dosages for patients (as discussed in part above). Dispersions of strong and resilient biocompatible materials suggest opportunities for artificial joints. These generally are ceramic materials containing nanoparticulates. Overall, much of the demand for nanoparticulate dispersions and coatings comes from the cosmetic and pharmaceutical industries; in particular, liquid dispersion preparations will be widely used to apply topical coatings to the human epidermis because they can be absorbed faster and more completely than conventional coatings.

DEFINITIONS. For convenience, definitions of certain terms employed in the specification, examples, and appended claims are collected here.

As used herein, the term "polymer" means a molecule, formed by the chemical union of two or more oligomer units. The chemical units are normally linked together by covalent linkages. The two or more combining units in a polymer can be all the same, in which case the polymer is referred to as a homopolymer. They can be also be different and, thus, the polymer will be a combination of the different units. These polymers are referred to as copolymers. In certain embodiments, the polymer coating is a block copolymer, random copolymer, graft polymer, or branched copolymer.

The phrase "weight average molecular weight" refers to a particular measure of the molecular weight of a polymer. The weight average molecular weight is calculated as follows: determine the molecular weight of a number of polymer molecules; add the squares of these weights; and then divide by the total weight of the molecules.

The phrase "number average molecular weight" refers to a particular measure of the molecular weight of a polymer. The number average molecular weight is the common average of the molecular weights of the individual polymer molecules. It is determined by measuring the molecular weight of n polymer molecules, summing the weights, and dividing by n.

The phrase "polydispersity index" refers to the ratio of the "weight average molecular weight" to the "number average molecular weight" for a particular polymer; it reflects the distribution of individual molecular weights in a polymer sample.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth on page 560 of "Advanced Inorganic Chemistry" by Cotton and Wilkinson.

The terms "amine" and "amino" are art-recognized and refer to both unsubstituted and substituted amines, e.g., a moiety that may be represented by the general formulas:

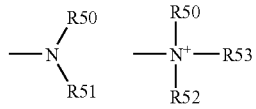

wherein R50, R51, R52 and R53 each independently represent a hydrogen, an alkyl, an alkenyl, —(CH$_2$)$_m$—R61, or R50 and R51 or R52, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

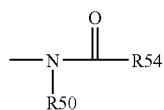

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

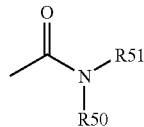

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

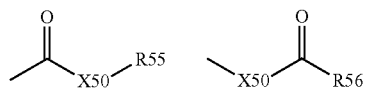

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

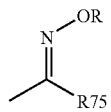

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

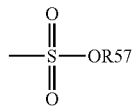

in which R57 is an electron pair, hydrogen, alkyl, cycloalkyl, or aryl.

The term "sulfate" is art recognized and includes a moiety that may be represented by the general formula:

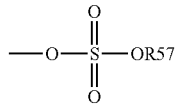

in which R57 is as defined above.

The term "sulfonamido" is art recognized and includes a moiety that may be represented by the general formula:

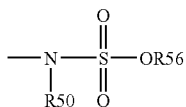

in which R50 and R56 are as defined above.

The term "sulfamoyl" is art-recognized and refers to a moiety that may be represented by the general formula:

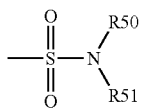

in which R50 and R51 are as defined above.

The term "sulfonyl" is art-recognized and refers to a moiety that may be represented by the general formula:

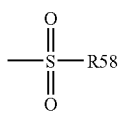

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

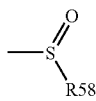

in which R58 is defined above.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, "Handbook of Chemistry and Physics", 67th Ed., 1986-87, inside cover.

SELECTED COATED PARTICLES OF THE INVENTION. One aspect of the present invention relates to a coated particle comprising a particle and a coating of polymerized monomers on the surface of said particle; wherein said particle has an surface area of between about 10 nm$^2$ and about 30 mm$^2$; said monomer is selected from the group consisting of

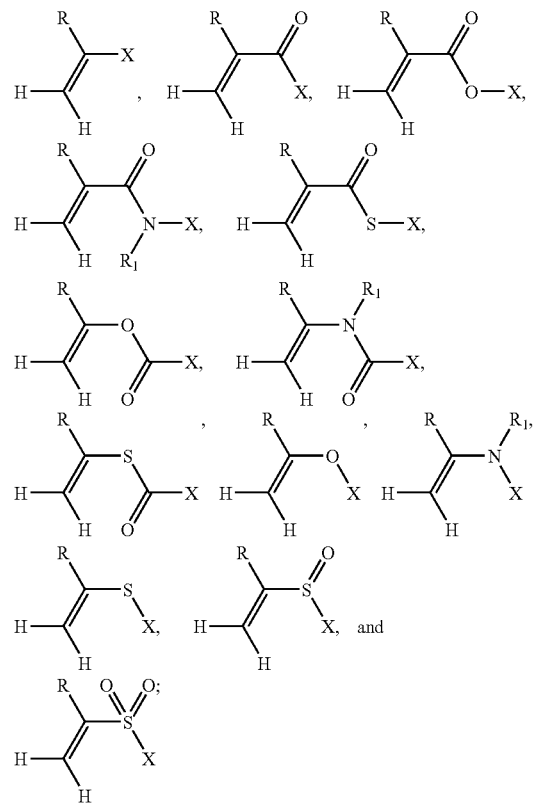

R is selected from the group consisting of hydrogen and alkyl; R$^1$ is selected from the group consisting of hydrogen, alkyl, aralkyl, heteroaralkyl, and carboxyl; X is selected from the group consisting of hydrogen, alkyl, cycloalkyl, heteocycloalkyl, aryl, heteroaryl, aralkyl, heteoaralkyl, and —(CH$_2$)$_n$Y; Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido; and n is 1-10 inclusive.

In certain embodiments, the present invention relates to the aforementioned particle, wherein R is hydrogen. In certain embodiments, the present invention relates to the aforementioned particle, wherein R is methyl. In certain embodiments, the present invention relates to the aforementioned particle, wherein X is —(CH$_2$)$_n$Y. In certain embodiments, the present invention relates to the aforementioned particle, wherein Y is alkyl, cycloalkyl, heterocycloalkyl, aryl, nitro, halo, hydroxyl, alkyoxy, aryloxy, amino, acylamino, amido, or carbamoyl. In certain embodiments, the present invention relates to the aforementioned particle, wherein n is 3-8 inclusive.

Another aspect of the present invention relates to a coated particle comprising a particle and a coating of polymerized monomers on the surface of said particle; wherein said particle has a surface area of between about 10 nm$^2$ microns and about 30 mm$^2$; said monomer is selected from the group consisting of

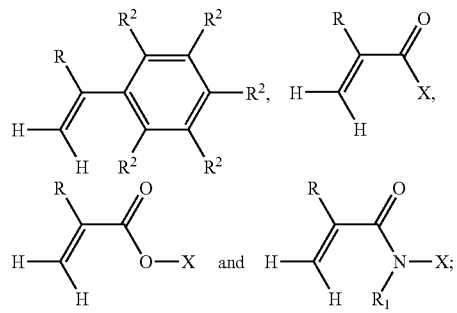

R is selected from the group consisting of hydrogen and alkyl; R$^1$ is selected from the group consisting of hydrogen, alkyl, aralkyl, heteroaralkyl, and carboxyl; R$^2$ is independently selected from the group consisting of hydrogen, alkyl, bromine, chlorine, hydroxyl, alkyoxy, aryloxy, carboxyl, amino, acylamino, amido, carbamoyl, sulfhydryl, sulfonate, and sulfoxido; X is selected from the group consisting of hydrogen, alkyl, cycloalkyl, heteocycloalkyl, aryl, heteroaryl, aralkyl, heteoaralkyl, and —(CH$_2$)$_n$Y; Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido; and n is 1-10 inclusive.

In certain embodiments, the present invention relates to the aforementioned particle, wherein R is hydrogen. In certain embodiments, the present invention relates to the aforementioned particle, wherein R is methyl. In certain embodiments, the present invention relates to the aforementioned particle, wherein R$^1$ is aralkyl or carboxyl. In certain embodiments, the present invention relates to the aforementioned particle, wherein R$^2$ is independently selected from the group consisting of hydrogen, alkyl, bromine and chlorine. In certain embodiments, the present invention relates to the aforementioned particle, wherein X is hydrogen or —(CH$_2$)$_n$Y. In certain embodiments, the present invention relates to the aforementioned particle, wherein Y is alkyl, cycloalkyl, heterocycloalkyl, aryl, nitro, halo, hydroxyl, alkyoxy, aryloxy, amino, acylamino, amido, or carbamoyl. In certain embodiments, the present invention relates to the aforementioned particle, wherein n is 3-8 inclusive.

Another aspect of the present invention relates to a coated particle comprising a particle and a coating of polymerized monomers on the surface of said particle; wherein said particle has a surface area of between about 10 nm$^2$ and about 30 mm$^2$ microns; said monomer is

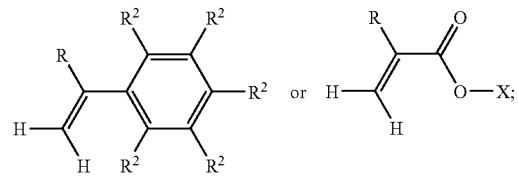

R is selected from the group consisting of hydrogen and methyl; R$^2$ is independently selected from the group consisting of hydrogen, methyl, bromine and chlorine; X is hydrogen or —(CH$_2$)$_n$Y; Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido; and n is 1-10 inclusive.

In certain embodiments, the present invention relates to the aforementioned particle, wherein R is hydrogen. In certain embodiments, the present invention relates to the aforementioned particle, wherein R is methyl. In certain embodiments, the present invention relates to the aforementioned particle, wherein R$^2$ is independently selected from the group consisting of hydrogen and methyl. In certain embodiments, the present invention relates to the aforementioned particle, wherein R$^2$ is independently selected from the group consisting of hydrogen and bromine. In certain embodiments, the present invention relates to the aforementioned particle, wherein R$^2$ is independently selected from the group consisting of hydrogen and chlorine. In certain embodiments, the present invention relates to the aforementioned particle, wherein Y is hydrogen or heterocyloalkyl. In certain embodiments, the present invention relates to the aforementioned particle, wherein Y is hydrogen. In certain embodiments, the present invention relates to the aforementioned particle, wherein Y is an oxirane. In certain embodiments, the present invention relates to the aforementioned particle, wherein n is 3-8 inclusive.

Another aspect of the present invention relates to a coated particle comprising a particle and a coating of polymerized monomers on the surface of said particle; wherein said particle has a surface area of between about 10 nm$^2$ and about 30 mm$^2$; and said monomer is selected from the group consisting of poly(glycidyl methacrylate), p-bromophenyl methacrylate, pentabromophenyl methacrylate, n-vinyl carbazole, p-divinyl benzene, styrene, alpha methyl styrene, 2-chlorostyrene, 3-chlorostyrene, 4-chlorostyrene, 2,3-dichlorostyrene, 2,4-dichlorostyrene, 2,5-dichlorostyrene, 2,6-dichlorostyrene, 3,4-dichlorostyrene, 3,5-dichlorostyrene, 2-bromostyrene, 3-bromostyrene, 4-bromostyrene, 2,3-dibromostyrene, 2,4-dibromostyrene, 2,5-dibromostyrene, 2,6-dibromostyrene, 3,4-dibromostyrene, 3,5-dibromostyrene, methyl acrylate, n-butyl acrylate, n-pentyl acrylate, n-hexyl acrylate, n-heptyl acrylate, n-octyl acrylate, 2-ethylhexyl acrylate, perfluorocyclohexylmethyl acrylate, benzyl acrylate, 2-hydroxyethyl acrylate, dimethylaminoethyl acrylate, Et$_3$DMAA, sec-butyl acrylate, tert-butyl acrylate, isobornyl acrylate, ethylene glycol diacrylate, methyl methacrylate, ethyl methacrylate, n-propyl methacrylate, n-butyl methacrylate, isobutyl methacrylate, n-pentyl methacrylate, n-hexyl methacrylate, n-heptyl methacrylate, sec-butyl methacrylate, tert-amyl methacrylate, t-butyl methacrylate, dimethylaminoethyl methacrylate, hydroxyethyl methacrylate, cyclohexyl methacrylate, benzyl methacrylate, isobornyl methacrylate, glycidyl methacrylate, ethylene glycol dimethacrylate, methacrylic acid, styrene, alpha-methyl styrene, ortho-methyl styrene, meta-methyl styrene, para-methyl styrene, para-ethyl styrene, 2,4-dimethyl styrene, 2,5-dimethyl styrene, m-divinylbenzene, p-divinylbenzene, vinylimidazole, N-vinyl-2-pyrrolidone, V3D3, 1,4-divinyloxybutane, diethylene glygol divinyl ether, 1,5-hexadiene-3,4-diol DVG, methyl trans-cinnamate, N-morpholinoethyl acrylate, 2-morpholinoethyl methacrylate, 2-isocyanatoethyl methacrylate, 2-sulfoethyl methacrylate, 2-methoxyethyl methacrylate, 2-(tert-butylamino)ethyl methacrylate, 2-ethoxyethyl methacrylate, 2-chloroethyl methacrylate, 2-hydroxypropyl methacrylate, 2-diethylaminoethyl methacrylate, cyclopentyl methacrylate, 2-(diisopropylamino)ethyl methacrylate, 2-bromoethyl methacrylate, and 2-phenylethyl methacrylate. In certain embodiments, the present invention relates to the aforementioned particle, wherein said monomer is poly(glycidyl methacrylate).

In certain embodiments, the present invention relates to the aforementioned particle, further comprising an additional monomer, to yield a copolymer on said surface. The additional monomer may be any monomer as described herein.

In certain embodiments, the present invention relates to the aforementioned particle, further comprising a crosslinker, thereby forming a crosslinked polymer coating. The crosslinker may be selected from the group consisting of a low molecular weight di- or polyvinylic crosslinking agent such as ethyleneglycol diacrylate or dimethacrylate, di-, tri- or tetraethylen-glycol diacrylate or dimethacrylate, allyl (meth)acrylate, a $C_2$-$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol diacrylate or dimethacrylate, methylene bisacrylamide or methylene bismethacrylamide, ethylene bisacrylamide or ethylene bismethacrylamide, and triallyl phthalate or diallyl phthalate. In certain embodiments, the crosslinker according to the invention is ethyleneglycol-dimethacrylate or ethyleneglycol-diacrylate.

Another aspect of the present invention relates to a coated particle comprising a particle and a polymer coating on the surface of said particle; wherein said particle has an surface area of between about 10 nm$^2$ and about 30 mm$^2$; said polymer coating is represented by

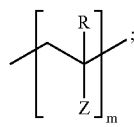

Z is selected independently for each occurrence from the group consisting of —X, —C(=O)X, —C(=O)OX, —C(=O)N(R$^1$)X, —C(=O)SX, —OC(=O)X, —N(R$^1$)C(=O)X, —SC(=O)X, —OX, —N(R$^1$)X, —SX, —S(=O)X, and —S(=O)$_2$X; R is selected independently for each occurrence from the group consisting of hydrogen and alkyl; R$^1$ is selected independently for each occurrence from the group consisting of hydrogen, alkyl, aralkyl, heteroaralkyl, and carboxyl; X is selected independently for each occurrence from the group consisting of hydrogen, alkyl, cycloalkyl, heteocycloalkyl, aryl, heteroaryl, aralkyl, heteoaralkyl, and —(CH$_2$)$_n$Y; Y is selected independently for each occurrence from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido; n is, independently for each occurrence, 1-10 inclusive; and m is 30-300 inclusive.

In certain embodiments, the present invention relates to the aforementioned particle, wherein R is hydrogen. In certain embodiments, the present invention relates to the aforementioned particle, wherein R is methyl. In certain embodiments, the present invention relates to the aforementioned particle, wherein X is —(CH$_2$)$_n$Y. In certain embodiments, the present invention relates to the aforementioned particle, wherein Y is alkyl, cycloalkyl, heterocycloalkyl, aryl, nitro, halo, hydroxyl, alkyoxy, aryloxy, amino, acylamino, amido, or carbamoyl. In certain embodiments, the present invention relates to the aforementioned particle, wherein n is 3-8 inclusive.

Another aspect of the present invention relates to a coated particle comprising a particle and a polymer coating on the surface of said particle; wherein said particle has an surface area of between about 10 nm$^2$ and about 30 mm$^2$; said polymer coating is represented by

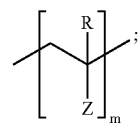

Z is selected independently for each occurrence from the group consisting of —C$_6$(R$^2$)$_5$, —C(=O)X, —C(=O)OX, and —C(=O)N(R$^1$)X; R is selected from the group consisting of hydrogen and alkyl; R$^1$ is selected from the group consisting of hydrogen, alkyl, aralkyl, heteroaralkyl, and carboxyl; R$^2$ is independently selected from the group consisting of hydrogen, alkyl, bromine, chlorine, hydroxyl, alkyoxy, aryloxy, carboxyl, amino, acylamino, amido, carbamoyl, sulfhydryl, sulfonate, and sulfoxido; X is selected from the group consisting of hydrogen, alkyl, cycloalkyl, heteocycloalkyl, aryl, heteroaryl, aralkyl, heteoaralkyl, and —(CH$_2$)$_n$Y; Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido; n is, independently for each occurrence, 1-10 inclusive; and m is 30-300 inclusive.

In certain embodiments, the present invention relates to the aforementioned particle, wherein R is hydrogen. In certain embodiments, the present invention relates to the aforementioned particle, wherein R is methyl. In certain embodiments, the present invention relates to the aforementioned particle, wherein R$^1$ is aralkyl or carboxyl. In certain embodiments, the present invention relates to the aforementioned particle, wherein R2 is independently selected from the group consisting of hydrogen, alkyl, bromine and chlorine. In certain embodiments, the present invention relates to the aforementioned particle, wherein X is —(CH$_2$)$_n$Y. In certain embodiments, the present invention relates to the aforementioned particle, wherein Y is alkyl, cycloalkyl, heterocycloalkyl, aryl, nitro, halo, hydroxyl, alkyoxy, aryloxy, amino, acylamino, amido, or carbamoyl. In certain embodiments, the present invention relates to the aforementioned particle, wherein n is 3-8 inclusive.

Another aspect of the present invention relates to a coated particle comprising a particle and a polymer coating on the surface of said particle; wherein said particle has an surface area of between about 10 nm² and about 30 mm²; said polymer coating is represented by

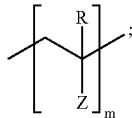

Z is selected independently for each occurrence from the group consisting of —C₆(R²)₅, and —C(=O)OX; R is selected from the group consisting of hydrogen and methyl; R² is independently selected from the group consisting of hydrogen, methyl, bromine and chlorine; X is —(CH₂)ₙY; Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido; n is, independently for each occurrence, 1-10 inclusive; and m is 30-300 inclusive.

In certain embodiments, the present invention relates to the aforementioned particle, wherein R is hydrogen. In certain embodiments, the present invention relates to the aforementioned particle, wherein R is methyl. In certain embodiments, the present invention relates to the aforementioned particle, wherein R² is independently selected from the group consisting of hydrogen and methyl. In certain embodiments, the present invention relates to the aforementioned particle, wherein R² is independently selected from the group consisting of hydrogen and bromine. In certain embodiments, the present invention relates to the aforementioned particle, wherein R² is independently selected from the group consisting of hydrogen and chlorine. In certain embodiments, the present invention relates to the aforementioned particle, wherein Y is hydrogen or heterocyloalkyl. In certain embodiments, the present invention relates to the aforementioned particle, wherein Y is hydrogen. In certain embodiments, the present invention relates to the aforementioned particle, wherein Y is an oxirane. In certain embodiments, the present invention relates to the aforementioned particle, wherein n is 3-8 inclusive. In certain embodiments, the present invention relates to the aforementioned particle, wherein Z is selected independently for each occurrence from the group consisting of —C(=O)OH and —C(=O)OCH₂CH₃.

Another aspect of the present invention relates to a coated particle comprising a particle and a polymer coating on the surface of said particle; wherein said particle has a surface area of between about 10 nm² and 30 mm²; said polymer coating is

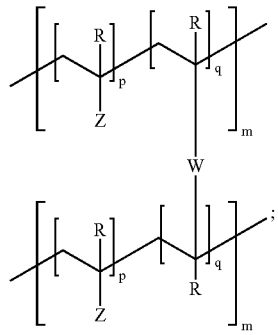

Z is selected independently for each occurrence from the group consisting of —X, —C(=O)X, —C(=O)OX, —C(=O)N(R¹)X, —C(=O)SX, —OC(=O)X, —N(R¹)C(=O)X, —SC(=O)X, —OX, —N(R¹)X, —SX, —S(=O)X, and —S(=O)₂X; W is selected independently for each occurrence from the group consisting of —(CH₂)ₙ—,

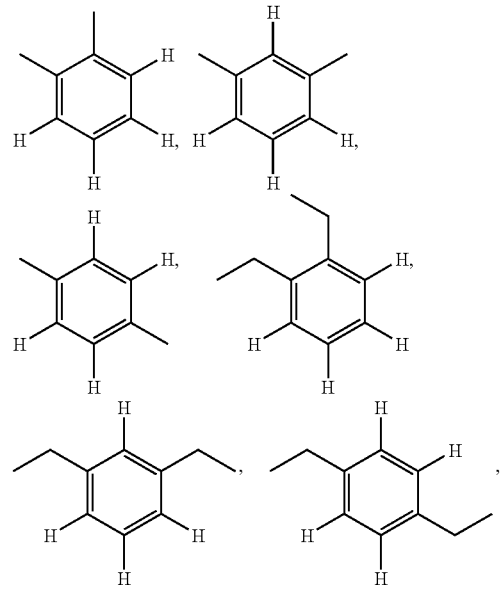

—C(=O)—(CH₂)ₙ—C(=O)—, —OC(=O)—(CH₂)ₙ—C(=O)O—, —N(R¹)C(=O)—(CH₂)ₙ—C(=O)N(R¹)—, —SC(=O)—(CH₂)ₙ—C(=O)S—, —C(=O)O—(CH₂)ₙ—OC(=O)—, —C(=O)N(R¹)—(CH₂)ₙ—N(R¹)C(=O)—, —C(=O)S—(CH₂)ₙ—SC(=O)—, —O—(CH₂)ₙ—O—, —N(R¹)—(CH₂)ₙ—N(R¹)— and —S—(CH₂)ₙ—S—; R¹ is selected independently for each occurrence from the group consisting of hydrogen and alkyl; R¹ is selected independently for each occurrence from the group consisting of hydrogen, alkyl, aralkyl, heteroaralkyl, and carboxyl; X is selected independently for each occurrence from the group consisting of hydrogen, alkyl, cycloalkyl, heteocycloalkyl, aryl, heteroaryl, aralkyl, heteoaralkyl, and —(CH₂)ₙY; Y is selected independently for each occurrence from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido; p is, independently for each occurrence, 0 or 1; q is, independently for each occurrence, 0 or 1; n is 1-10 inclusive; and m is 30-300 inclusive.

In certain embodiments, the present invention relates to the aforementioned particle, wherein R is hydrogen or methyl. In certain embodiments, the present invention relates to the aforementioned particle, wherein Z is selected independently for each occurrence from the group consisting of —C₆(R²)₅, —C(=O)X, —C(=O)OX, and —C(=O)N(R¹)X; and R² is independently selected from the group consisting of hydrogen, alkyl, bromine, chlorine, hydroxyl, alkyoxy, aryloxy, carboxyl, amino, acylamino, amido, carbamoyl, sulfhydryl, sulfonate, and sulfoxido. In certain embodiments, the present invention relates to the aforementioned particle, wherein Z is selected independently for each occurrence from the group consisting of —C₆(R²)₅, and —C(=O)OX; R is selected from the group consisting of hydrogen and methyl; $R^2$ is independently selected from the group consisting of hydrogen, methyl, bromine and chlorine; X is —$(CH_2)_nY$; and Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido. In certain embodiments, the present invention relates to the aforementioned particle, wherein Z is —C(=O)OH for every occurrence and W is —C(=O)OCH$_2$CH$_2$C(=O)—.

In certain embodiments, the present invention relates to the aforementioned particle, wherein said particle is selected from the group consisting of ceramics and glasses, oxides, carbides, nitrides, metals, minerals, semiconductors, polymers, carbon, magnetic particles, superconducting particles-quantum dots, fluorescent particles, colored or dyed particles, colloidal particles, microparticles, microspheres, microbeads, nanoparticles, nanospheres, nanorods, nanowires, shell particles, core particles, organic nanoparticles, and inorganic-organic hybrid nanoparticles.

In certain embodiments, the present invention relates to the aforementioned particle, wherein said particle is selected from the group consisting of fused silica, fumed silica, soda glass, silica, alumina, zirconia, ceria, yttria, and titania, tin oxide, indium oxide, zinc oxide, boron tin oxide, boron zinc oxide, tantalum carbide (TaC), boron carbide ($B_4C$), silicon carbide (SiC), titanium carbide, titanium nitride (TiN), boron nitride ($B_4N$), gold (Au), silicon (Si), silver (Ag), platinum (Pi) nickel (Ni), calcium fluoride ($CaF_2$), quartz, silicon (Si), germanium (Ge), cadmium telluride (CdTd), gallium arsenide (GaAs), polystyrene, polymethylmethacrylate, latex; graphite, fullerenes, nanotubes, and diamond.

In certain embodiments, the present invention relates to the aforementioned particle, wherein said particle is a biologically active substance. In certain embodiments, the present invention relates to the aforementioned particle, wherein said particle is a biologically active substance selected from the group consisting of anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and antithyroid agents, uterine relaxants, vitamins, and prodrugs.

In certain embodiments, the present invention relates to the aforementioned particle, wherein said surface area is between about 10 nm$^2$ and about 30 mm$^2$. In certain embodiments, the present invention relates to the aforementioned particle, wherein said surface area is between about 50 nm$^2$ and about 10 mm$^2$. In certain embodiments, the present invention relates to the aforementioned particle, wherein said surface area is between about 100 nm$^2$ microns and about 1 mm$^2$ In certain embodiments, the present invention relates to the aforementioned particle, wherein said surface area is between about 10 nm$^2$ and about 1 mm$^2$. In certain embodiments, the present invention relates to the aforementioned particle, wherein said surface area is between about 50 nm$^2$ and about 1 mm$^2$.

In certain embodiments, the present invention relates to the aforementioned particle, wherein said polymer coating has an average thickness of between about 0.1 nm and about 100 nm. In certain embodiments, the present invention relates to the aforementioned particle, wherein said polymer coating has an average thickness of between about 0.1 nm and about 50 nm. In certain embodiments, the present invention relates to the aforementioned particle, wherein said polymer coating has an average thickness of between about 0.1 nm and about 1 nm. In certain embodiments, the present invention relates to the aforementioned particle, wherein said polymer coating has an average thickness of between about 0.5 nm and about 50 nm. In certain embodiments, the present invention relates to the aforementioned particle, wherein said polymer coating has an average thickness of between about 1 nm and about 35 nm. In certain embodiments, the present invention relates to the aforementioned particle, wherein said polymer coating has an average thickness of between about 1 nm and about 10 nm.

In certain embodiments, the present invention relates to the aforementioned particle, wherein said coating is of a uniform thickness. In certain embodiments, the present invention relates to the aforementioned particle, wherein said thickness does not vary by more than about 10% over the surface of the particle. In certain embodiments, the present invention relates to the aforementioned particle, wherein said thickness does not vary by more than about 5% over the surface of the particle. In certain embodiments, the present invention relates to the aforementioned particle, wherein said thickness does not vary by more than about 1% over the surface of the particle. In certain embodiments, the present invention relates to the aforementioned particle, wherein said polymer coating has a mass per surface area of between about 0.1 µg/cm$^2$ to about 500 µg/cm$^2$. In certain embodiments, the present invention relates to the aforementioned particle, wherein said polymer coating has a mass per surface area of between about 0.1 µg/cm$^2$ to about 100 µg/cm$^2$. In certain embodiments, the present invention relates to the aforementioned particle, wherein said polymer coating has a mass per surface area of between about 0.1 µg/cm$^2$ to about 50 µg/cm$^2$. In certain embodiments, the present invention relates to the aforementioned particle, wherein said polymer coating has a mass per surface area of between about 0.1 µg/cm$^2$ to about 10 µg/cm$^2$. In certain embodiments, the present invention relates to the aforementioned particle, wherein said polymer coating has a mass per surface area of between about 0.1 µg/cm$^2$ to about 5 µg/cm$^2$.

In certain embodiments, the present invention relates to the aforementioned particle, wherein said polymer coating has a dangling bond density of less than about $10^{20}$ spins/cm$^3$. In certain embodiments, the present invention relates to the aforementioned particle, wherein said polymer coating has a dangling bond density of less than about $10^{18}$ spins/cm$^3$. In certain embodiments, the present invention relates to the aforementioned particle, wherein said polymer coating has a dangling bond density of less than about $10^{16}$ spins/cm$^3$.

Another aspect of the present invention relates to a plurality of any of the aforementioned polymer coated particles. In certain embodiments, the present invention relates to the aforementioned particles, wherein said plurality of coated particles are non-agglomerated.

SELECTED METHODS OF THE INVENTION. One aspect of the present invention relates to a method of coating a particle, comprising the steps of: placing said particle in a vessel at a pressure; optionally heating or cooling said vessel to a first temperature; rotating said vessel at a rotating speed for a period of time; mixing together a first gaseous monomer at a first flow rate, and a gaseous initiator at a second flow rate, thereby forming a mixture; introducing said mixture into said vessel via a conduit which comprises a heated filament at a second temperature; heating said mixture with said heated filament, thereby forming a reactive mixture; contacting said particle with said reactive mixture; thereby forming a polymer coating on said particle.

One aspect of the present invention relates to a method of coating a plurality of particles, comprising the steps of: placing said particles in a vessel at a pressure; optionally heating or cooling said vessel to a first temperature; rotating said vessel at a rotating speed for a period of time; mixing together a first gaseous monomer at a first flow rate, and a gaseous initiator at a second flow rate, thereby forming a mixture; introducing said mixture into said vessel via a conduit which comprises a heated filament at a second temperature; heating said mixture with said heated filament, thereby forming a reactive mixture; contacting said particles with said reactive mixture, thereby forming polymer coatings on said particle.

In certain embodiments, the present invention relates to the any of the aforementioned methods, further comprising mixing, with said first gaseous monomer and said gaseous initiator, a second gaseous monomer at a third flow rate. In certain embodiments, said second gaseous monomer is any monomer described herein In certain embodiments, the present invention relates to the any of the aforementioned methods, further comprising mixing, with said first gaseous monomer and said gaseous initiator, a crosslinker at a fourth flow rate. In certain embodiments, said crosslinker is any crosslinker described herein.

In certain embodiments, the present invention relates to the any of the aforementioned methods, wherein the gaseous initiator is selected from the group consisting of compounds of formula I:

A-X—B         I wherein, A is hydrogen, alkyl, cycloalkyl, aryl, heteroaryl, aralkyl or heteroaralkyl; X is —O—O— or —N=N—; and B is hydrogen, alkyl, cycloalkyl, aryl, heteroaryl, aralkyl or heteroaralkyl. In certain embodiments, the present invention relates to the any of the aforementioned methods, wherein A is alkyl. In certain embodiments, the present invention relates to the any of the aforementioned methods, wherein $R^4$ is hydrogen or alkyl. In certain embodiments, the present invention relates to the any of the aforementioned methods, wherein A is hydrogen. In certain embodiments, the present invention relates to the any of the aforementioned methods, wherein B is alkyl. In certain embodiments, the present invention relates to the any of the aforementioned methods, wherein X is —O—O—. In certain embodiments, the present invention relates to the any of the aforementioned methods, wherein X is —N=N—. In certain embodiments, the present invention relates to the any of the aforementioned methods, wherein A is —C(CH$_3$)$_3$; and B is —C(CH$_3$)$_3$. In certain embodiments, the present invention relates to the any of the aforementioned methods, wherein A is —C(CH$_3$)$_3$; X is —O—O—; and B is —C(CH$_3$)$_3$. In certain embodiments, the present invention relates to the any of the aforementioned methods, wherein the gaseous initiator is selected from the group consisting of hydrogen peroxide, alkyl peroxides, aryl peroxides, hydroperoxides, halogens and azo compounds.

In certain embodiments, the present invention relates to the any of the aforementioned methods, wherein said first gaseous monomer is selected from the group consisting of

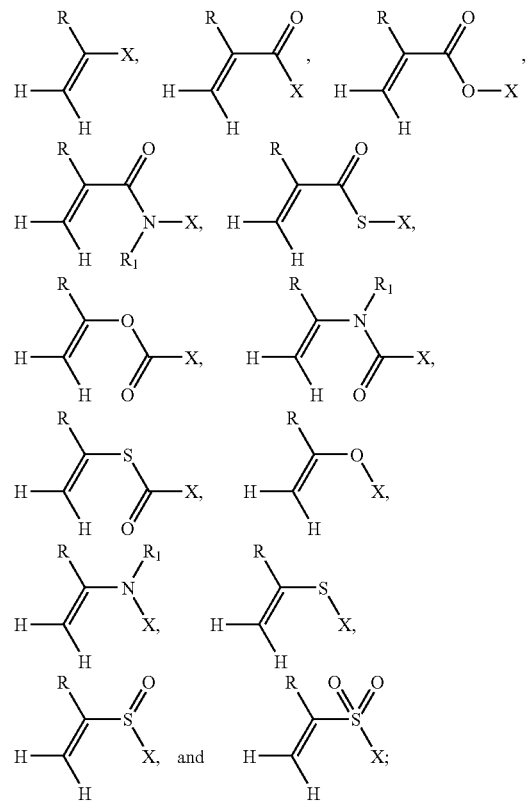

R is selected from the group consisting of hydrogen and alkyl; $R^1$ is selected from the group consisting of hydrogen, alkyl, aralkyl, heteroaralkyl, and carboxyl; X is selected from the group consisting of hydrogen, alkyl, cycloalkyl, heteocycloalkyl, aryl, heteroaryl, aralkyl, heteoaralkyl, and —(CH$_2$)$_n$Y; Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido; and n is 1-10 inclusive.

In certain embodiments, the present invention relates to the any of the aforementioned methods, wherein R is hydrogen. In certain embodiments, the present invention relates to the any of the aforementioned methods, wherein R is methyl. In certain embodiments, the present invention relates to the any of the aforementioned methods, wherein X is —(CH$_2$)$_n$Y. In certain embodiments, the present invention relates to the any of the aforementioned methods, wherein Y is alkyl, cycloalkyl, heterocycloalkyl, aryl, nitro, halo, hydroxyl, alkyoxy, aryloxy, amino, acylamino, amido, or carbamoyl. In certain embodiments, the present invention relates to the any of the aforementioned methods, wherein n is 3-8 inclusive.

In certain embodiments, the present invention relates to the any of the aforementioned methods, wherein said first gaseous monomer is selected from the group consisting of

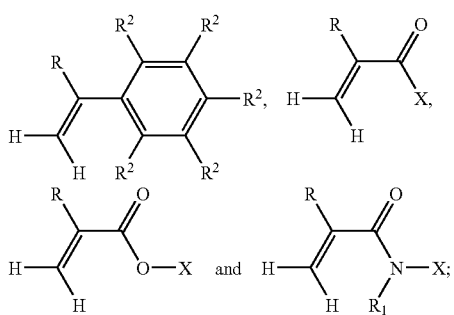

R is selected from the group consisting of hydrogen and alkyl; $R^1$ is selected from the group consisting of hydrogen, alkyl, aralkyl, heteroaralkyl, and carboxyl; $R^2$ is independently selected from the group consisting of hydrogen, alkyl, bromine, chlorine, hydroxyl, alkyoxy, aryloxy, carboxyl, amino, acylamino, amido, carbamoyl, sulfhydryl, sulfonate, and sulfoxido; X is selected from the group consisting of hydrogen, alkyl, cycloalkyl, heteocycloalkyl, aryl, heteroaryl, aralkyl, heteoaralkyl, and —$(CH_2)_nY$; Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido; and n is 1-10 inclusive.

In certain embodiments, the present invention relates to the any of the aforementioned methods, wherein R is hydrogen. In certain embodiments, the present invention relates to the any of the aforementioned methods, wherein R is methyl. In certain embodiments, the present invention relates to the any of the aforementioned methods, wherein $R^1$ is aralkyl or carboxyl. In certain embodiments, the present invention relates to the any of the aforementioned methods, wherein $R^2$ is independently selected from the group consisting of hydrogen, alkyl, bromine and chlorine. In certain embodiments, the present invention relates to the any of the aforementioned methods, wherein X is hydrogen or —$(CH_2)_nY$. In certain embodiments, the present invention relates to the any of the aforementioned methods, wherein Y is alkyl, cycloalkyl, heterocycloalkyl, aryl, nitro, halo, hydroxyl, alkyoxy, aryloxy, amino, acylamino, amido, or carbamoyl. In certain embodiments, the present invention relates to the any of the aforementioned methods, wherein n is 3-8 inclusive.

In certain embodiments, the present invention relates to the any of the aforementioned methods, wherein said first gaseous monomer is selected from the group consisting of

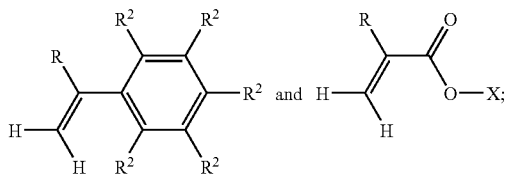

R is selected from the group consisting of hydrogen and methyl; $R^2$ is independently selected from the group consisting of hydrogen, methyl, bromine and chlorine; X is hydrogen or —$(CH_2)_nY$; Y is selected from the group consisting of hydrogen, alkyl, cycloalkyl, heterocycloalkyl, aryl, heteroaryl, aralkyl, heteoaralkyl, nitro, halo, hydroxyl, alkyoxy, aryloxy, carboxyl, heteroaryloxy, amino, acylamino, amido, carbamoyl, sulfhydryl, sulfonate, and sulfoxido; and n is 1-10 inclusive.

In certain embodiments, the present invention relates to the any of the aforementioned methods, wherein R is hydrogen. In certain embodiments, the present invention relates to the any of the aforementioned methods, wherein R is methyl. In certain embodiments, the present invention relates to the any of the aforementioned methods, wherein $R^2$ is independently selected from the group consisting of hydrogen and methyl. In certain embodiments, the present invention relates to the any of the aforementioned methods, wherein $R^2$ is independently selected from the group consisting of hydrogen and bromine. In certain embodiments, the present invention relates to the any of the aforementioned methods, wherein $R^2$ is independently selected from the group consisting of hydrogen and chlorine. In certain embodiments, the present invention relates to the any of the aforementioned methods, wherein Y is hydrogen or heterocyloalkyl. In certain embodiments, the present invention relates to the any of the aforementioned methods, wherein Y is hydrogen. In certain embodiments, the present invention relates to the any of the aforementioned methods, wherein Y is an oxirane. In certain embodiments, the present invention relates to the any of the aforementioned methods, wherein n is 3-8 inclusive.

In certain embodiments, the present invention relates to the any of the aforementioned methods, wherein said first gaseous monomer is selected from the group consisting of poly(glycidyl methacrylate), p-bromophenyl methacrylate, pentabromophenyl methacrylate, n-vinyl carbazole, p-divinyl benzene, styrene, alpha methyl styrene, 2-chlorostyrene, 3-chlorostyrene, 4-chlorostyrene, 2,3-dichlorostyrene, 2,4-dichlorostyrene, 2,5-dichlorostyrene, 2,6-dichlorostyrene, 3,4-dichlorostyrene, 3,5-dichlorostyrene, 2-bromostyrene, 3-bromostyrene, 4-bromostyrene, 2,3-dibromostyrene, 2,4-dibromostyrene, 2,5-dibromostyrene, 2,6-dibromostyrene, 3,4-dibromostyrene, 3,5-dibromostyrene, methyl acrylate, n-butyl acrylate, n-pentyl acrylate, n-hexyl acrylate, n-heptyl acrylate, n-octyl acrylate, 2-ethylhexyl acrylate, perfluorocyclohexylmethyl acrylate, benzyl acrylate, 2-hydroxyethyl acrylate, dimethylaminoethyl acrylate, $Et_3DMAA$, sec-butyl acrylate, tert-butyl acrylate, isobornyl acrylate, ethylene glycol diacrylate, methyl methacrylate, ethyl methacrylate, n-propyl methacrylate, n-butyl methacrylate, isobutyl methacrylate, n-pentyl methacrylate, n-hexyl methacrylate, n-heptyl methacrylate, sec-butyl methacrylate, tert-amyl methacrylate, t-butyl methacrylate, dimethylaminoethyl methacrylate, hydroxyethyl methacrylate, cyclohexyl methacrylate, benzyl methacrylate, isobornyl methacrylate, glycidyl methacrylate, ethylene glycol dimethacrylate, methacrylic acid, styrene, alpha-methyl styrene, ortho-methyl styrene, meta-methyl styrene, para-methyl styrene, para-ethyl styrene, 2,4-dimethyl styrene, 2,5-dimethyl styrene, m-divinylbenzene, p-divinylbenzene, vinylimidazole, N-vinyl-2-pyrrolidone, V3D3, 1,4-divinyloxybutane, diethylene glygol divinyl ether, 1,5-hexadiene-3,4-diol DVG, methyl trans-cinnamate, N-morpholinoethyl acrylate, 2-morpholinoethyl methacrylate, 2-isocyanatoethyl methacrylate, 2-sulfoethyl methacrylate, 2-methoxyethyl methacrylate, 2-(tert-butylamino)ethyl methacrylate, 2-ethoxyethyl methacrylate, 2-chloroethyl methacrylate, 2-hydroxypropyl methacrylate, 2-diethylaminoethyl methacrylate, cyclopentyl methacrylate, 2-(diisopropylamino) ethyl methacrylate, 2-bromoethyl methacrylate, and 2-phenylethyl methacrylate. In certain embodiments, the present invention relates to the any of the aforementioned methods, wherein said first gaseous monomer is poly(glycidyl methacrylate).

In certain embodiments, the present invention relates to the any of the aforementioned methods, wherein said particle is selected from the group consisting of ceramics and glasses, oxides, carbides, nitrides, metals, minerals, semiconductors, polymers, carbon, magnetic particles, superconducting particles-quantum dots, fluorescent particles, colored or dyed particles, colloidal particles, microparticles, microspheres, microbeads, nanoparticles, nanospheres, nanorods, nanowires, shell particles, core particles, organic nanoparticles, and inorganic-organic hybrid nanoparticles.

In certain embodiments, the present invention relates to the any of the aforementioned methods, wherein said particle is selected from the group consisting of fused silica, fumed silica, soda glass, silica, alumina, zirconia, ceria, yttria, and titania, tin oxide, indium oxide, zinc oxide, boron tin oxide, boron zinc oxide, tantalum carbide (TaC), boron carbide ($B_4C$), silicon carbide (SiC), titanium carbide, titanium nitride (TiN), boron nitride ($B_4N$), gold (Au), silicon (Si), silver (Ag), platinum (Pi) nickel (Ni), calcium fluoride ($CaF_2$), quartz, silicon (Si), germanium (Ge), cadmium telluride (CdTd), gallium arsenide (GaAs), polystyrene, polymethylmethacrylate, latex; graphite, fullerenes, nanotubes, and diamond.

In certain embodiments, the present invention relates to the any of the aforementioned methods, wherein said particle is a biologically active substance. In certain embodiments, the present invention relates to the any of the aforementioned methods, wherein said particle is a biologically active substance selected from the group consisting of anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, and prodrugs.

In certain embodiments, the present invention relates to the any of the aforementioned methods, wherein said pressure is atmospheric pressure. In certain embodiments, the present invention relates to the any of the aforementioned methods, wherein said pressure is less than about 1 torr. In certain embodiments, the present invention relates to the any of the aforementioned methods, wherein said pressure is less than about 0.7 torr. In certain embodiments, the present invention relates to the any of the aforementioned methods, wherein said pressure is less than 0.4 torr. In certain embodiments, the present invention relates to the any of the aforementioned methods, wherein said pressure is about 1 torr. In certain embodiments, the present invention relates to the any of the aforementioned methods, wherein said pressure is about 0.7 torr. In certain embodiments, the present invention relates to the any of the aforementioned methods, wherein said pressure is about 0.4 torr.

In certain embodiments, the present invention relates to the any of the aforementioned methods, wherein said first flow rate is about 10 sccm. In certain embodiments, the present invention relates to the any of the aforementioned methods, wherein said first flow rate is less than about 10 sccm. In certain embodiments, the present invention relates to the any of the aforementioned methods, wherein said first flow rate is about 5 sccm. In certain embodiments, the present invention relates to the any of the aforementioned methods, wherein said first flow rate is less than about 5 sccm. In certain embodiments, the present invention relates to the any of the aforementioned methods, wherein said first flow rate is about 3 sccm. In certain embodiments, the present invention relates to the any of the aforementioned methods, wherein said first flow rate is less than about 3 sccm.

In certain embodiments, the present invention relates to the any of the aforementioned methods, wherein said second flow rate is about 1.5 sccm. In certain embodiments, the present invention relates to the any of the aforementioned methods, wherein said second flow rate is less than about 1.5 sccm. In certain embodiments, the present invention relates to the any of the aforementioned methods, wherein said second flow rate is about 0.75 sccm. In certain embodiments, the present invention relates to the any of the aforementioned methods, wherein said second flow rate is less than about 0.75 sccm. In certain embodiments, the present invention relates to the any of the aforementioned methods, wherein said second flow rate is about 10 sccm. In certain embodiments, the present invention relates to the any of the aforementioned methods, wherein said second flow rate is less than about 10 sccm. In certain embodiments, the present invention relates to the any of the aforementioned methods, wherein said second flow rate is about 5 sccm. In certain embodiments, the present invention relates to the any of the aforementioned methods, wherein said second flow rate is less than about 5 sccm. In certain embodiments, the present invention relates to the any of the aforementioned methods, wherein said second flow rate is about 3 sccm. In certain embodiments, the present invention relates to the any of the aforementioned methods, wherein said second flow rate is less than about 3 sccm. In certain embodiments, the present invention relates to the any of the aforementioned methods, wherein said second flow rate is about 1.5 sccm. In certain embodiments, the present invention relates to the any of the aforementioned methods, wherein said second flow rate is less than about 1.5 sccm. In certain embodiments, the present invention relates to the any of the aforementioned methods, wherein said second flow rate is about 0.75 sccm. In certain embodiments, the present invention relates to the any of the aforementioned methods, wherein said second flow rate is less than about 0.75 sccm.

In certain embodiments, the present invention relates to the any of the aforementioned methods, wherein said first temperature is about 25° C. In certain embodiments, the present invention relates to the any of the aforementioned methods, wherein said first temperature is between about 25° C. and 100° C. In certain embodiments, the present invention relates to the any of the aforementioned methods, wherein said first temperature is between about 0° C. and 25° C. In certain embodiments, the present invention relates to the any of the aforementioned methods, wherein said first temperature is controlled by a water bath.

In certain embodiments, the present invention relates to the any of the aforementioned methods, wherein said second temperature is between about 50° C. and about 350° C. In certain embodiments, the present invention relates to the any of the aforementioned methods, wherein said second temperature is between about 100° C. and about 350° C. In certain embodiments, the present invention relates to the any of the aforementioned methods, wherein said second temperature is between about 150° C. and about 350° C. In certain embodiments, the present invention relates to the any of the aforementioned methods, wherein said second temperature is between about 200° C. and about 350° C. In certain embodiments, the present invention relates to the any of the aforementioned methods, wherein said second temperature is between about 250° C. and about 350° C. In certain embodiments, the present invention relates to the any of the aforementioned methods, wherein said second temperature is about 350° C. In certain embodiments, the present invention relates to the any of the aforementioned methods, wherein said second temperature is about 300° C. In certain embodiments, the present invention relates to the any of the aforementioned methods, wherein said second temperature is about 250° C. In certain embodiments, the present invention relates to the any of the aforementioned methods, wherein said second temperature is about 245° C. In certain embodiments, the present invention relates to the any of the aforementioned methods, wherein said second temperature is about 235° C. In certain embodiments, the present invention relates to the any of the aforementioned methods, wherein said second temperature is about 225° C. In certain embodiments, the present invention relates to the any of the aforementioned methods, wherein said second temperature is about 200° C. In certain embodiments, the present invention relates to the any of the aforementioned methods, wherein said second temperature is about 150° C. In certain embodiments, the present invention relates to the any of the aforementioned methods, wherein said second temperature is about 100° C.

In certain embodiments, the present invention relates to the any of the aforementioned methods, wherein said rotating speed is about 50 rpm. In certain embodiments, the present invention relates to the any of the aforementioned methods, wherein said rotating speed is about 100 rpm. In certain embodiments, the present invention relates to the any of the aforementioned methods, wherein said rotating speed is about 150 rpm. In certain embodiments, the present invention relates to the any of the aforementioned methods, wherein said rotating speed is about 200 rpm. In certain embodiments, the present invention relates to the any of the aforementioned methods, wherein said rotating speed is about 250 rpm. In certain embodiments, the present invention relates to the any of the aforementioned methods, wherein said rotating speed is about 300 rpm. In certain embodiments, the present invention relates to the any of the aforementioned methods, wherein said rotating speed is about 350 rpm.

In certain embodiments, the present invention relates to the any of the aforementioned methods, wherein said pressure is 0.4 torr; said first flow rate is about 1.5 sccm; said second flow rate is about 0.2 sccm initiator flow; said second temperature is 235° C. filament temperature; said first temperature is 25° C.; and said rotating speed is about 150 rpm.

In certain embodiments, the present invention relates to the any of the aforementioned methods, further comprising reacting said polymer coating with an electrophile. In certain embodiments, the present invention relates to the any of the aforementioned methods, further comprising reacting said polymer coating with a nucleophile. In certain embodiments, the present invention relates to the any of the aforementioned methods, wherein said nucleophile is an hydroxy-containing compound, amine-containing compound or thiol-containing compound. In certain embodiments, the present invention relates to the any of the aforementioned methods, wherein said nucleophile is an organometallic compound. In certain embodiments, the present invention relates to the any of the aforementioned methods, wherein said nucleophile is an amine-containing compound. In certain embodiments, the present invention relates to the any of the aforementioned methods, wherein said nucleophile is fluorescent. In certain embodiments, the present invention relates to the any of the aforementioned methods, wherein said nucleophile is fluorecein-5-thiosemicarbazide.

SELECTED APPARATUSES OF THE INVENTION. One aspect of the present invention relates to an apparatus for depositing a polymer coatings on a plurality of particles comprising a rotating vessel; a vapor feedline for delivering vapors into said rotating vessel through exit holes; and a filament wire in proximity to said exit holes.

In certain embodiments, the present invention relates to the aforementioned apparatus, wherein said vapor feedline further comprises an in-line sheathed heater. In certain embodiments, the present invention relates to the aforementioned apparatus, wherein said vapor feedline is stainless steel. In certain embodiments, the present invention relates to the aforementioned apparatus, wherein said exit holes are substantially evenly spaced. In certain embodiments, the present invention relates to the aforementioned apparatus, wherein said filament wire is a coiled filament wire. In certain embodiments, the present invention relates to the aforementioned apparatus, wherein said rotating vessel is glass. In certain embodiments, the present invention relates to the aforementioned apparatus, further comprising a temperature-controlled bath for controlling the temperature of the rotating vessel. In certain embodiments, the present invention relates to the aforementioned apparatus, further comprising a flow control system to control the flow of said vapors. In certain embodiments, the present invention relates to the aforementioned apparatus, further comprising a pressure control system. In certain embodiments, the present invention relates to the aforementioned apparatus, wherein said pressure control system comprises a dry pump system.

Another aspect of the present invention relates to an apparatus for depositing a polymer coatings on a plurality of particles comprising a vessel; a means for rotating said vessel; a means for introducing vapors into said vessel; and a means for heating said vapors. In certain embodiments, the present invention relates to the aforementioned apparatus, further comprising a means for controlling the temperature of said vessel. In certain embodiments, the present invention relates to the aforementioned apparatus, further comprising a means for controlling the pressure in said vessel.

EXEMPLIFICATION

The invention will now be described more fully with reference to the accompanying examples, in which certain preferred embodiments of the invention are shown. This invention may, however, be embodied in many different forms and should not be construed as limited to the embodiments set forth herein.

Example 1 iCVD Encapsulation

The iCVD setup can be configured in different ways. It can be set up as a one-dimensional flow-through system that has been detailed elsewhere (e.g., FIG. 7). It can alternatively be set up to allow particle agitation using a rotary mechanism to create a rotating particle bed (e.g., FIG. 8). In one example, glycidyl methacrylate (Aldrich) and tert-amyl peroxide (Aldrich) were used as-received and fed into the coating chamber at 3.0 and 0.3 sccm, respectively, using precision mass flow controllers (MKS Instruments). The liquid monomer source was heated to 85° C. to generate enough vapor pressure. Pressure was maintained at 0.35 Torr (46.7 Pa) by a downstream throttle valve (MKS Instruments) and a capacitance manometer gauge (MKS Instruments). Vacuum was achieved by a dry pump (iQDP40, BOC Edwards) and a roots blower (WAU-150, Leybold). The initiator was thermally activated using electrically resistive wires heated to 250° C. by a DC power supply (DHP 150-20 Sorensen). A water bath at 30° C. provided cooling to the particle bed to promote adsorption of active species and monomer vapor for polymerization.

For the encapsulation of carbon nanotubes, 0.02 g of multiwalled carbon nanotubes (95% purity, 20-50 nm diameter, 5-20 µm length, NanoLab) were charged to the one-dimensional flow system and treated for 50 min.

For the encapsulation of glass microspheres, 5 g of sodalime glass microspheres (25-32 µm diameter, Whitehouse Scientific) were charged to the rotating bed system and treated for 15 min.

Example 2

Coating Characterization

Fourier transform infrared spectroscopy made use of a Thermo Nicolet NEXUS 870 equipped with a DTGS detector. The nanotubes were compressed into KBr pellets and spectra were acquired at 4 cm$^{-1}$ resolution for 64 scans. Transmission electron microscopy was performed on a JEOL 200 CX at 200 kV. The nanotubes were mounted on Cu grids with a Formvar support stabilized with carbon. X-ray photoelectron spectroscopy was done on a Kratos AXIS Ultra using a monochromatic Al anode at 150 W with charge neutralization. Samples were mounted by pressing the microspheres onto a copper adhesive tape. Survey and high resolution elemental scans were acquired at a pass energy of 160 and 10 eV, respectively. Spectra were fitted using the CasaXPS program and referenced to the $C_{1s}$ peak of the saturated aliphatic hydrocarbons ($CH_2/CH_3$) at 285.00 eV. Scanning electron microscopy was done on an FEI/Philips XL30 FEG ESEM under high vacuum at 12.0 kV. The microspheres were mounted by pressing the particles onto carbon tape.

Example 3

Immobilization Experiments

Hexamethylenediamine (Aldrich) was dissolved in neat ethanol (Aldrich) to form a 0.5 M solution. A vial containing 20 mg of PGMA-coated microspheres in 5 ml of the 0.5 M hexamethylenediamine solution was placed in a 60° C. water bath for 5 h. The microspheres were then isolated and washed 5 times with ethanol to remove any unreacted amine. Similarly, 50 mg of fluorescein-5-thiosemicarbazide (Molecular Probes, Invitrogen) were dissolved in 10 ml of pH 8.0 phosphate buffer. A vial containing 20 mg of PGMA-coated microspheres in 5 ml buffer was placed in a 60° C. water bath for 5 h. The microspheres were then isolated and washed 5 times with pH 7.0 phosphate buffer to remove any unreacted dye. For confocal laser scanning microscopy, a Zeiss LSM 510 with a Zeiss Axiovert 100M microscope was used. Excitation was made with an argon laser (458, 488 and 514 nm) and fluorescence was detected between 505-530 nm. Samples were prepared by drying the fluorescently-labeled microspheres on a cover slip and then mounting using SlowFade® Gold reagent (Molecular Probes, Invitrogen) onto a microscope slide. Images were taken with 10× and 63× (oil immersion) objectives.

Example 4

Thickness Estimation

Using information derived from gel permeation chromatography, an estimate of the PGMA coating thickness on the microspheres can be made. First, a calibration curve was made using PGMA polymer standards (Polymer Source) as there is a linear relationship between the GPC peak area and the PGMA concentration of the solution injected into the GPC column (area=4.101×10$^5$ concentration, R$^2$=0.995). This relationship was found to hold true regardless of the polymer molecular weight and molecular weight distribution. Second, 0.4 g of PGMA-coated microspheres were soaked in 3 ml of tetrahydrofuran (J T Baker) to dissolve the coating into solution, after which 1 ml of the solution was filtered through a 0.45 µm PTFE filter and injected into the GPC column. Based on the calibration curve, the area of the GPC trace then allowed the PGMA concentration and mass of PGMA in the 3 ml solution to be determined. By taking the PGMA density to be 1 g/cm$^3$ and the microsphere diameter and density as 28.5 µm and 2.46 g/cm$^3$, respectively, the thickness of PGMA on each particle was calculated.

Example 5

Preliminary Enteric Coating Studies

Figure 11:
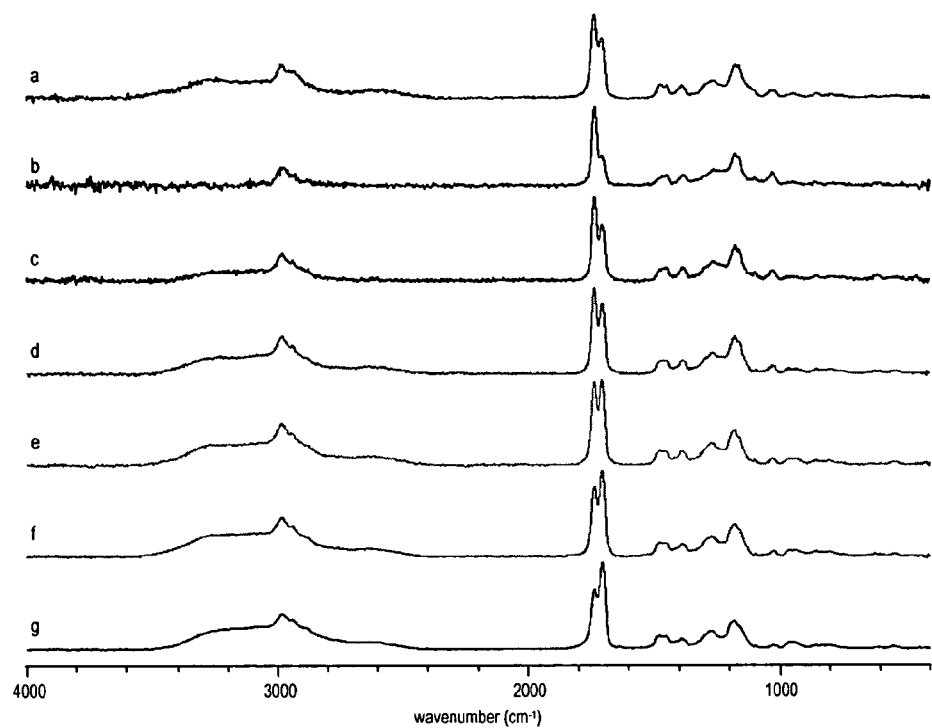
FIG. 11 depicts FTIR spectra of poly(methacrylic acid-co-ethyl acrylate): (a) Eudragit L 100-55, and (b)-(g) CVD copolymers using acid:acrylate feed ratios of (b) 0.007, (c) 0.027, (d) 0.028, (e) 0.033, (f) 0.050, and (g) 0.071.

FIG. 11 shows a series of Fourier transform infrared (FTIR) spectra of poly(methacrylic acid-co-ethyl acrylate) coatings produced via iCVD and one of a USP Type C methacrylic acid copolymer, Eudragit L 100-55, obtained from Röhm. FTIR is specified by the USP as a primary form of identification for methacrylic acid copolymers. The two FTIR peaks centered around 1735 and 1700 cm$^{-1}$ are assigned as the carbonyl peak of the ethyl acrylate unit and methacrylic acid unit, respectively. [Hummel, D. O. *Atlas of Polymer and Plastics Analysis Vol.* 2 (Carl Hanser Verlag, Munich, 1998).] Using methacrylic acid and ethyl acrylate as co-monomers and tert-butyl peroxide as the polymerization initiator, the CVD process is able to produce copolymers with varying fractions of the methacrylic acid unit by adjusting the monomer feed ratios, much like that expected in conventional radical polymerization. It is evident that the composition of the Eudragit film (FIG. 11a) lies within the spectrum of coating compositions that can be made with CVD, comparable to the coating in FIG. 11d.

Figure 12:
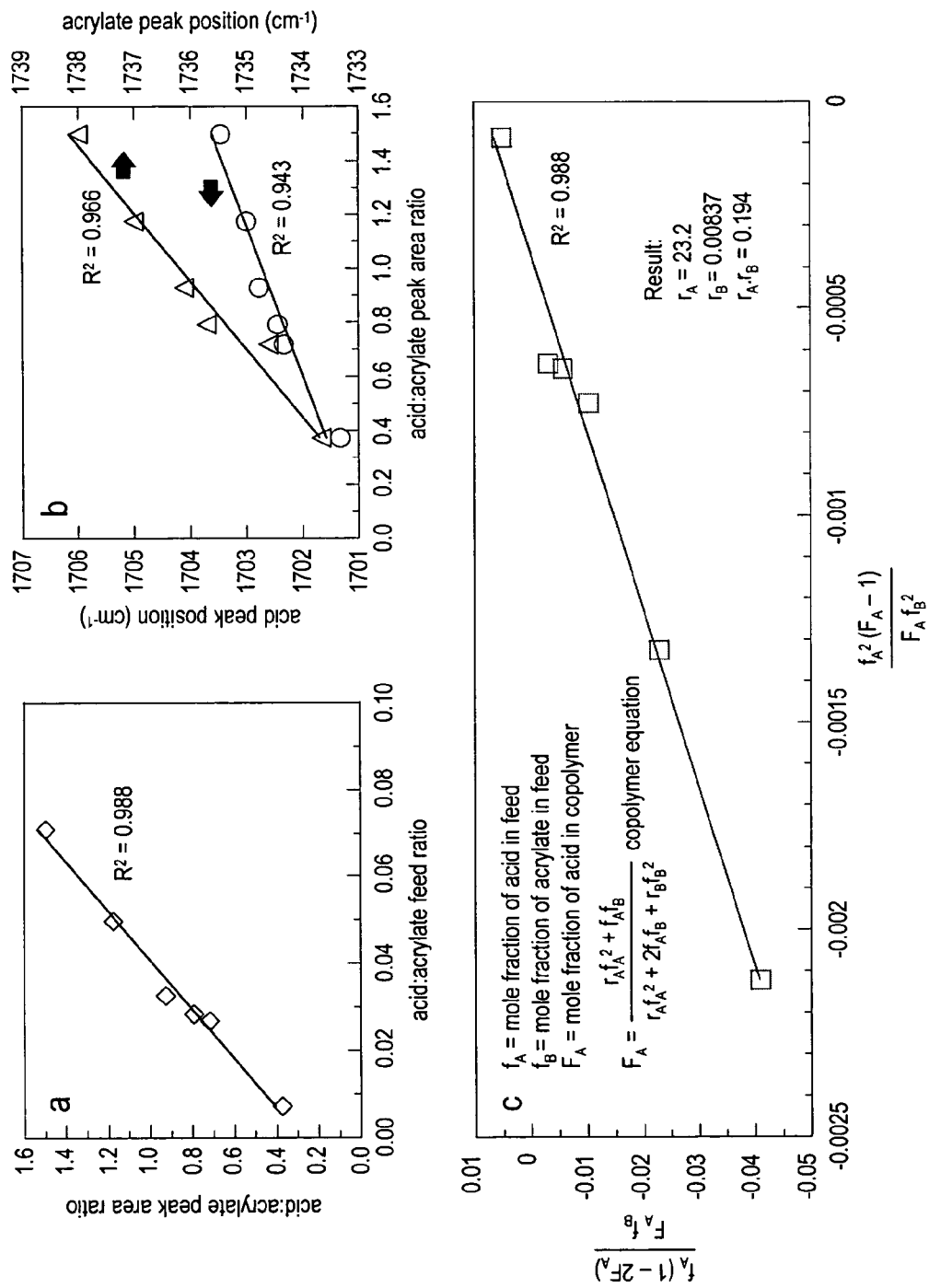
FIG. 12 depicts a (a) plot of acid:acrylate FTIR peak area ratio vs. acid:acrylate feed ratio; (b) plot of acid:acrylate FTIR peak area ratio vs. acid FTIR peak position and acrylate FTIR peak position; and (c) plot to determine reactivity ratios of acid and acrylate units using the copolymer equation.

There is a direct relationship between the acid:acrylate feed ratios and the acid:acrylate peak area ratios in the resulting coatings, as seen in FIG. 12a, this simple relationship ensures that the composition of the CVD coating can match that of the Eudragit material with ease. Also, there is an interesting relationship between the amount of acid incorporated in the copolymer coating and the peak positions of the acid and acrylate peak, as seen in FIG. 12b, with the positions increasing to higher wavenumbers when more acid is present. This implies that the acid and acrylate units are copolymerized and not simply co-deposited as acid and acrylate homopolymers, since there is interaction of the units with changes in composition. With radical copolymerization, reactivity ratios can be calculated through the copolymer equation since the feed and polymer fractions are known, see FIG. 12c. [Odian, G. *Principles of Polymerization* (John Wiley & Sons, New York, 1991).] The reactivity ratios suggest that methacrylic acid favors addition to itself while ethyl acrylate prefers addition to the acid. Further, the product of the ratios is much less than unity, indicating that there is a great tendency towards alternating copolymerization. However, with the acid reactivity ratio much greater than that of the acrylate, there is a tendency towards consecutive polymerization where the acid units are polymerized and consumed first before the acrylate units do. The results in FIGS. 11 and 12 show that CVD is very much analogous to conventional radical polymerization reactions found in solution polymerization, the key difference is that the CVD process makes use of no solvents and combines the polymerization and coating steps into one. These experiments confirm that CVD is able to produce the requisite methacrylic acid copolymer compositions.

Example 6

Enteric Coating Studies

Enteric Coating Properties. Ibuprofen drug particles is coated with a USP Type C methacrylic acid copolymer which is a poly(methacrylic acid-co-ethyl acrylate) in a 1:1 ratio. This composition has already been proven to be attainable using a CVD process (as reported herein). The copolymer properties that are required are specified in the USP/NF official monograph and are given in Table 1 below. [Methacrylic acid copolymer. In USP-NF pp. 2791-2792 (United States Pharmacopeial Convention, Inc., Rockville, Md., 2003).]

Figure 13:
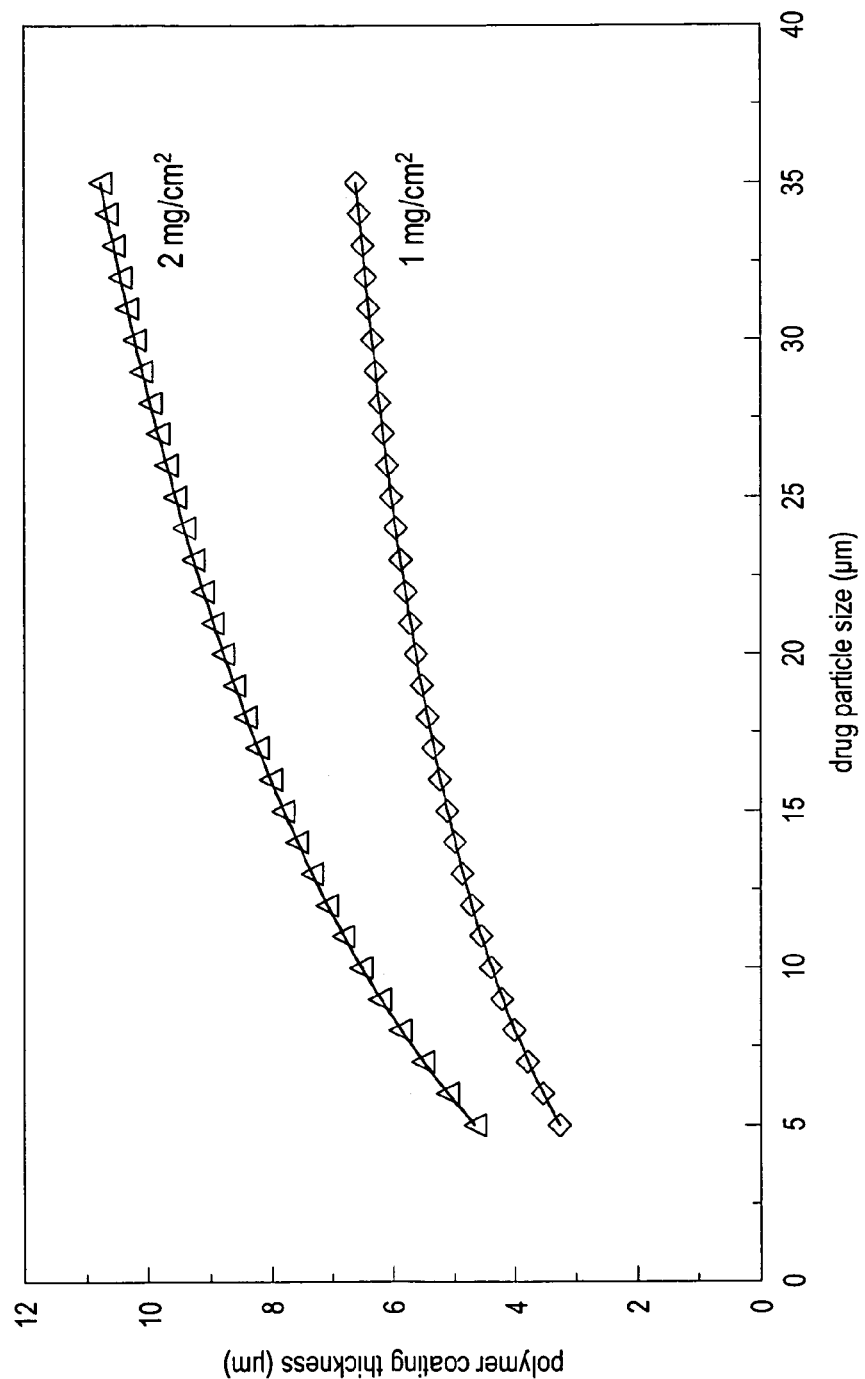
FIG. 13 depicts the minimum polymer coating vs. drug particle size thickness based on Röhm's Eudragit methacrylic acid copolymer loading recommendations (polymer dry weight per unit drug surface area).

Enteric Coating Thickness. A sufficient thickness of coating is required to achieve the proper enteric function, provide a sufficient barrier layer to protect against environments below a pH of 6-7, and eliminate any pinholes which may lead to premature coating failure. To get a basic idea of the coating thickness required, one can look at the values for the methacrylic acid copolymers used in solvent-based coating methods. For the Eudragits, Röhm recommends a minimum polymer loading of 1-2 mg/cm$^2$ (polymer dry weight per drug surface area). Assuming a polymer density of 1 g/cm$^3$, the minimum polymer thickness required is calculated as a function of drug particle size, assuming that the particle is essentially spherical, this is shown in FIG. 13. For a particle of size between 20-35 μm, a minimum coating thickness is on the order of 5-10 μm, while a particle of size between 5-10 μm would need a thickness of 3-6 μm.

TABLE 1

Specifications on USP Type C methacrylic acid copolymer.

| | |
|---|---|
| Poly(methacrylic acid-co-ethyl acrylate) | 1:1 molar ratio |
| Assay of methacrylic acid units | 46.0-50.6% on a dried basis |
| Heavy metals | max. 0.002% |
| Monomers | max. 0.05% |
| Residue on ignition | max. 0.4% |
| Acid value | 300-330 mg KOH/g polymer |
| Density | 0.8-1.1 g/cm$^3$ |

Figure 14:
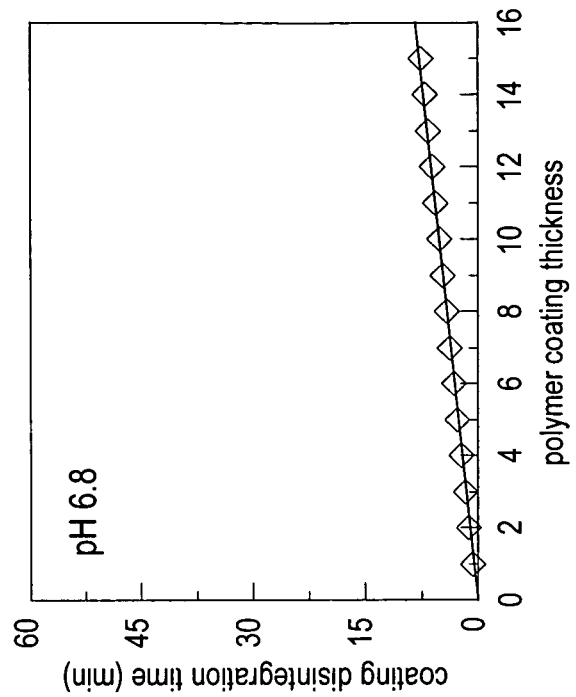
FIG. 14 depicts graphs showing the disintegration time of polymer coating vs. initial polymer coating thickness under dissolution pH of 1.2 and 6.8 (note time axes have different units).
Figure 14:
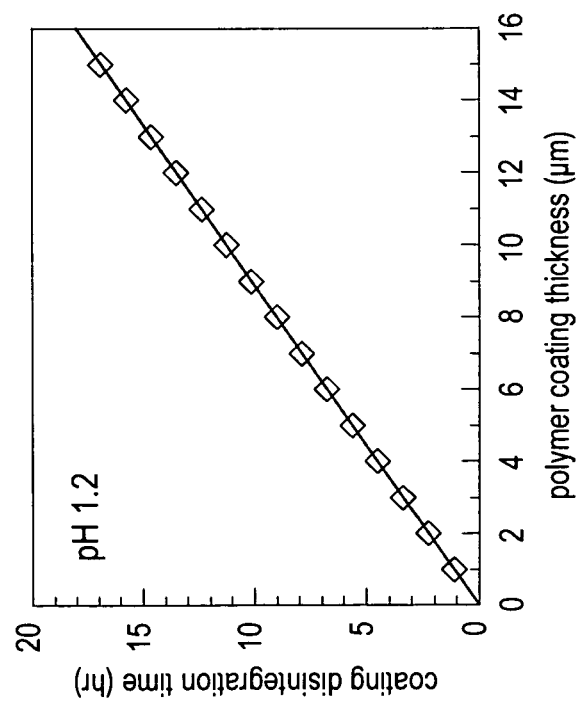

A more rigorous first-principles approach can also be used to obtain an estimate of the polymer coating thickness required. [Ozturk, S. S., Palsson, B. O., Donohoe, B. & Dressman, J. B. Kinetics of release from enteric-coated tablets. *Pharmaceutical Research* 5, 550-565 (1988).] Based on a Fickian diffusion model of a spherical drug core surrounded by a polymer layer, the model takes into account ion dissociation, and diffusion across the polymer and the diffusion boundary layer between the polymer and the bulk solution, assumed to be a sink. Flux equations are set up for the drug, the polymer and the buffer solution, their respective anions and the hydrogen ion. The time for the polymer to reduce from an initial thickness to a specified final thickness is computed. FIG. 14 shows the time for the polymer coating to disintegrate as a function of initial polymer coating thickness for two pH environments, one at pH 1.2 to simulate gastric fluid and one at pH 6.8 to simulate intestinal fluid. For a proper enteric coating, the disintegration time at pH 1.2 should be at least 2 hours, which is the normal time for the drug to pass through the upper gastrointestinal tract and into the duodenum, the disintegration time at pH 6.8 should be minimal since the drug core needs to be exposed for the drug to dissolve and get absorbed by the intestines. Based on the model, coating thickness greater than 2 μm is estimated to be sufficient for enteric function, this agrees reasonably well with the estimates based on the Eudragit recommendations.

Drug Dissolution Performance. For the iCVD polymer to perform as an enteric coating, the polymer must be able to withstand low pH environments as the coated drug passes orally through the esophagus and stomach (pH 1.2) but should rapidly dissolve away to expose the drug when it reaches the duodenum (pH 6-7). This pH sensitivity is tested in vitro using the USP 724 Drug Release test protocol for enteric-coated drugs. [<724> Drug release. In USP-NF pp. 2157-2165 (United States Pharmacopeial Convention, Inc., Rockville, Md., 2003).] It involves pressing the coated drug particles into tablet form for testing in a USP dissolution apparatus 2 (paddle). [<711> Dissolution. In USP-NF pp. 2155-2156 (United States Pharmacopeial Convention, Inc., Rockville, Md., 2003).] A single tablet is introduced into a buffered pH solution at 37±0.5° C. that is constantly stirred by a paddle, aliquots of the solution are assayed at timed intervals using an appropriate drug detection technique, either through gas chromatography or ultra-violet spectroscopy, to determine the amount of drug dissolved with time. The test is done at two successive pH conditions, first the tablet is placed in a simulated gastric fluid using 0.1 N HCl for 2 hours at pH 1.2, the solution pH is then raised to 6.8 using buffered phosphate solution to simulate intestinal fluid and the tablet is further subjected for another 45 min. Enteric function is acceptable when the CVD-coated tablets satisfy the target levels specified in Table 2.

TABLE 2

Dissolution target levels specified in the USP 724 Drug Release test protocol for enteric-coated articles.

| | |
|---|---|
| pH 1.2 | 0.1 N HCl for 2 h at 37 ± 0.5° C. |
| Level A1 | 6 tested tablets, no individual tablet >10% dissolved |
| Level A2 | 6 tested tablets, average of A1 and A2 ≤10% dissolved and no individual unit >25% dissolved |
| Level A3 | 12 tested tablets, average of A1, A2 and A3 ≤10% dissolved and no individual unit >25% dissolved |
| pH 6.8 | Buffered phosphate solution for 45 min at 37 ± 0.5° C. |
| Level B1 | 6 tested tablets, each unit ≥80% dissolved |
| Level B2 | 6 tested tablets, average of B1 and B2 ≥75% dissolved and no individual unit <60% dissolved |
| Level B3 | 12 tested tablets, average of B1, B2 and B3 ≥75% dissolved, not more than 2 units <60%, and no unit <50% dissolved |

Chemical Characterization of iCVD Coatings. Coating composition and structure are characterized using FTIR and $^1$H solution NMR. A one-to-one molar ratio of methacrylic acid and ethyl acrylate units is required for the USP Type C copolymer. Acid value of the methacrylic acid copolymers will also be determined by titrimetry according to the USP 541 protocol. [<541> Titrimetry. In USP-NF pp. 2229-2232 (United States Pharmacopeial Convention, Inc., Rockville, Md., 2003).] Molecular weight and MW distribution is determined using gel permeation chromatography (GPC), Röhm reports their Eudragit material to be approximately 250,000 MW. Differential scanning calorimetry (DSC) is used to ascertain thermal transitions. DSC is especially useful to determine the integrity of ibuprofen ($T_m$=75° C.) after the coating process, i.e., there are no adverse interactions of the monomers, initiator or the polymer with the underlying drug core. [Castelli, F., Messina, C., Sarpietro, M. G., Pignatello, R. & Puglisi, G. Eudragit as controlled release system for anti-inflammatory drugs A comparison between DSC and dialysis experiments. *Thermochimica Acta* 400, 227-234 (2003).] Purity of the coating is determined through $^1$H solution NMR. Coatings are also be assayed for heavy metals, arsenic and ash residue according to the USP 231 (method II)28, USP 211 (method II)29 and USP 28130 protocols, respectively.

Morphological Characterization of iCVD Coatings. Coating thickness on ibuprofen particles is measured using SEM by analyzing the size of the particles before and after coating treatment. SEM will also provide information on coating uniformity and conformality, whether individual particles have been effectively coated. Mechanical sieving is used to identify any particle agglomeration from the coating process, particles will be sieved to determine the minimum sieve size which the particles can pass through, minimal shaking force will prevent any false negatives from agglomerate breakup due to sieving. Determining the coating thickness will allow deposition rates to be calculated and the iCVD process optimized for rapid coating, based on optimizing CVD reactor variables such as reactor pressure, reactant flow rates, and the activation temperature. [<231> Heavy metals. In USP-NF pp. 2204-2205 (United States Pharmacopeial Convention, Inc., Rockville, Md., 2003); <211> Arsenic. In USP-NF pp. 2055-2056 (United States Pharmacopeial Convention, Inc., Rockville, Md., 2003); and <281> Residue on ignition. In USP-NF p. 2061 (United States Pharmacopeial Convention, Inc., Rockville, Md., 2003).]

Example 7

Further Enteric Coating Studies iCVD Copolymerization. The iCVD described below was performed using continuous flow reactors which are capable of depositing on silicon flats and around three-dimensional particles. For the P(MAA-EA) system, polymerization utilized methacrylic acid (Aldrich, 99%) and ethyl acrylate (Aldrich, 99%) as the comonomers, and tert-butyl peroxide (Aldrich, 98%) as the radical initiator. All reactants were used as received. The MAA source vessel was heated to 70° C. to enable sufficient vapor flow. A range of copolymers were produced by systematically varying the MAA flowrate, $F_{MAA}$=0.15, 0.59, 0.68, 1.03 and 1.47 sccm, while keeping all other conditions constant: $F_{EA}$=20.8 sccm, $F_{TBPO}$=0.80 sccm, $T_{filament}$=260° C., $T_{substrate}$=25° C., and P=3.0 Torr. For the P(MAA-EDMA) system, ethylene dimethacrylate (Aldrich, 98%) was used instead as the alternate comonomer, which also acted as a crosslinking agent, while tert-amyl peroxide (Aldrich, 97%) was the radical initiator. The EDMA source vessel was likewise heated to 100° C. to achieve sufficient vapor flow. Depositions were made at the prescribed conditions: $F_{MAA}$=0.60 sccm, $F_{EDMA}$=0.10 sccm, $F_{TAPO}$=0.10 sccm, $T_{filament}$=285° C., $T_{substrate}$=20° C., and P=0.5 Torr.

Coating Characterization. FTIR was carried out on a Thermo Nicolet NEXUS 870 equipped with a DTGS detector and KBr beam splitter. Spectra were acquired at 4 cm$^{-1}$ resolution for 64 scans. XPS made use of a Kratos AXIS Ultra with a 150 W monochromatized Al source and charge neutralization. Characterizations were made on methacrylic acid copolymers deposited on silicon substrates. Additionally, GPC was performed on a P(MAA-EA) copolymer using a Waters Breeze system with Styragel HR columns and tetrahydrofuran (JT Baker, HPLC grade) as the elution solvent. The copolymer sample was dissolved off the silicon wafer using THF prior to analysis. Molecular weight and molecular weight distribution were determined against a calibration from a set of narrow poly(methyl methacrylate) standards. $M_n$ and PDI were determined to be 8,900 g.mol$^{-1}$ and 2.24, respectively.

Swelling Measurements. Data was taken on a J. A. Woollam M-2000S spectroscopic ellipsometer with a soak cell attachment. Raw $\Psi$ and $\Delta$ angles were measured at a 75° incident angle for 220 wavelengths between 251 and 718 nm. Dry copolymer film thickness ($d_o$) was determined by fitting experimental data to a Cauchy model. Swollen film thickness during soak in various pH buffers ($d_o$+$\Delta$d) was determined by fitting experimental data to an effective medium approximation of the Cauchy copolymer representation and water. Measurements were made on methacrylic acid copolymers deposited on silicon substrates.

Release Measurements. Release in various pH buffers was traced by measuring changes in light absorption over time. For fluorescein, release was monitored at 490 nm, comparing fluorescein layered on silicon substrates that were exposed or encapsulated with an iCVD P(MAA-EDMA) coating. For ibuprofen, 25 µm ibuprofen microcrystals (DuPont), that were bare or encapsulated with an iCVD P(MAA-EDMA) coating, were compressed into pellets and their release monitored at 220 nm. Absorption was measured on a Varian Cary 6000i.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A method, comprising the steps of:
   placing a plurality of individual particles in a vessel at a pressure; wherein said vessel comprises a vapor feedline for delivering vapors into said vessel through exit holes, and a filament in proximity to said exit holes; the individual particles consist of soda glass, silica, carbon, or a drug; and the diameters of said individual particles are about 5 µm to about 35 µm;

contacting said vessel with a water bath at a first temperature, wherein said first temperature is between about 0° C. and about 100° C.;
rotating said vessel at a rotating speed for a period of time;
mixing together a first gaseous monomer at a first flow rate, and a gaseous initiator at a second flow rate, thereby forming a mixture;
introducing said mixture into said vessel via said vapor feedline which comprises said filament at a second temperature, wherein said second temperature is between about 150° C. and 350° C.;
heating said mixture with said filament, thereby forming a reactive mixture;
contacting said plurality of individual particles with said reactive mixture; thereby forming a plurality of individual coated particles, wherein each individual coated particle consists of a substantially uniform polymer coating encapsulating one individual particle; the thickness of said substantially uniform polymer coating is about 3 μm to about 12 μm; each individual particle is non-agglomerated; and the plurality of individual coated particles is non-agglomerated.

2. The method of claim 1, wherein the gaseous initiator is selected from the group consisting of compounds of formula I:

A-X—B      I wherein,
A is hydrogen, alkyl, cycloalkyl, aryl, heteroaryl, aralkyl or heteroaralkyl;
X is —O—O— or —N═N—; and
B is hydrogen, alkyl, cycloalkyl, aryl, heteroaryl, aralkyl or heteroaralkyl.

3. The method of claim 1, wherein the gaseous initiator is selected from the group consisting of hydrogen peroxide, alkyl peroxides, aryl peroxides, hydroperoxides, halogens and azo compounds.

4. The method of claim 1, wherein said first gaseous monomer is selected from the group consisting of

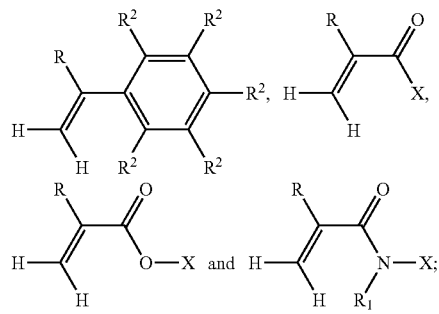

R is selected from the group consisting of hydrogen and alkyl;
R¹ is selected from the group consisting of hydrogen, alkyl, aralkyl, heteroaralkyl, and carboxyl;
R² is independently selected from the group consisting of hydrogen, alkyl, bromine, chlorine, hydroxyl, alkoxy, aryloxy, carboxyl, amino, acylamino, amido, carbamoyl, sulfhydryl, sulfonate, and sulfoxido;

X is selected from the group consisting of hydrogen, alkyl, cycloalkyl, heteocycloalkyl, aryl, heteroaryl, aralkyl, heteoaralkyl, and —(CH₂)ₙY;
Y is selected from the group consisting of hydrogen, alkyl, cycloalkyl, heterocycloalkyl, aryl, heteroaryl, aralkyl, heteoaralkyl, nitro, halo, hydroxyl, alkoxy, aryloxy, carboxyl, heteroaryloxy, amino, acylamino, amido, carbamoyl, sulfhydryl, sulfonate, and sulfoxido; and
n is 1-10 inclusive.

5. The method of claim 4, wherein R is methyl.
6. The method of claim 4, wherein X is hydrogen or —(CH₂)ₙY.
7. The method of claim 4, wherein Y is alkyl, cycloalkyl, heterocycloalkyl, aryl, nitro, halo, hydroxyl, alkoxy, aryloxy, amino, acylamino, amido, or carbamoyl.
8. The method of claim 4, where n is 3-8 inclusive.
9. The method of claim 4, wherein said first gaseous monomer is selected from the group consisting of

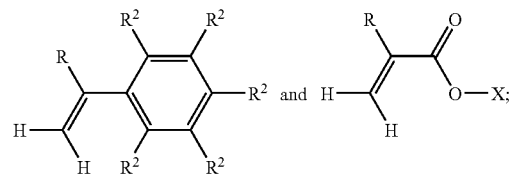

R is selected from the group consisting of hydrogen and methyl;
R² is independently selected from the group consisting of hydrogen, methyl, bromine and chlorine;
X is hydrogen or —(CH₂)₂Y;
Y is selected from the group consisting of hydrogen, alkyl, cycloalkyl, heterocycloalkyl, aryl, heteroaryl, aralkyl, heteoaralkyl, nitro, halo, hydroxyl, alkoxy, aryloxy, carboxyl, heteroaryloxy, amino, acylamino, amido, carbamoyl, sulfhydryl, sulfonate, and sulfoxido; and
n is 1-10 inclusive.

10. The method of claim 9, wherein R is methyl.
11. The method of claim 9, wherein Y is hydrogen or heterocycloalkyl.
12. The method of claim 9, wherein Y is hydrogen.
13. The method of claim 9, wherein Y is an oxirane.
14. The method of claim 9, wherein n is 3-8 inclusive.
15. The method of claim 1, wherein said individual particles consist of soda glass.
16. The method of claim 1, wherein the average particle size of the plurality of individual coated particles is not more than 5% larger than the average particle size of the plurality of individual particles, apart from the particle size increase attributable to the coating itself.
17. The method of claim 1, wherein said individual particles consist of silica.
18. The method of claim 1, wherein said individual particles consist of carbon.
19. The method of claim 1, wherein said individual particles consist of carbon in the form of graphite, a fullerene, a nanotube, or diamond.
20. The method of claim 1, wherein said individual particles consist of a drug.

* * * * *